US012761144B2

(12) United States Patent
Wu et al.

(10) Patent No.: US 12,761,144 B2
(45) Date of Patent: Oct. 13, 2026

(54) SYSTEMS AND METHODS OF SPECTROPHOTOMETRY FOR THE DETERMINATION OF GENOME CONTENT, CAPSID CONTENT AND FULL/EMPTY RATIOS OF ADENO-ASSOCIATED VIRUS PARTICLES

(71) Applicant: REGENXBIO INC., Rockville, MD (US)

(72) Inventors: Zhuchun Wu, Rockville, MD (US); Keith Webber, Rockville, MD (US); Brian Howie, Rockville, MD (US); Li Zhi, Rockville, MD (US)

(73) Assignee: REGENXBIO Inc., Rockville, MD (US)

( * ) Notice: Subject to any disclaimer, the term of this patent is extended or adjusted under 35 U.S.C. 154(b) by 872 days.

(21) Appl. No.: 17/050,942

(22) PCT Filed: Apr. 27, 2019

(86) PCT No.: PCT/US2019/029540

§ 371 (c)(1),
(2) Date: Oct. 27, 2020

(87) PCT Pub. No.: WO2019/212922

PCT Pub. Date: Nov. 7, 2019

(65) Prior Publication Data

US 2021/0231560 A1 Jul. 29, 2021

Related U.S. Application Data

(60) Provisional application No. 62/812,898, filed on Mar. 1, 2019, provisional application No. 62/671,965, filed on May 15, 2018, provisional application No. 62/664,251, filed on Apr. 29, 2018.

(51) Int. Cl.

| | |
|---|---|
| ***G01N 21/33*** | (2006.01) |
| ***A61K 35/76*** | (2015.01) |
| ***C12N 15/86*** | (2006.01) |
| ***C12Q 1/70*** | (2006.01) |
| ***G01N 30/02*** | (2006.01) |
| ***G01N 33/68*** | (2006.01) |

(52) U.S. Cl.

CPC ............ *G01N 21/33* (2013.01); *A61K 35/76* (2013.01); *C12N 15/86* (2013.01); *C12Q 1/70* (2013.01); *G01N 30/02* (2013.01); *G01N 33/6827* (2013.01); *C12N 2750/14143* (2013.01); *G01N 2030/027* (2013.01); *G01N 2333/075* (2013.01)

(58) Field of Classification Search

CPC .... G01N 21/33; G01N 30/02; G01N 33/6827; G01N 2030/027; G01N 2333/075; G01N 2030/8827; G01N 2030/8831; A61K 35/76; C12N 15/86; C12N 2750/14143; C12N 2750/14122; C12N 2750/14151; C12Q 1/70

See application file for complete search history.

(56) References Cited

U.S. PATENT DOCUMENTS

| | | | |
|---|---|---|---|
| 7,261,544 | B2 | 8/2007 | Qu |
| 2004/0110266 | A1 | 6/2004 | Chiorini et al. |

FOREIGN PATENT DOCUMENTS

| | | |
|---|---|---|
| WO | 99/61643 | 12/1999 |
| WO | 2016118520 | 7/2016 |
| WO | 2017100676 | 6/2017 |

OTHER PUBLICATIONS

Huffman, S.; Soni, K.; Ferrailo, J. UV-Vis Based Determination of Protein Concentration: Validating and Implementing Slope Measurements Using Variable Pathlength Technology. BioProcess International 2014, 12 (8), 2-8.*

Xie, Q.; Hare, J.; Turnigan, J.; Chapman, M. S. Large-Scale Production, Purification and Crystallization of Wild-Type Adeno-Associated Virus-2. Journal of Virological Methods 2004, 122 (1), 17-27.*

Clement et al. "Manufacturing of recombinant adeno-associated viral vectors for clinical trials" Molecular therapy Methods & clinical development 3 (2016) (Year: 2016).*

International Search Report for PCT/US2019/029540, mailed Oct. 28, 2019, 8 pages.

Written Opinion of the ISA for PCT/US2019/029540, mailed Oct. 28, 2019, 14 pages.

Sommer et al., "Quantification of adeno-associated virus particles and empty capsids by optical density measurement", Molecular Therapy, vol. 7, No. 1, Jan. 1, 2003, pp. 122-128.

Webber, K., et al., "The Application of Spectrophotometry for the Estimation of Genome Copies and Full versus Empty Ratios of Adeno-associated Particles", ASGCT 21st Annual Meeting (May 19, 2018).

Msagati Tam et al., "Evaluation of methods for the isolation, detection and quantification of cyanobacterial hepatotoxins", Aquatic Toxicology, vol. 78, No. 4, pp. 382-397 (2006).

Takahashi E et al., "Quantitation of adenovirus type 5 empty capsids", Analytical Biochemistry, Elsevier, vol. 349, No. 2, pp. 208-217 (2006).

Debelak D et al., "Cation-exchange high-performance liquid chromatography of recombinant adeno-associated virus type 2", Journal of Chromatography B, vol. 740, No. 2, pp. 195-202 (2000).

(Continued)

*Primary Examiner* — Olivia M. Wise
*Assistant Examiner* — Francini Alvarenga Fonseca Lopez
(74) *Attorney, Agent, or Firm* — Nixon & Vanderhye, PC

(57) ABSTRACT

The present disclosure relates to using spectrophotometry to estimate genome copies and full/empty ratios adeno-associated virus particles.

9 Claims, 27 Drawing Sheets

(56) References Cited

OTHER PUBLICATIONS

Fridolin I et al., "On-line monitoring of solutes in dialysate using wavelength-dependent absorption of ultraviolet radiation", Medical & Biological Engineering & Computing, vol. 41, No. 3, pp. 263-270 (2003).

Silva Jessica Thais Do Prado et al., "Analytical validation of an ultraviolet-visible procedure for determining lutein concentration and application to lutein-loaded nanoparticles", Food Chemistry, vol. 230, pp. 336-342 (2017).

Vellekamp G et al: "Empty capsids in col. purified recombinant adenovirus preparations", Human Gene Therapy, Mary Ann Liebert, Inc. Publishers, GB, vol. 12, No. 15, Oct. 10, 2001 (Oct. 10, 2001), pp. 1923-1936, XP002382733, ISSN: 1043-0342, DOI: 10.1089/104303401753153974.

Dorange et al., "Analytical approaches to characterize AAV vector production & purification: Advances and challenges", Cell and Gene Therapy Insights, vol. 4, No. 2, Mar. 14, 2018 (Mar. 14, 2018), pp. 119-129, XP055606522, ISSN: 2059-7800, DOI: 10.18609/cgti.2018.015.

* cited by examiner

| Spectra Scan | GC/mL | Capsid/ mL | % Full Capsid |
|---|---|---|---|
| Original Spectra | $7.7/10^{12}$ | $1.6/10^{13}$ | 49% |
| Corrected Spectra | $6.9 \times 10^{12}$ | $1.7 \times 10^{13}$ | 41% |

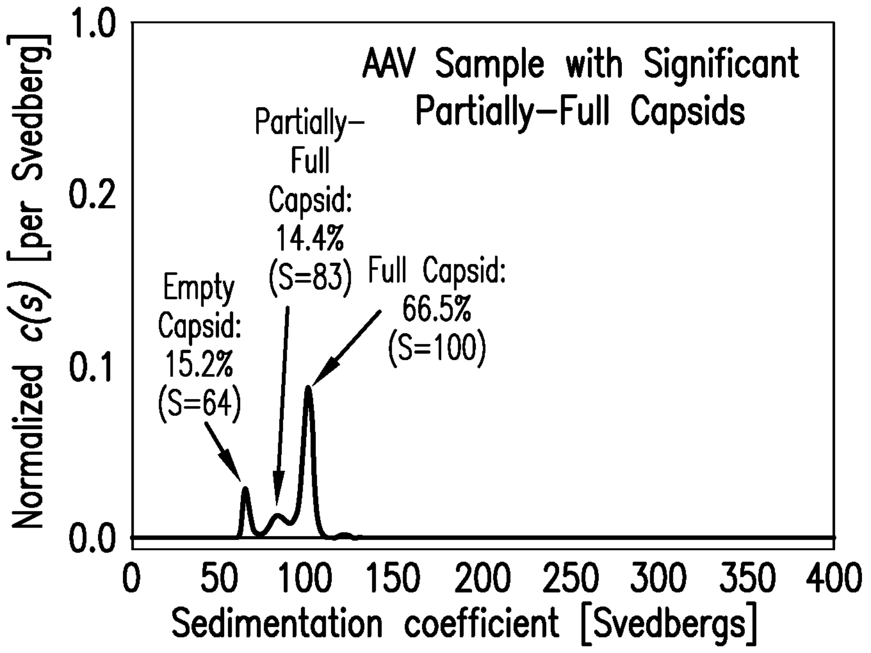

| Analysis Method | % Full Capsids |
|---|---|
| Spectrophotometry | 45.2 |
| Raw Adjusted AUC Value | 74.1 |
| Normalized AUC Value | 77.1 |
| Corrected AUC Value | 45.7 |

The partially full capsid has 53% of the S value between the empty capsid and full capsid; therefore the partially−full capsids have an average level of 53% of the total DNA of the full capsids.
Raw Adjusted AUC Value adds 53% of the 14.4% partially full capsids to the full capsid value (66.5%+7.6%).

FIG.7

UV absorbance of AAV and its DNA and capsid protein components

SEC−HPLC chromatogram of AAV serotype 8

Spectrum of AAV serotype 8 by spectrophotometer

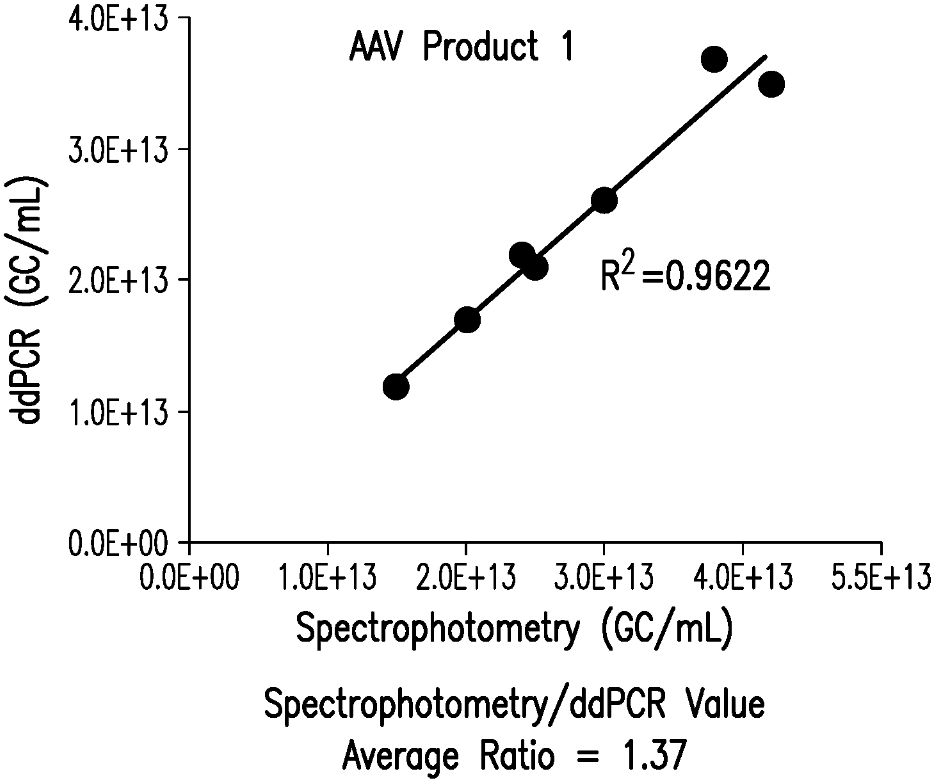
Spectrophotometry/ddPCR Value
Average Ratio = 1.37
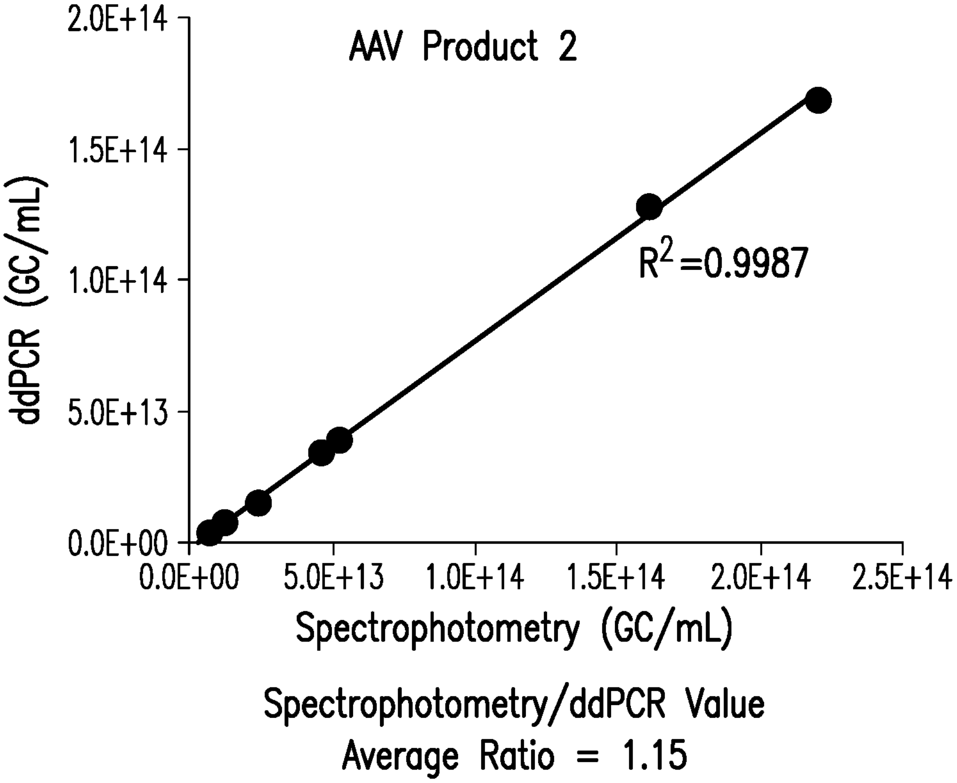
Spectrophotometry/ddPCR Value
Average Ratio = 1.15
FIG.16

| Spectrophotometry % Full | AUC % Full | Adjusted AUC % Full | Spectrophotometry / AUC Ratio |
|---|---|---|---|
| 60.9 | 85.3 | 61.8 | 0.99 |
| 53.8 | 82.3 | 56.6 | 0.95 |
| 56.3 | 84.9 | 61.1 | 0.92 |
| 53.5 | 82.4 | 56.7 | 0.94 |
| 54.8 | 82.8 | 57.4 | 0.96 |
| 52.1 | 80.1 | 52.9 | 0.99 |
| 50.1 | 79.3 | 51.7 | 0.97 |

| Qualification Test | Genome Content | Capsid Content | %Full Capsids |
|---|---|---|---|
| Repeatability Precision (6 preparations, 1 analyst, 1 instrument) | 0.7% RSD | 0.8% RSD | 0.5% RSD |
| Intermediate Precision (12 preparations total, 2 analysts, 2 instruments) | 1.6% RSD | 1.5% RSD | 0.4% RSD |
| Assay Range | ≥8.0E+11 GC/mL | ≥1.3E+12 Capsid/mL | 12–60% Full |

FIG.20A

SYSTEMS AND METHODS OF SPECTROPHOTOMETRY FOR THE DETERMINATION OF GENOME CONTENT, CAPSID CONTENT AND FULL/EMPTY RATIOS OF ADENO-ASSOCIATED VIRUS PARTICLES

CROSS-REFERENCE TO RELATED APPLICATIONS

This application is the U.S. national phase of International Application No. PCT/US2019/029540 filed Apr. 27, 2019, which designated the U.S. and claims the benefit of priority of U.S. Provisional Application Nos. 62/664,251 filed Apr. 29, 2018, 62/671,965 filed May 15, 2018, and 62/812,898 filed Mar. 1, 2019, the entire content of each of which is incorporated herein in its entirety.

TECHNICAL FIELD

The present disclosure relates to using spectrophotometry or HPLC to determine genome content, capsid content and full/empty ratios of adeno-associated virus particles, as well as using HPLC to determine absolute concentration of proteins and DNAs.

BACKGROUND

Polymerase Chain Reaction (PCR) is a common technique for determining the genome content of adeno-associated viruses (AAV), and Analytical Ultracentrifugation (AUC) is commonly used for estimating the level of empty capsids (containing only the protein capsids with no DNA) and full capsids (containing both protein and DNA). However, both techniques require multiple steps with complicated procedures that are time-consuming and relatively low-throughput, and more efficient and better quantitative techniques for development sample screening, in-process sample analysis for process control and monitoring, final product concentration determination and stability monitoring are desirable.

SUMMARY

Spectrophotometry is a common method for measuring concentration of products with known extinction coefficients at specific wavelengths and is widely used to determine the protein content for therapeutic proteins. AAV content is more complicated to determine through spectrophotometry than many other therapeutic products because AAV contains two major species absorbing at different wavelength maxima (protein capsids at 280 nm, and DNA at 260 nm). Additionally, AAV capsid samples contain a heterogeneous mixture of empty and full capsids, and potentially impurities such as host cell DNA and host cell proteins.

The inventors have unexpectedly discovered that, as described herein by way of example and without limitation, determining AAV content directly by spectrophotometry is possible for AAV samples without prior sample treatment based on a methodology derived to determine both the level of genome copies and total capsids per sample. This methodology can be further utilized to calculate the ratio of empty and full capsids. The methods described herein provide more immediate yet accurate genome-specific and/or a capsid-specific quantity determinations.

The methodology has been demonstrated to be precise and linear. Genome values calculated by spectrophotometry have a good correlation to values determined by the PCR method and the estimated distribution of empty and full capsids calculated by spectrophotometry also correlate well with AUC values.

In short, spectrophotometry, optionally combined with baseline matrix interference subtraction, is a faster and high-throughput alternative to the labor-intensive methods commonly used for AAV analysis for the determination of genome and capsid content. For example, AAV products may be in low concentration or matrix interference from buffer components may impact the spectra profile and AAV content determination, therefore a baseline matrix interference subtraction such as HPLC can further improve the described UV process for determining genome and capsid content.

In addition to UV absorbance measurement, HPLC with UV detection at 260 nm and 280 nm can also be used to measure the absolute vector genome and capsid titer. The vector genome titer and capsid titer are directly calculated from peak areas at 260 nm and 280 nm. Quantification by HPLC using this method is absolute and no calibration curve is needed. The HPLC methods provided herein represent another easier, faster, more precise and reproducible means to determine the vector genome titer and capsid titer than PCR methods.

The absolute HPLC quantification method provided herein is applicable to protein, DNA, biopolymers and small molecules. Conventional HPLC quantification is relative and utilizes a standard to generate calibration curve. Using the method provided herein, the UV detector of the HPLC systems is operated similarly as a spectrophotometer. No calibration curve is needed in quantitative analysis. The HPLC method provided herein is an absolute quantification method, in comparison with conventional relative quantification methods using a reference calibration curve. HPLC systems only require a standard to assess functionality of the instrument and provide a correction factor if necessary. An advantage of HPLC analysis, method provided herein, over spectrophotometer analysis is the reduction of matrix interference. Buffer or matrix components that interfere with the UV absorbance measurement can be separated from the analyses by HPLC methods.

In some embodiments, the disclosure provides methods for determining at least one of vector genome titer (Vg), capsid titer (Cp), and percentage vector genome copies per capsid (Vg %) of an adeno-associated virus (AAV) composition.

In some embodiments, the disclosure further provides methods for producing a pharmaceutical composition comprising isolated recombinant adeno-associated virus (rAAV) particles, comprising isolating rAAV particles from a feed comprising an impurity, determining at least one of the vector genome titer (Vg), capsid titer (Cp), and percentage vector genome copies per capsid (Vg %) of the isolated rAAV particles using a method disclosed herein, and formulating the isolated rAAV particles to produce a pharmaceutical composition. In some embodiments, the method uses UV spectrophotometry. In further embodiments, the method uses absolute quantification by UV spectrophotometry. In some embodiments, the method uses HPLC. In further embodiments, the method uses absolute quantification by HPLC.

In other embodiments, the disclosure further provides methods for producing a pharmaceutical composition comprising therapeutic proteins, such as therapeutic antibodies, comprising isolating the therapeutic protein from a feed comprising an impurity, determining the titer of the protein using a method disclosed herein, and formulating the protein to produce a pharmaceutical composition. In some embodiments, the method uses UV spectrophotometry. In further embodiments, the method uses absolute quantification by UV spectrophotometry. In some embodiments, the method uses HPLC. In further embodiments, the method uses absolute quantification by HPLC and determining $C_{molecule}$=f $Peak_{wavelength}$/(u L $\varepsilon_{wavelength}$).

In some embodiments, the disclosure further provides methods for producing a pharmaceutical unit dosage comprising isolated recombinant adeno-associated virus (rAAV) particles, comprising isolating rAAV particles from a feed comprising an impurity, determining at least one of the vector genome titer (Vg), capsid titer (Cp), and percentage vector genome copies per capsid (Vg %) of the isolated rAAV particles using a method disclosed herein, and formulating the isolated rAAV particles.

In some embodiments, the disclosure further provides methods for treating a disease or disorder in a subject in need thereof, comprising administering a therapeutically effective dose of isolated recombinant adeno-associated virus (rAAV) particles, wherein the amount of rAAV particles contained by the therapeutically effective dose has been determined using a method disclosed herein.

In some embodiments, the disclosure provides:

[1] an absolute quantification method for determining vector genome titer of an adeno-associated virus (AAV), the method comprising using high-performance liquid chromatography (HPLC) and the equation Vg=f $K_{DNA}$ ($Peak_{260}$−α $Peak_{280}$)/(u L);

[2] the method according to [1], wherein the AAV is non-denatured;

[3] the method according to [1], wherein the AAV is denatured;

[4] the method according to [1], wherein the HPLC is SEC-HPLC;

[5] the method according to [1], wherein the HPLC is IE-HPLC;

[6] the method according to [1], wherein the HPLC is RP-HPLC;

[7] the method according to [1], wherein the HPLC is affinity chromatography;

[8] HPLC equipment configured to perform the method according to any one of [1]-[7] [9]

[9] the HPLC equipment according to [8], comprising storage and one or more processors;

[10] an absolute quantification method for determining capsid titer of an adeno-associated virus (AAV), the method comprising using high-performance liquid chromatography and the equation Cp=f $K_{protein}$ ($Peak_{280}$−$Peak_{260}$/β)/(u L);

[11] the method according to [10], wherein the AAV is non-denatured;

[12] the method according to [10], wherein the AAV is denatured;

[13] the method according to [10], wherein the HPLC is SEC-HPLC;

[14] the method according to [10], wherein the HPLC is IE-HPLC;

[15] the method according to [10], wherein the HPLC is RP-HPLC;

[16] the method according to [10], wherein the HPLC is affinity chromatography;

[17] HPLC equipment configured to perform the method according to any one of [10]-[16];

[18] the HPLC equipment according to [17], comprising storage and one or more processors;

[19] an absolute quantification method for determining concentration of a molecule, the method comprising using high-performance liquid chromatography (HPLC) and the equation $C_{molecule}$=f $Peak_{wavelength}$/(u L $\varepsilon_{wavelength}$);

[20] the method according to [19], wherein the molecule is non-denatured;

[21] the method according to [19], wherein the molecule is denatured;

[22] the method according to [19], wherein the HPLC is SEC-HPLC;

[23] the method according to [19], wherein the HPLC is IE-HPLC;

[24] the method according to [19], wherein the HPLC is RP-HPLC;

[25] the method according to [19], wherein the HPLC is affinity chromatography;

[26] HPLC equipment configured to perform the method according to any one of [19]-[25];

[27] the HPLC equipment according to [26], comprising storage and one or more processors;

[28] a spectrophotometry method for determining vector genome titer (Vg) of an adeno-associated virus (AAV) composition, the method comprising using spectrophotometry and the equation $$Vg\ (GC/\text{mL}) = \frac{(A_{260} - \alpha A_{280})}{\varepsilon_{DNA260}\ (1 - \alpha/\beta)\ \text{L}};$$

[29] a spectrophotometry method for determining capsid titer (Cp) of an adeno-associated virus (AAV) composition, the method comprising using spectrophotometry and the equation $$Cp\ (\text{capsid/mL}) = \frac{(A_{280} - A_{260}/\beta)}{\varepsilon_{protein280}\ (1 - \alpha/\beta)\ \text{L}};$$

[30] a spectrophotometry method for determining capsid titer (Cp) of an adeno-associated virus (AAV) composition, the method comprising using spectrophotometry and the equation $$\text{Capsid titer} = m(A_{214\ AAV} - K(A_{260\ AAV} - 0.590A_{280\ AAV})) - b;$$

[31] a spectrophotometry method for determining percentage vector genome copies per capsid (Vg %) of an adeno-associated virus (AAV) composition, the method comprising using spectrophotometry and the equation $$Vg\ \% = \frac{\beta\ \varepsilon_{protein}\ (A_{260}/A_{280} - \alpha)}{\varepsilon_{DNA}\ (\beta - A_{260}/A_{280})};$$

[32] a slope spectroscopy method for determining vector genome titer (Vg) of an adeno-associated virus (AAV) composition, the method comprising using slope spectroscopy and the equation Vg=$K_{DNA}$ $S_{DNA}$, wherein $$K_{DNA} = \frac{1}{\varepsilon_{DNA260}\ (1 - \alpha/\beta)}$$

and the $S_{DNA}$ slope is obtained from linear regression analysis of ($A_{260}$−α $A_{280}$) on path length L;

[33] a slope spectroscopy method for determining capsid titer (Cp) of an adeno-associated virus (AAV) composition, the method comprising using slope spectroscopy and the equation $Cp=K_{protein} S_{protein}$ wherein $$K_{protein} = \frac{1}{\varepsilon_{protein280}\left(1-\alpha/\beta\right)}$$

and the $S_{protein}$ slope is obtained from linear regression analysis of ($A_{280}$−$A_{260}$/β) on path length L;

[34] a slope spectroscopy method for determining percentage vector genome copies per capsid (Vg %) of an adeno-associated virus (AAV) composition, the method comprising using slope spectroscopy and the equation $$Vg\ \%=K_{DNA}S_{DNA}/K_{protein}S_{protein}$$

wherein $$K_{DNA} = \frac{1}{\varepsilon_{DNA260}\left(1-\alpha/\beta\right)},\ K_{protein} = \frac{1}{\varepsilon_{protein280}\left(1-\alpha/\beta\right)},$$

and the $S_{DNA}$ and $S_{protein}$ slopes are obtained from linear regression analysis;

[35] the method according to any one of to [34], the method comprising using high-performance liquid chromatography;

[36] the method according to [35], wherein the AAV is non-denatured;

[37] the method according to [35], wherein the AAV is denatured;

[38] the method according to [35], wherein the HPLC is SEC-HPLC;

[39] the method according to [35], wherein the HPLC is IE-HPLC;

[40] the method according to [35], wherein the HPLC is RP-HPLC;

[41] the method according to [35], wherein the HPLC is affinity chromatography;

[42] HPLC equipment configured to perform the method according to any one of [35]-[41];

[43] the HPLC equipment according to [42], comprising storage and one or more processors;

[44] a method for producing a pharmaceutical composition comprising isolated recombinant adeno-associated virus (rAAV) particles, comprising:

(a) isolating rAAV particles from a feed comprising an impurity by one or more of centrifugation, depth filtration, tangential flow filtration, ultrafiltration, affinity chromatography, size exclusion chromatography, ion exchange chromatography, and hydrophobic interaction chromatography, (b) determining at least one of the genome titer (Vg), capsid titer (Cp), and percentage vector genome copies per capsid (Vg %) of the isolated rAAV particles using a method according to any one of [1] to [7], to [16], and [28] to [43], and (c) formulating the isolated rAAV particles to produce a pharmaceutical composition;

[45] a method for producing a pharmaceutical unit dosage comprising isolated recombinant adeno-associated virus (rAAV) particles, comprising:

(a) isolating rAAV particles from a feed comprising an impurity by one or more of centrifugation, depth filtration, tangential flow filtration, ultrafiltration, affinity chromatography, size exclusion chromatography, ion exchange chromatography, and hydrophobic interaction chromatography, (b) determining at least one of the genome titer (Vg), capsid titer (Cp), and percentage vector genome copies per capsid (Vg %) of the isolated rAAV particles using a method according to any one of [1] to [7], to [16], and [28] to [43], and (c) formulating the isolated rAAV particles; or

[46] A method of treating a disease or disorder in a subject in need thereof, comprising administering to the subject a therapeutically effective dose of isolated recombinant adeno-associated virus (rAAV) particles, wherein the amount of rAAV particles contained by the therapeutically effective dose has been determined using a method according to any one of [1] to [7], to [16], and [28] to [43].

[47] A method of characterizing a composition comprising isolated AAV particles, comprising a) determining the absorbance of a composition comprising the AAV particles at least at 260 nm and at 280 nm, and b) calculating the genome content (Vg), capsid content (Cp), or the percentage vector genome copies per capsid (Vg %) applying the Beer-Lambert law;

[48] the method of [47], wherein the calculating uses an extinction coefficient that is specific for the genome of the isolated AAV particles;

[49] the method of [47], wherein the calculating uses an extinction coefficient that is specific for the capsid composition of the isolated AAV particles;

[50] the method of [47], wherein the calculating uses extinction coefficients that is specific for the genome of the isolated AAV particles and for the capsid composition of the isolated AAV particles. I

[51] the method of any one of [48]-[50], wherein the extinction coefficient that is specific for the genome of the isolated AAV particles and/or for the capsid composition of the isolated AAV is a theoretical extinction coefficient;

[52] the method of any one of [48]-[50], wherein the extinction coefficient that is specific for the genome of the isolated AAV particles and/or for the capsid composition of the isolated AAV is experimentally determined;

[53] the method of any one of [47]-[52], wherein the method further comprises determining the extinction coefficient that is specific for the genome of the isolated AAV particles;

[54] the method of any one of [47]-[52], wherein the method further comprises determining the extinction coefficient that is specific for the capsid composition of the isolated AAV;

[55] the method of any one of [47]-[52], wherein, the method further comprises determining the extinction coefficient that is specific for the genome of the isolated AAV particles and for the capsid composition of the isolated AAV;

[56] the method of any one of [47]-[55], wherein the method comprises calculating the genome content (Vg) of the composition comprising isolated AAV particles;

[57] the method of any one of [47]-[55], wherein the method comprises calculating the capsid content (Cp) of the composition comprising isolated AAV particles;

[58] the method of any one of [47]-[55], wherein the method comprises calculating the percentage vector genome copies per capsid (Vg %) of the composition comprising isolated AAV particles;

[59] the method of any one of [47]-[58], wherein the AAV particles are recombinant AAV particles;

[60] the method of any one of [47]-[59], wherein the method further comprises determining the absorbance of the composition at an additional wavelength suitable for baseline correction;

[61] the method of [60], wherein the additional wavelength suitable for baseline correction is a wavelength between about 320 and about 400 nm;

[62] the method of [61], wherein the additional wavelength suitable for baseline correction is 340 nm;

[63] the method of [60], wherein the additional wavelength suitable for baseline correction is 214 nm;

[64] the method of any one of [47]-[63], wherein the isolated AAV particles are not denatured;

[65] the method of any one of [47]-[63], wherein the isolated AAV particles are denatured;

[66] the method of any one of [47]-[65], wherein the method is an absolute quantification method that does not use a calibration curve;

[67] the method of any one of [47]-[66], wherein the method comprises determining the absorbance of the composition comprising the AAV particles at least at 260 nm and at 280 nm, and calculating the genome content (Vg) applying the Beer-Lambert law, wherein the calculating uses extinction coefficients that are specific for the genome of the isolated AAV particles, and wherein the AAV particles are not denatured;

[68] the method of [67], wherein the AAV particles are recombinant AAV particles;

[69] the method of any one of [47]-[66], wherein the method comprises determining the absorbance of the composition comprising the AAV particles at least at 260 nm and at 280 nm, and calculating the genome content (Vg) applying the Beer-Lambert law, wherein the calculating uses extinction coefficients that are specific for the genome of the isolated AAV particles and for the capsid composition of the isolated AAV, and wherein the AAV particles are not denatured;

[70] the method of [69], wherein the AAV particles are recombinant AAV particles;

[71] the method of any one of [47]-[66], wherein the method comprises determining the absorbance of the composition comprising the AAV particles at least at 260 nm and at 280 nm, and calculating the capsid content (Cp) applying the Beer-Lambert law, wherein the calculating uses extinction coefficients that are specific for the capsid of the isolated AAV particles, and wherein the AAV particles are not denatured;

[72] the method of [71], wherein the AAV particles are recombinant AAV particles;

[73] the method of any one of [47]-[66], wherein the method comprises determining the absorbance of the composition comprising the AAV particles at least at 260 nm and at 280 nm, and calculating the capsid content (Cp) applying the Beer-Lambert law, wherein the calculating uses extinction coefficients that are specific for the genome of the isolated AAV particles and for the capsid composition of the isolated AAV, and wherein the AAV particles are not denatured;

[74] the method of [73], wherein the AAV particles are recombinant AAV particles;

[75] the method of any one of [47]-[66], wherein the method comprises determining the absorbance of the composition comprising the AAV particles at least at 260 nm and at 280 nm, and calculating the percentage vector genome copies per capsid (Vg %) applying the Beer-Lambert law, wherein the calculating uses extinction coefficients that are specific for the genome of the isolated AAV particles, and wherein the AAV particles are not denatured;

[76] the method of [75], wherein the AAV particles are recombinant AAV particles;

[77] the method of any one of [47]-[66], wherein the comprises determining the absorbance of the composition comprising the AAV particles at least at 260 nm and at 280 nm, and calculating the percentage vector genome copies per capsid (Vg %) applying the Beer-Lambert law, wherein the calculating uses extinction coefficients that are specific for the genome of the isolated AAV particles and for the capsid composition of the isolated AAV, and wherein the AAV particles are not denatured;

[78] the method of [77], wherein the AAV particles are recombinant AAV particles;

[79] the method of any one of [47]-[66], wherein genome content (Vg) is expressed in GC/mL (genome copy per mL), and applying the Beer-Lambert law to calculate genome content (Vg) comprises using the following equation $$Vg\ (GC/\text{mL}) = \frac{(A_{260} - \alpha A_{280})}{\varepsilon_{DNA260}\ (1 - \alpha/\beta)\ \text{L}},$$

wherein A=Absorbance; ε=Extinction Coefficient (Molar absorptivity); C=Sample Concentration; L=Path length, $\alpha=\varepsilon_{protein260}/\varepsilon_{protein280}$, $\beta=\varepsilon_{DNA260}/\varepsilon_{DNA280}$;

[80] the method of any one of [47]-[66], wherein capsid content (Cp) is expressed as capsid/mL, and applying the Beer-Lambert law to calculate genome content (Vg) comprises using the following equation $$Cp\ (\text{capsid/mL}) = \frac{(A280 - A260/\beta)}{\varepsilon_{protein280}\ (1 - \alpha/\beta)\ L},$$

wherein A=Absorbance; ε=Extinction Coefficient (Molar absorptivity); C=Sample Concentration; L=Path length, $\alpha=\varepsilon_{protein260}/\varepsilon_{protein280}$, $\beta=\varepsilon_{DNA260}/\varepsilon_{DNA280}$;

[81] the method of any one of [47]-[66], wherein applying the Beer-Lambert law to calculate the percentage vector genome copies per capsid (Vg %) comprises using the following equations $$Vg\ (GC/\text{mL}) = \frac{(A260 - \alpha \text{A}280)}{\varepsilon_{DNA260}(1 - \alpha/\beta)\ L},$$

$$Cp\ (\text{capsid/mL}) = \frac{(A280 - A260/\beta)}{\varepsilon_{protein280}(1 - \alpha/\beta)\ L},$$

and $$Vg\ \% = Vg/Cp$$

wherein A=Absorbance; ε=Extinction Coefficient (Molar absorptivity); C=Sample Concentration; L=Path length, $\alpha=\varepsilon_{protein260}/\varepsilon_{protein280}$, $\beta=\varepsilon_{DNA260}/\varepsilon_{DNA280}$;

[82] the method of any one of [47]-[66], wherein applying the Beer-Lambert law to calculate the percentage vector genome copies per capsid (Vg %) comprises using the following equation $$Vg\ \% = \frac{\beta\ \varepsilon_{protein}\ (A_{260}/A_{280} - \alpha)}{\varepsilon_{DNA}\ (\beta - A_{260}/A_{280})}$$

on experimental data obtained using standards with known Vg % to establish the correlation of Vg % and $A_{260}/A_{280}$, and using the correlation curve to determine the Vg % of a sample], wherein A=Absorbance; ε=Extinction Coefficient (Molar absorptivity); $\alpha=\varepsilon_{protein260}/\varepsilon_{protein280}$, $\beta=\varepsilon_{DNA260}/\varepsilon_{DNA280}$;

[83] the method of [82], wherein the method disclosed herein further comprises adjusting α, β, $\varepsilon_{protein}$ and EDNA by fitting experimental data obtained using standards with known Vg %;

[84] the method of any one of [79]-[83], wherein the EDNA is specific for the genome of the isolated AAV particles;

[85] the method of any one of [79]-[83], wherein the $\varepsilon_{protein}$ is specific for the for the capsid composition of the isolated AAV;

[86] the method of any one of [79]-[83], wherein the EDNA is specific for the genome of the isolated AAV particles, and $\varepsilon_{protein}$ is specific for the for the capsid composition of the isolated AAV;

[87] the method of any one of [79]-[86], wherein the isolated AAV particles are not denatured;

[88] the method of [79], wherein the EDNA is specific for the genome of the isolated AAV particles, $\varepsilon_{protein}$ is specific for the for the capsid composition of the isolated AAV, and the isolated AAV particles are non-denatured;

[89] the method of any one of [79]-[88], wherein the method is an absolute quantification method that does not use a calibration curve;

[90] the method of any one of [79]-[89], wherein the extinction coefficients that is specific for the genome of the isolated AAV particles and/or for the capsid composition of the isolated AAV is a theoretical extinction coefficient;

[91] the method of any one of [79]-[90], wherein the extinction coefficients that is specific for the genome of the isolated AAV particles and/or for the capsid composition of the isolated AAV is experimentally determined;

[92] the method of any one of [79]-[91], wherein the method further comprises determining the extinction coefficient that is specific for the genome of the isolated AAV particles;

[93] the method of any one of [79]-[91], wherein the method further comprises determining the extinction coefficient that is specific for the capsid composition of the isolated AAV;

[94] the method of any one of [79]-[91], wherein the method further comprises determining the extinction coefficient that is specific for the genome of the isolated AAV particles and for the capsid composition of the isolated AAV;

[95] the method of any one of [79]-[94], wherein the AAV particles are recombinant AAV particles;

[96] the method of any one of [47]-[66], wherein the method comprises determining the absorbance of the composition comprising the AAV particles at least at 260 nm and at 280 nm using slope spectroscopy, and calculating the genome content (Vg), capsid content (Cp), or the percentage vector genome copies per capsid (Vg %) applying the Beer-Lambert law;

[97] the method of [96], wherein the calculating uses an extinction coefficient that is specific for the genome of the isolated AAV particles;

[98] the method of [96], wherein the calculating uses an extinction coefficient that is specific for the capsid composition of the isolated AAV particles;

[99] the method of [96], wherein the calculating uses extinction coefficients that is specific for the genome of the isolated AAV particles and for the capsid composition of the isolated AAV particles;

[100] the method of any one of [96]-[99], wherein the extinction coefficient that is specific for the genome of the isolated AAV particles and/or for the capsid composition of the isolated AAV is a theoretical extinction coefficient;

[101] the method of any one of [96]-[99], wherein the extinction coefficient that is specific for the genome of the isolated AAV particles and/or for the capsid composition of the isolated AAV is experimentally determined;

[102] the method of any one of [96]-[101], wherein the method further comprises determining the extinction coefficient that is specific for the genome of the isolated AAV particles;

[103] the method of any one of [96]-[101], wherein the method further comprises determining the extinction coefficient that is specific for the capsid composition of the isolated AAV;

[104] the method of any one of [96]-[101], wherein the method further comprises determining the extinction coefficient that is specific for the genome of the isolated AAV particles and for the capsid composition of the isolated AAV;

[105] the method of any one of [96]-[104], wherein the method further comprises determining the absorbance of the composition at an additional wavelength suitable for baseline correction;

[106] the method of [105], wherein the additional wavelength suitable for baseline correction is a wavelength between about 320 and about 400 nm;

[107] the method of [106], wherein the additional wavelength suitable for baseline correction is 340 nm;

[108] the method of [105], wherein the additional wavelength suitable for baseline correction is 214 nm;

[109] the method of any one of [96]-[108], wherein the isolated AAV particles are not denatured;

[110] the method of any one of [96]-[108], wherein the isolated AAV particles are denatured;

[111] the method of any one of [96]-[110], wherein the a method of characterizing a composition comprising isolated AAV particles described herein is an absolute quantification method that does not use a calibration curve;

[112] the method of any one of [96]-[111], wherein the method comprises calculating the genome content (Vg) of the composition comprising isolated AAV particles;

[113] the method of any one of [96]-[111], wherein the method comprises calculating the capsid content (Cp) of the composition comprising isolated AAV particles;

[114] the method of any one of [96]-[111], wherein the method comprises calculating the percentage vector genome copies per capsid (Vg %) of the composition comprising isolated AAV particles;

[115] the method of any one of [96]-[114], wherein the AAV particles are recombinant AAV particles;

[116] the method of any one of [47]-[66], wherein applying the Beer-Lambert law to calculate genome content (Vg) comprises using the following equation $$Vg=K_{DNA}S_{DNA},$$

wherein $$K_{DNA}=\frac{1}{\varepsilon_{DNA260}\left(1-\alpha/\beta\right)},$$

$S_{DNA}$ is the slope of ($A_{260}-\alpha\ A_{280}$) plotted against the path length L, and A=Absorbance; ε=Extinction Coefficient (Molar absorptivity); $\alpha=\varepsilon_{protein260}/\varepsilon_{protein280}$, and $\beta=\varepsilon_{DNA260}/\varepsilon_{DNA280}$;

[117] the method of any one of [47]-[66], wherein applying the Beer-Lambert law to calculate capsid content (Cp) comprises using the following equation $$Cp=K_{protein}S_{protein},$$

wherein $$K_{protein}=\frac{1}{\varepsilon_{protein280}\left(1-\alpha/\beta\right)},$$

$S_{protein}$ is the slope of ($A_{280}-A_{260}/\beta$) plotted against the path length L, and A=Absorbance; ε=Extinction Coefficient (Molar absorptivity); $\alpha=\varepsilon_{protein260}/\varepsilon_{protein280}$, and $\beta=\varepsilon_{DNA260}/\varepsilon_{DNA280}$;

[118] the method of any one of [47]-[66], wherein applying the Beer-Lambert law to calculate the percentage vector genome copies per capsid (Vg %) comprises using the following equation $$Vg\ \%=Vg/Cp,$$

wherein $$Vg=K_{DNA}S_{DNA},$$

$$Cp=K_{protein}S_{protein},$$

$$K_{DNA}=\frac{1}{\varepsilon_{DNA260}\left(1-\alpha/\beta\right)},$$

$$K_{protein}=\frac{1}{\varepsilon_{protein280}\left(1-\alpha/\beta\right)}$$

$S_{DNA}$ is the slope of ($A_{260}-\alpha\ A_{280}$) plotted against the path length L, $S_{protein}$ is the slope of ($A_{280}-A_{260}/\beta$) plotted against the path length L, and A=Absorbance; ε=Extinction Coefficient (Molar absorptivity); $\alpha=\varepsilon_{protein260}/\varepsilon_{protein280}$, and $\beta=\varepsilon_{DNA260}/\varepsilon_{DNA280}$;

[119] the method of any one of [116]-[118], wherein the EDNA is specific for the genome of the isolated AAV particles;

[120] the method of any one of [116]-[118], wherein the $\varepsilon_{protein}$ is specific for the for the capsid composition of the isolated AAV;

[121] the method of any one of [116]-[118], wherein the EDNA is specific for the genome of the isolated AAV particles, and $\varepsilon_{protein}$ is specific for the for the capsid composition of the isolated AAV;

[122] the method of any one of [116]-[121], wherein the isolated AAV particles are not denatured;

[123] the method of any one of [116]-[118], wherein the EDNA is specific for the genome of the isolated AAV particles, $\varepsilon_{protein}$ is specific for the for the capsid composition of the isolated AAV, and the isolated AAV particles are non-denatured;

[124] the method of any one of [116]-[123], wherein the method is an absolute quantification method that does not use a calibration curve;

[125] the method of any one of [116]-[124], wherein the extinction coefficients that is specific for the genome of the isolated AAV particles and/or for the capsid composition of the isolated AAV is a theoretical extinction coefficient;

[126] the method of any one of [116]-[124], wherein the extinction coefficients that is specific for the genome of the isolated AAV particles and/or for the capsid composition of the isolated AAV is experimentally determined;

[127] the method of any one of [116]-[126], wherein the method further comprises determining the extinction coefficient that is specific for the genome of the isolated AAV particles;

[128] the method of any one of [116]-[127], wherein the method further comprises determining the extinction coefficient that is specific for the capsid composition of the isolated AAV;

[129] the method of any one of [116]-[128], wherein the method further comprises determining the extinction coefficient that is specific for the genome of the isolated AAV particles and for the capsid composition of the isolated AAV;

[130] the method of any one of [116]-[129], wherein the AAV particles are recombinant AAV particles;

[131] the method of any one of [47]-[59], wherein the method comprises analyzing the composition on an HPLC system with UV detection to determine the peak absorbance corresponding to the AAV particles at least at 260 nm and at 280 nm, and calculating the genome content (Vg), capsid content (Cp), or the percentage vector genome copies per capsid (Vg %) applying the Beer-Lambert law;

[132] the method of [131], wherein the HPLC system is a size exclusion high performance chromatography (SEC-HPLC) system, ion exchange high performance chromatography (IE-HPLC) system, or an affinity and reversed phase high performance chromatography (RP-HPLC) system;

[133] the method of [131], wherein the HPLC system is a SEC-HPLC system;

[134] the method of any one of [131]-[133], wherein the calculating uses an extinction coefficient that is specific for the genome of the isolated AAV particles;

[135] the method of any one of [131]-[133], wherein the calculating uses an extinction coefficient that is specific for the capsid composition of the isolated AAV particles;

[136] the method of any one of [131]-[133], wherein the calculating uses extinction coefficients that is specific for the genome of the isolated AAV particles and for the capsid composition of the isolated AAV particles;

[137] the method of any one of [131]-[136], wherein the extinction coefficient that is specific for the genome of the isolated AAV particles and/or for the capsid composition of the isolated AAV is a theoretical extinction coefficient;

[138] the method of any one of [131]-[136], wherein the extinction coefficient that is specific for the genome of the isolated AAV particles and/or for the capsid composition of the isolated AAV is experimentally determined;

[19] the method of any one of [131]-[138], wherein the method further comprises determining the extinction coefficient that is specific for the genome of the isolated AAV particles;

[140] the method of any one of [131]-[138], wherein the method further comprises determining the extinction coefficient that is specific for the capsid composition of the isolated AAV;

[141] the method of any one of [131]-[138], wherein the method further comprises determining the extinction coefficient that is specific for the genome of the isolated AAV particles and for the capsid composition of the isolated AAV;

[142] the method of any one of [131]-[141], wherein the method further comprises determining the absorbance of the composition at an additional wavelength suitable for baseline correction;

[143] The method [142], wherein the additional wavelength suitable for baseline correction is a wavelength between about 320 and about 400 nm;

[144] the method of [143], wherein the additional wavelength suitable for baseline correction is 340 nm;

[145] the method of [142], wherein the additional wavelength suitable for baseline correction is 214 nm;

[146] the method of any one of [131]-[145], wherein the isolated AAV particles are not denatured;

[147] the method of any one of [131]-[145], wherein the isolated AAV particles are denatured;

[148] the method of any one of [131]-[147], wherein the a method of characterizing a composition comprising isolated AAV particles described herein is an absolute quantification method that does not use a calibration curve;

[149] the method of any one of [131]-[148], wherein the method comprises calculating the genome content (Vg) of the composition comprising isolated AAV particles;

[150] the method of any one of [131]-[148], wherein the method comprises calculating the capsid content (Cp) of the composition comprising isolated AAV particles;

[151] the method of any one of [131]-[148], wherein the method comprises calculating the percentage vector genome copies per capsid (Vg %) of the composition comprising isolated AAV particles;

[152] the method of any one of [131]-[151], wherein the AAV particles are recombinant AAV particles;

[153] the method of any one of [131]-[152], wherein applying the Beer-Lambert law to calculate genome content (Vg) comprises using the following equation $$Vg=fK_{DNA}(\mathrm{Peak}_{260}-\alpha\mathrm{Peak}_{280})/(uL),$$

wherein $$K_{DNA}=\frac{1}{\varepsilon_{DNA260}\left(1-\alpha/\beta\right)};$$

f=flow rate; ε=Extinction Coefficient (Molar absorptivity); $\alpha=\varepsilon_{protein260}/\varepsilon_{protein280}$, and $\beta=\varepsilon_{DNA260}/\varepsilon_{DNA280}$; u=injection volume;

[154] the method of any one of [131]-[152], wherein applying the Beer-Lambert law to calculate capsid content (Cp) comprises using the following equation $$Cp=fK_{protein}(\mathrm{Peak}_{280}-\mathrm{Peak}_{260}/\beta)/(uL),$$

wherein $$K_{protein}=\frac{1}{\varepsilon_{protein280}\left(1-\alpha/\beta\right)};$$

f=flow rate; ε=Extinction Coefficient (Molar absorptivity); $\alpha=\varepsilon_{protein260}/\varepsilon_{protein280}$, and $\beta=\varepsilon_{DNA260}/\varepsilon_{DNA280}$; u=injection volume;

[155] the method of or [154], wherein the EDNA is specific for the genome of the isolated AAV particles;

[156] the method of or [154], wherein the $\varepsilon_{protein}$ is specific for the for the capsid composition of the isolated AAV;

[157] the method of or [154], wherein the EDNA is specific for the genome of the isolated AAV particles, and $\varepsilon_{protein}$ is specific for the for the capsid composition of the isolated AAV;

[158] the method of any one of [153]-[157], wherein the method further comprises determining the extinction coefficient that is specific for the capsid composition of the isolated AAV;

[159] the method of any one of [153]-[157], wherein the method further comprises determining the extinction coefficient that is specific for the genome of the isolated AAV particles and for the capsid composition of the isolated AAV;

[160] the method of any one of [131]-[152], wherein the method comprises analyzing the composition on an HPLC system with UV detection to determine the peak absorbance corresponding to the AAV particles at least at 214 nm, 260 nm, and at 280 nm, and calculating the capsid content (Cp) applying the Beer-Lambert law;

[161] the method of any one of [131]-[152], wherein applying the Beer-Lambert law to calculate capsid content (Cp) comprises using the following equation $$\text{Capsid titer}=m(\text{Total Sample Absorbance @214 nm}-(\text{Total DNA Absorbance @ 214 nm}))-b;$$

wherein m=Slope of empty capsid linear regression

A214, A260, A280=Peak area at UV 214, 260 and 280 nm wavelengths b=y-intercept of empty calibration curve;

[162] the method of any one of [131]-[152], wherein applying the Beer-Lambert law to calculate capsid content (Cp) comprises using the following equation $$\text{Capsid titer}=(A_{214\ AAV}-K(A_{260\ AAV}-0.590A_{280\ AAV}))-b;$$

wherein m=Slope of empty capsid linear regression;

A214, A260, A280=Peak area at UV 214, 260 and 280 nm wavelengths;

K—A factor related to A214/A260 ratio of DNA; and b=y-intercept of empty calibration curve.

[163] A method of characterizing a composition comprising a two component system, comprising a) determining the absorbance of the composition comprising the two component system at least at a first and second wavelength corresponding to the peak absorbance the first and second component of the two-component system, and b) calculating the concentration of the first component and/or second component applying the Beer-Lambert law;

[164] the method of [163], wherein the two component system comprises a DNA component and a protein component;

[165] the method of [163], wherein the two component system comprises a protein component conjugated to a non-protein molecule, optionally, a small molecule drug;

[166] the method of [163], wherein the two component system comprises a virus;

[167] the method of [163], wherein the two component system comprises an antibody-drug conjugate.

[168] A method for determining the concentration ($C_{molecule}$) of a biomolecule or a small organic molecule, comprising a) determining the peak absorbance corresponding to the biomolecule or small organic molecule by analyzing the composition comprising the biomolecule or small organic molecule on an HPLC system with UV detection, and b) calculating the concentration of the biomolecule or small organic molecule using the Beer-Lambert law;

[169] the method of [168], wherein the biomolecule is an antibody, optionally, a monoclonal antibody;

[170] the method of [168] or [169], wherein the HPLC system is a size exclusion high performance chromatography (SEC-HPLC) system, ion exchange high performance chromatography (IE-HPLC) system, or an affinity and reversed phase high performance chromatography (RP-HPLC) system;

[171] the method of [170], wherein the HPLC system is a SEC-HPLC system;

[172] the method of any one of [168]-[171], wherein the method comprises using the equation:

$$C_{molecule}=Kcf\text{Peak}_{wavelength}/(uL\varepsilon_{wavelength});$$

[173] the method of any one of [168]-[172], wherein the method is an absolute quantification method that does not use a calibration curve.

[174] A method for producing a pharmaceutical composition comprising isolated recombinant AAV particles, comprising (i) isolating rAAV particles from a feed comprising an impurity by one or more of centrifugation, depth filtration, tangential flow filtration, ultrafiltration, affinity chromatography, size exclusion chromatography, ion exchange chromatography, and hydrophobic interaction chromatography, (ii) determining at least one of the genome titer (Vg), capsid titer (Cp), and percentage vector genome copies per capsid (Vg %) of the isolated rAAV particles using a method according to any one of [47]-[162], and (iii) formulating the isolated rAAV particles to produce a pharmaceutical composition;

[175] the method of [174], wherein the composition comprising isolated recombinant AAV particles is bulk drug substance;

[176] the method of [174], wherein the composition comprising isolated recombinant AAV particles is a pharmaceutical composition;

[177] the method of [174], wherein the composition comprising isolated recombinant AAV particles is a pharmaceutical unit dosage;

[178] the method of [174], wherein the at least one of Vg, Cp, and Vg % is determined after a centrifugation, depth filtration, tangential flow filtration, ultrafiltration, affinity chromatography, size exclusion chromatography, ion exchange chromatography, or hydrophobic interaction chromatography step. I

[179] the method of [174], wherein the method is used to determine at least one of Vg, Cp, and Vg % of the isolated rAAV particles following a formulation step;

[180] the method of [174], wherein the method is used to determine at least one of Vg, Cp, and Vg % of the isolated rAAV particles following a fill-finish step;

[181] the method of [174], wherein the method is used to determine at least one of Vg, Cp, and Vg % of isolated rAAV particles in a bulk drug substance.

[182] A method for treating a disease or disorder in a subject in need thereof, comprising administering to the subject a therapeutically effective dose of isolated recombinant adeno-associated virus (rAAV) particles, wherein the amount of rAAV particles contained by therapeutically effective dose has been determined using a method according to any one of [47]-[162].

Still other features and advantages of the systems and methods described herein will become more apparent from the following detailed description when read in conjunction with the accompanying drawings.

BRIEF DESCRIPTION OF THE DRAWINGS

FIG. 7 illustrates estimating average distribution of DNA within partially-full capsids based on sedimentation coefficients.

FIG. 16. Comparison of vector genome titer (GC/mL) by spectrophotometry and polymerase chain reaction (PCR) for several representative samples.

FIG. 18A shows the full to empty AAV ratios measured by AUC using interference or A280 absorbance to detect AAV particles. For AAV samples with negligible partially-full capsids, the difference between the True % Full Value and the % Full Value estimated by AUC using A280 detection is small. However, for AAV sample with significant levels of partially-full capsids, a normalization is used to determine true % full value (FIG. 18B). FIG. 18C shows the correlation between % Full values determined by a method disclosed herein (Spectrophotometry % Full) and Adjusted AUC % Full value can be used to determine the extent of the interference.

FIGS. 20A-C illustrate the results of qualification tests for reproducibility (such repeatability precision), precision (such as linearity) and range of the absolute quantification assay.

DETAILED DESCRIPTION OF EXAMPLE EMBODIMENTS

Figure 1:
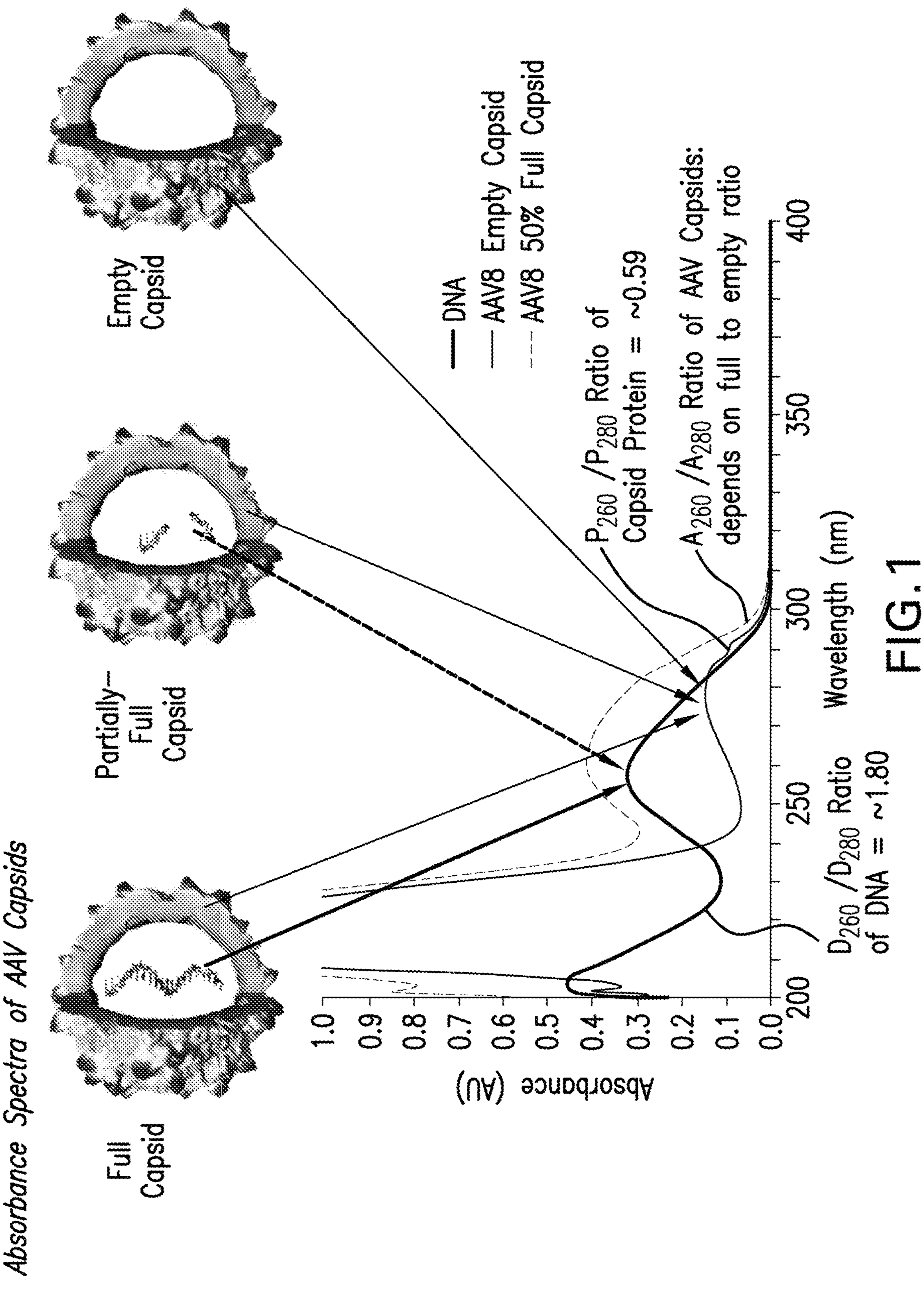
FIG. 1 illustrates an example of UV absorbance of AAV and its DNA and capsid protein components. A generic depiction of AAV particles represents full capsids containing DNA (DNA of interest, e.g., genome carrying a full transgene), partially-full capsids containing, e.g., fragments of DNA or non-transgene DNA, versus empty capsids. The Figure also depicts the relationship of each of their UV spectra from one exemplary experiment. In the representative experiment, a DNA ratio (D260/D280=~1.80) and a capsid protein ratio (P260/P280=~0.59) were determined for the sample tested.

In one aspect, described herein are spectrophotometry methods for characterizing Adeno-associated virus (AAV) preparations. In some embodiments, the methods described herein provide fast, easy, high-throughput methods with real-time capability that can be used in short turnaround time testing. They require little to no sample preparation and provide reproducible results within the same lab and between different sites. The assays provide equivalent results within the same lab and between different sites, are easy to transfer, and function appropriately to be applied to quality control laboratories.

Adeno-associated virus (AAV) is a non-enveloped virus that packages a linear single-stranded DNA genome and can be engineered to deliver DNA to target cells. AAV has been shown to be less immunogenic than other viruses. Recombinant AAV (rAAV), used as the gene delivery vector for transgenes of interest, has proven to be one of the safest strategies for gene therapies.

For many gene therapy products, dosing in both preclinical and clinical studies is based on vector genome copies (i.e., vector genome titer). AAV vector genome titer is usually determined by quantitative PCR (qPCR), digital PCR (dPCR) or droplet digital PCR (ddPCR). The requirement for a standard calibration curve, the variations in DNA amplification efficiency due to primer/probe designs and template secondary structure, as well as the presence of inhibitors, result in a large error and poor quantification by qPCR. Absolute quantification by ddPCR reduces errors associated with a calibration curve and amplification efficiency. Although significantly improved, quantification by ddPCR still can be problematic due to poor primer/probe designs and template secondary structure. Inter-laboratory reproducibility using the same primer/probe still cannot achieve ideal precision (e.g., within 10%).

Vector genome titer is usually used for dosing AAV in clinical trials. Capsid content or capsid titer also needs to be quantified and controlled. Capsid titer includes capsids with a complete designed transgene (full capsid), and capsids lacking the vector genome and therefore unable to provide a therapeutic benefit (empty capsid). AAV empty particles may contain small fragments of DNA that are not readily distinguished from completely empty capsids by analytical methods, including analytical ultracentrifugation and electron microscopy. Capsid titer can be measured using serotype-specific ELISA. However, this assay is only available for several serotypes, and there can be difficulties developing specific antibodies for chimeric serotypes. In addition, reference standards of the same serotype of AAV with known capsid titer, which is difficult to determine accurately, are needed for ELISA assays.

UV absorbance at 280 nm can be used to measure the protein concentration. Dosing of therapeutic protein products, especially mAb products, is based on the protein concentration determined by UV absorbance at 280 nm.

AAV is comprised of an icosahedral symmetric capsid made of about 60 capsid proteins (VP1, VP2 and VP3 with a ratio 1:1:10) and an encapsulated single-stranded deoxyribonucleic acid (ssDNA) about 4.7 kilobase long. Both protein and DNA components contribute to UV absorbance.

Figure 8:
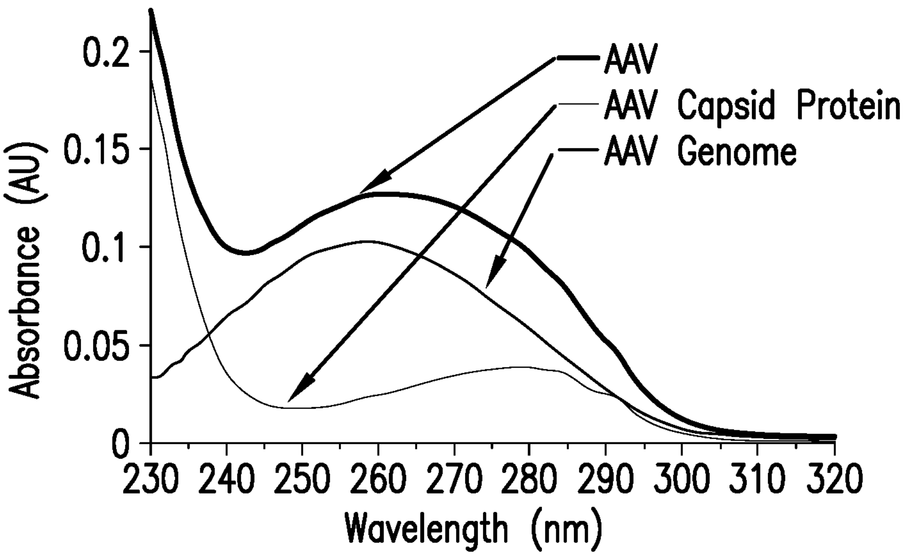
FIG. 8 illustrates a representative absorbance spectra of AAV and its DNA and capsid protein components.

FIG. 8 illustrates that the overall UV absorbance of AAV product is the sum of UV absorbance by capsid proteins and the vector genome DNA. It is known that the absorbance maximum of DNA is at 260 nm, whereas, for proteins, the maximum is at 280 nm. Since the absorbance of vector genome DNA is several times more than that of capsid proteins, the absorbance maximum of AAV vector is at 260 nm.

Sommer J M et al. (Sommer J M et al "Quantification of adeno-associated virus particles and empty capsids by optical density measurement" Mol. Ther. 7, 122-128, 2003) describes direct quantification of AAV2 vector genome titer and capsid titer using UV spectrophotometry, however lacks the ability to resolve in genome-specific or capsid-specific differences. This method purports to enable determination of AAV2 vector genome titer (Vg) and capsid titer (Cp), as well as estimating the ratio of full to empty capsids because empty capsids in AAV2 vector preparations lowers the $A_{260}/A_{280}$ ratio in a predictable manner. Vector genome titer was calculated according to $$vg/\text{ml} = \frac{4.47\times 10^{19}(A_{260} - 0.59A_{280})}{\text{MW}_{DNA}}.$$

Capsid titer was calculated indirectly according to $$\text{cp}/vg = \text{MW}_{DNA}\times\frac{1.76\times 10^{-6}(1.80 - A_{260}/A_{280})}{A_{260}/A_{280} - 0.59}.$$

The results determined by UV spectrophotometry were in general agreement with those determined by qPCR and capsid ELISA. In some embodiments, the method comprises AAV denaturation, e.g. for some serotypes, under the conditions of 0.1% SDS and 10 min at 75° C. Denaturation of AAV was used to prevent light scattering caused by intact AAV particles. However, applying this method to general AAV products, including different serotypes of AAVs such as AAV8 and AAV9, are not so successful, especially with certain types of formulation buffers, which generate high absorbance interference upon reaction with SDS. In addition, as discussed below, the present applicant found that light scattering caused by intact AAV vectors, including AAV8 and AAV9, was negligible (see FIG. 2).

The present disclosure describes by way of example and without limitation a UV spectrophotometry method under native (or non-denaturing) conditions to measure GC titer and capsid titer of AAV vectors. In certain examples, a set of equations with pre-defined parameters can be used, including theoretical or experimentally determined constants, and/or extinction coefficients for vector genome DNA and capsid proteins. This set of equations is applicable, for example, to both denaturing and non-denaturing conditions to determine vector GC titer and capsid titer, as well as full to empty capsid ratio. Increased sensitivity can be obtained under non-denaturing conditions, since AAV under non-denaturing conditions with single-stranded DNA (ssDNA) has a higher UV extinction coefficient (0.027 mL AU/ug cm) than denatured AAV, in which the ssDNA anneals to form double-stranded DNA with an extinction coefficient of 0.020 mL AU/ug cm. Because of the increased sensitivity, the lack of additional sample treatment steps, and the absence of light scattering, the UV spectrophotometry analysis performed under non-denaturing conditions provides a more precise and accurate determination of vector titer and capsid titer, and is more easily carried out in a quality control laboratory.

In addition to UV absorbance measurement, HPLC with UV detection at 260 nm and 280 nm can also be used to measure the absolute vector genome and capsid titer. Equations to calculate vector genome and capsid titer using HPLC peak areas are described herein. The vector genome titer and capsid titer are directly calculated from peak areas at 260 nm and 280 nm. Quantification by HPLC using this method is absolute and no calibration curve is needed. Both UV absorbance and HPLC methods provide an easier, faster, more precise and reproducible means to determine the vector genome titer and capsid titer than PCR methods (e.g. qPCR, dPCR and ddPCR).

The absolute HPLC quantification method is applicable to protein, DNA, biopolymers and small molecules. Conventional HPLC quantification is relative and utilize standards to generate calibration curve. Using the non-limiting, example systems and methods described herein, the HPLC UV detector is operated in a manner similar to a spectrophotometer. No calibration curve is needed in quantitative analysis. The HPLC method described here is an absolute quantification method, in comparison with conventional relative quantification methods using a reference calibration curve. HPLC systems only require a standard to assess functionality of the instrument and provide a correction factor if necessary. Similar molecular properties to the analyte molecules may not be required for the standard. Instead, any molecules with a known concentration and compatible to HPLC analysis can be used as the standard. An advantage of the HPLC analysis method described herein over spectrophotometer analysis is the reduction of matrix interference. Buffer or matrix components that interfere with the UV absorbance measurement can be separated from the analyses by HPLC methods.

The present disclosure is described in the context of example embodiments. However, the scope of the disclosure is not limited to the particular embodiments described herein. Rather, the description merely serves to illustrate the principles and characteristics of the present disclosure. Those skilled in the art will recognize that various modifications and refinements may be made without departing from the spirit and scope of the disclosure.

Definitions

Unless defined otherwise, all technical and scientific terms used herein have the same meaning as commonly understood by one of ordinary skill in the art to which this disclosure is related. To facilitate an understanding of the disclosed methods, a number of terms and phrases are defined below.

"About" modifying, for example, the quantity of an ingredient in the compositions, concentration of an filter surface area ratios, flux through filters, turbidity, rAAV particle yield, viable cell density, total cell viability, feed volume, salt concentration, and like values, and ranges thereof, employed in the methods provided herein, refers to variation in the numerical quantity that can occur, for example, through typical measuring and handling procedures used for making concentrates or use solutions; through inadvertent error in these procedures; through differences in the manufacture, source, or purity of the ingredients employed to make the compositions or carry out the methods; and like considerations. Whether or not modified by the term "about" the claims include equivalents to the quantities. In some embodiments, the term "about" refers to ranges of approximately 10-20% greater than or less than the indicated number or range. In further embodiments, "about" refers to plus or minus 10% of the indicated number or range. For example, "about 10%" indicates a range of 9% to 11%.

"AAV" is an abbreviation for adeno-associated virus, and may be used to refer to the virus itself or modifications, derivatives, or pseudotypes thereof. The term covers all subtypes and both naturally occurring and recombinant forms, except where required otherwise. The abbreviation "rAAV" refers to recombinant adeno-associated virus. The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV, and modifications, derivatives, or pseudotypes thereof. "Primate AAV" refers to AAV that infect primates, "non-primate AAV" refers to AAV that infect non-primate mammals, "bovine AAV" refers to AAV that infect bovine mammals, etc.

"Recombinant", as applied to a an AAV particle means that the AAV particle is the product of one or more procedures that result in an AAV particle construct that is distinct from an AAV particle in nature.

A recombinant Adeno-associated virus particle "rAAV particle" refers to a viral particle composed of at least one AAV capsid protein and an encapsidated polynucleotide rAAV vector comprising a heterologous polynucleotide (i.e. a polynucleotide other than a wild-type AAV genome such as a transgene to be delivered to a mammalian cell). The rAAV particle may be of any AAV serotype, including any modification, derivative or pseudotype (e.g., AAV-1, AAV-2, AAV-3, AAV-4, AAV-5, AAV-6, AAV-7, AAV-8, AAV-9, or AAV-10, or derivatives/modifications/pseudotypes thereof). Such AAV serotypes and derivatives/modifications/pseudotypes, and methods of producing such serotypes/derivatives/modifications/pseudotypes are known in the art (see, e.g., Asokan et al., Mol. Ther. 20 (4): 699-708 (2012).

The rAAV particles of the disclosure may be of any serotype, or any combination of serotypes, (e.g., a population of rAAV particles that comprises two or more serotypes, e.g., comprising two or more of rAAV2, rAAV8, and rAAV9 particles). In some embodiments, the rAAV particles are rAAV1, rAAV2, rAAV3, rAAV4, rAAV5, rAAV6, rAAV7, rAAV8, rAAV9, rAAV10, or other rAAV particles, or combinations of two or more thereof). In some embodiments, the rAAV particles are rAAV2, rAAV8 or rAAV9 particles.

In some embodiments, the rAAV particles have an AAV capsid protein of a serotype selected from the group consisting of AAV-1, AAV-2, AAV-3, AAV-4, AAV-5, AAV-6, AAV-7, AAV-8, AAV-9, AAV-10, AAV-11, AAV-12, AAV-13, AAV-14, AAV-15 and AAV-16 or a derivative, modification, or pseudotype thereof. In some embodiments, the rAAV particles have an AAV capsid protein of a serotype selected from the group consisting of AAV-1, AAV-4, AAV-5, and AAV-8 or a derivative, modification, or pseudotype thereof. In some embodiments, the rAAV particles have an AAV-8 or AAV-9 capsid serotype or a derivative, modification, or pseudotype thereof.

Ultraviolet spectrophotometry or UV spectrophotometry (also referred to as UV spectroscopy) refers to absorption spectroscopy in which light of ultra-violet range (200-400 nm) is absorbed by a molecule. Use of a UV spectrophotometer follows the principles of Beer-Lambert Law. In general, whenever a beam of monochromatic light is passed through a solution with an absorbing substance, the decreasing rate of the radiation intensity along with the thickness of the absorbing solution is actually proportional to the concentration of the solution and the incident radiation.

High-performance liquid chromatography (HPLC) refers to a form of column chromatography that pumps a sample mixture or analyte in a solvent (known as the mobile phase) at high pressure through a column with chromatographic packing material or a matrix (stationary phase). The sample is carried by a moving carrier gas stream, e.g. helium or nitrogen. Stationary phase columns are comprised of chromatography media or resin which interacts with the mobile phase mixture or analyte. Although manual injection of samples is still possible, typical HPLC systems are fully automated and controlled by computer. An injector or autosampler, may be employed, connected to an apparatus to house the column hardware, which is further connected to a detector. Types of HPLC are well-known in the art, including but not limited to reverse-phase HPLC (RP-HPLC), Size-exclusion chromatography HPLC (SEC-HPLC), ion-exchange chromatography HPLC (IE-HPLC), affinity chromatography HPLC, and aqueous normal-phase chromatography HPLC (ANP-HPLC).

The term "impurity" or "contaminant" refers to any foreign or objectionable molecule, including a biological macromolecule such as DNA, RNA, one or more host cell proteins, endotoxins, lipids and one or more additives which may be present in a sample containing the rAAV particles that are being separated from one or more of the foreign or objectionable molecules using a disclosed method. Additionally, such impurity may include any reagent which is used in a step which may occur prior to one or more of the disclosed methods. An impurity may be soluble or insoluble in nature. Insoluble impurities include any undesirable or objectionable entity present in a sample containing rAAV particles, where the entity is a suspended particle or a solid. Exemplary insoluble impurities include without limitation, whole cells, cell fragments and cell debris. Soluble impurities include any undesirable or objectionable entity present in a sample containing rAAV particles where the entity is not an insoluble impurity. Exemplary soluble impurities include without limitation, host cell proteins, DNA, RNA, lipids viruses, endotoxins, and cell culture media components.

The term "feed" refers to a source of rAAV particles that is loaded onto, passed through, or applied to a filter or chromatographic matrix. Feeds encompassed by the disclosure include production culture harvests, and materials isolated from previous chromatographic steps encompassed by the disclosed methods whether the material was present as flow-through from the previous step, bound and eluted in the previous step, present in the void volume of the previous step or present in any fraction obtained during the purification of rAAV particles. Such feeds may include one or more contaminants. In some embodiments, the feed containing rAAV particles further comprises production culture contaminants such as damaged rAAV particles, host cell contaminants, helper virus contaminants, and/or cell culture contaminants. In some embodiments, the host cell contaminants comprise host cell DNA, plasmids, or host cell protein. In additional embodiments, the helper virus contaminants comprise adenovirus particles, adenovirus DNA, or adenovirus proteins. In some embodiments, the cell culture contaminants comprise media components, serum albumin, or other serum proteins. In additional embodiments, the cell culture contaminants comprise media components.

The terms "purifying", "purification", "separate", "separating", "separation", "isolate", "isolating", or "isolation", as used herein, refer to increasing the degree of purity of rAAV particles from a sample comprising the target molecule and one or more impurities. Typically, the degree of purity of the target molecule is increased by removing (completely or partially) at least one impurity from the sample. In some embodiments, the degree of purity of the rAAV in a sample is increased by removing (completely or partially) one or more impurities from the sample by using a method described herein.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Where embodiments of the disclosure are described in terms of a Markush group or other grouping of alternatives, the disclosed method encompasses not only the entire group listed as a whole, but also each member of the group individually and all possible subgroups of the main group, and also the main group absent one or more of the group members. The disclosed methods also envisage the explicit exclusion of one or more of any of the group members in the disclosed methods.

Advantages of the Methods

In one aspect, described herein are spectrophotometry methods for characterizing Adeno-associated virus (AAV) preparations using the Beer-Lambert law. The inventors have surprisingly found that the actual extinction coefficients of the DNA and capsid protein components of AAV particles differ significantly from the general DNA and protein extinction coefficients known in the art. For example, without being bound by any theory, the extinction coefficient of the DNA encompassed within an intact AAV particle appears to be influenced by the structure of the DNA and by interactions between the DNA and capsid proteins. Furthermore, the extinction coefficients of different DNA genomes of AAV particles were found to differ from each other. The inventors further found significant variations among the extinction coefficient of the capsid component of different AAV serotypes. The inventors have applied these findings to develop novel methods for determining the genome content (Vg), capsid content (Cp), or the percentage vector genome copies per capsid (Vg %). Without being bound by any theory, by using in some embodiments of methods disclosed herein extinction coefficients specific for the genome and/or capsid of a particular AAV preparation, the methods disclosed herein are capable of determining genome content (Vg), capsid content (Cp), or the percentage vector genome copies per capsid (Vg %) of AAV compositions at a level of precision and reproducibility similar to that achieved by PCR, analytical ultracentrifugation and electron microscopy at a much lower cost in time and effort. A distinct advantage of the methods disclosed herein is that, due their ease of use, they can be readily integrated into the AAV manufacturing cycle to determine the quality of AAV compositions at both upstream and downstream stages of the manufacturing cycle. For example, the methods disclosed herein can be used to characterize AAV particles following each purification, formulation, and fill-finish step. Through the early detection of problems, the methods disclosed herein can significantly lower the cost of clinical AAV preparations by removing batches from the purification chain that do not meet quality requirement. The methods disclosed herein can also be used to test the quality of AAV preparations during storage, thus allowing the stockpiling of viral preparations when needed. Finally, the methods disclosed herein can be used to improve the safety and effectiveness of gene therapy by more precisely determining the genome copy dosage of viral particles administered to patients.

Embodiments of Characterization Methods

In one aspect, described herein are spectrophotometry methods for characterizing adeno-associated virus (AAV) preparations. In some embodiments, characterizing adeno-associated virus (AAV) preparations comprises determining genome content (Vg), capsid content (Cp), or the percentage vector genome copies per capsid (Vg %).

In some embodiments, a method of characterizing a composition comprising isolated AAV particles described herein comprises determining the absorbance of the composition comprising the AAV particles at least at 260 nm and at 280 nm, and calculating the genome content (Vg), capsid content (Cp), or the percentage vector genome copies per capsid (Vg %) applying the Beer-Lambert law. In some embodiments, the calculating uses an extinction coefficient that is specific for the genome of the isolated AAV particles. In some embodiments, the calculating uses an extinction coefficient that is specific for the capsid composition of the isolated AAV particles. In some embodiments, the calculating uses extinction coefficients that is specific for the genome of the isolated AAV particles and for the capsid composition of the isolated AAV particles. In some embodiments, the extinction coefficient that is specific for the genome of the isolated AAV particles and/or for the capsid composition of the isolated AAV is a theoretical extinction coefficient. In some embodiments, the extinction coefficient that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the method comprises calculating the genome content (Vg) of the composition comprising isolated AAV particles. In some embodiments, the method comprises calculating the capsid content (Cp) of the composition comprising isolated AAV particles. In some embodiments, the method comprises calculating the percentage vector genome copies per capsid (Vg %) of the composition comprising isolated AAV particles. In some embodiments, the AAV particles are recombinant AAV particles.

In some embodiments, the method further comprises determining the absorbance of the composition at an additional wavelength suitable for baseline correction. In some embodiments, the additional wavelength suitable for baseline correction is a wavelength between about 320 and about 400 nm. In some embodiments, the additional wavelength suitable for baseline correction is 340 nm. In some embodiments, the additional wavelength suitable for baseline correction is 214 nm.

In some embodiments, the isolated AAV particles are not denatured. In some embodiments, the isolated AAV particles are denatured.

In some embodiments, a method of characterizing a composition comprising isolated AAV particles described herein is an absolute quantification method that does not use a calibration curve.

In some embodiments, a method of determining the genome content (Vg) of a composition comprising isolated AAV particles described herein comprises determining the absorbance of the composition comprising the AAV particles at least at 260 nm and at 280 nm, and calculating the genome content (Vg) applying the Beer-Lambert law, wherein the calculating uses and extinction coefficients that is specific for the genome of the isolated AAV particles, and wherein the AAV particles are not denatured. In some embodiments, the AAV particles are recombinant AAV particles.

In some embodiments, a method of determining the genome content (Vg) of a composition comprising isolated AAV particles described herein comprises determining the absorbance of the composition comprising the AAV particles at least at 260 nm and at 280 nm, and calculating the genome content (Vg) applying the Beer-Lambert law, wherein the calculating uses extinction coefficients that are specific for the genome of the isolated AAV particles and for the capsid composition of the isolated AAV, and wherein the AAV particles are not denatured. In some embodiments, the AAV particles are recombinant AAV particles.

In some embodiments, a method of determining the capsid content (Cp) of a composition comprising isolated AAV particles described herein comprises determining the absorbance of the composition comprising the AAV particles at least at 260 nm and at 280 nm, and calculating the capsid content (Cp) applying the Beer-Lambert law, wherein the calculating uses and extinction coefficients that is specific for the genome of the isolated AAV particles, and wherein the AAV particles are not denatured. In some embodiments, the AAV particles are recombinant AAV particles.

In some embodiments, a method of determining the capsid content (Cp) of a composition comprising isolated AAV particles described herein comprises determining the absorbance of the composition comprising the AAV particles at least at 260 nm and at 280 nm, and calculating the capsid content (Cp) applying the Beer-Lambert law, wherein the calculating uses extinction coefficients that are specific for the genome of the isolated AAV particles and for the capsid composition of the isolated AAV, and wherein the AAV particles are not denatured. In some embodiments, the AAV particles are recombinant AAV particles.

In some embodiments, a method of determining the percentage vector genome copies per capsid (Vg %) of a composition comprising isolated AAV particles described herein comprises determining the absorbance of the composition comprising the AAV particles at least at 260 nm and at 280 nm, and calculating the percentage vector genome copies per capsid (Vg %) applying the Beer-Lambert law, wherein the calculating uses and extinction coefficients that is specific for the genome of the isolated AAV particles, and wherein the AAV particles are not denatured. In some embodiments, the AAV particles are recombinant AAV particles.

In some embodiments, a method of determining the percentage vector genome copies per capsid (Vg %) of a composition comprising isolated AAV particles described herein comprises determining the absorbance of the composition comprising the AAV particles at least at 260 nm and at 280 nm, and calculating the percentage vector genome copies per capsid (Vg %) applying the Beer-Lambert law, wherein the calculating uses extinction coefficients that are specific for the genome of the isolated AAV particles and for the capsid composition of the isolated AAV, and wherein the AAV particles are not denatured. In some embodiments, the AAV particles are recombinant AAV particles.

In some embodiments of the methods disclosed herein, genome content (Vg) is expressed in GC/mL (genome copy per mL), and applying the Beer-Lambert law to calculate genome content (Vg) comprises using the following equation $$Vg\ (GC/\text{mL}) = \frac{(A260 - \alpha A280)}{\varepsilon_{DNA260}\ (1 - \alpha/\beta)\ L},$$

wherein A=Absorbance; ε=Extinction Coefficient (Molar absorptivity); C=Sample Concentration; L=Path length, $\alpha=\varepsilon_{protein260}/\varepsilon_{protein280}$, $\beta=\varepsilon_{DNA260}/\varepsilon_{DNA280}$. In some embodiments, EDNA is specific for the genome of the isolated AAV particles. In some embodiments, $\varepsilon_{protein}$ is specific for the for the capsid composition of the isolated AAV. In some embodiments, EDNA is specific for the genome of the isolated AAV particles, and $\varepsilon_{protein}$ is specific for the for the capsid composition of the isolated AAV. In some embodiments, the isolated AAV particles are not denatured. In some embodiments, EDNA is specific for the genome of the isolated AAV particles, $\varepsilon_{protein}$ is specific for the for the capsid composition of the isolated AAV, and the isolated AAV particles are non-denatured. In some embodiments, the method is an absolute quantification method that does not use a calibration curve. In some embodiments, the extinction coefficients that is specific for the genome of the isolated AAV particles and/or for the capsid composition of the isolated AAV is a theoretical extinction coefficient. In some embodiments, the extinction coefficients that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the AAV particles are recombinant AAV particles.

In some embodiments of the methods disclosed herein, capsid content (Cp) is expressed as capsid/mL, and applying the Beer-Lambert law to calculate genome content (Vg) comprises using the following equation $$Cp\ (\text{capsid}/\text{mL}) = \frac{(A280 - A260/\beta}{\varepsilon_{protein280}\ (1 - \alpha/\beta)\ L},$$

wherein A=Absorbance; ε=Extinction Coefficient (Molar absorptivity); C=Sample Concentration; L=Path length, $\alpha=\varepsilon_{protein260}/\varepsilon_{protein280}$, $\beta=\varepsilon_{DNA260}/\varepsilon_{DNA280}$. In some embodiments, EDNA is specific for the genome of the isolated AAV particles. In some embodiments, $\varepsilon_{protein}$ is specific for the for the capsid composition of the isolated AAV. In some embodiments, EDNA is specific for the genome of the isolated AAV particles, and $\varepsilon_{protein}$ is specific for the for the capsid composition of the isolated AAV. In some embodiments, the isolated AAV particles are not denatured. In some embodiments, EDNA is specific for the genome of the isolated AAV particles, $\varepsilon_{protein}$ is specific for the for the capsid composition of the isolated AAV, and the isolated AAV particles are non-denatured. In some embodiments, the method is an absolute quantification method that does not use a calibration curve. In some embodiments, the extinction coefficients that is specific for the genome of the isolated AAV particles and/or for the capsid composition of the isolated AAV is a theoretical extinction coefficient. In some embodiments, the extinction coefficients that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the AAV particles are recombinant AAV particles.

In some embodiments of the methods disclosed herein, applying the Beer-Lambert law to calculate the percentage vector genome copies per capsid (Vg %) comprises using the following equations $$Vg\ (GC/\text{mL}) = \frac{(A260 - \alpha A280)}{\varepsilon_{DNA260}\ (1 - \alpha/\beta)\ L},$$

$$Cp\ (\text{capsid}/\text{mL}) = \frac{(A280 - A260/\beta)}{\varepsilon_{protein280}\ (1 - \alpha/\beta)\ L},$$

and $$Vg\ \% = Vg/Cp$$

wherein A=Absorbance; ε=Extinction Coefficient (Molar absorptivity); C=Sample Concentration; L=Path length, $\alpha=\varepsilon_{protein260}/\varepsilon_{protein280}$, $\beta=\varepsilon_{DNA260}/\varepsilon_{DNA280}$. In some embodiments, EDNA is specific for the genome of the isolated AAV particles. In some embodiments, $\varepsilon_{protein}$ is specific for the for the capsid composition of the isolated AAV. In some embodiments, EDNA is specific for the genome of the isolated AAV particles, and $\varepsilon_{protein}$ is specific for the for the capsid composition of the isolated AAV. In some embodiments, the isolated AAV particles are not denatured. In some embodiments, EDNA is specific for the genome of the isolated AAV particles, $\varepsilon_{protein}$ is specific for the for the capsid composition of the isolated AAV, and the isolated AAV particles are non-denatured. In some embodiments, the method is an absolute quantification method that does not use a calibration curve. In some embodiments, the extinction coefficients that is specific for the genome of the isolated AAV particles and/or for the capsid composition of the isolated AAV is a theoretical extinction coefficient. In some embodiments, the extinction coefficients that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the AAV particles are recombinant AAV particles.

In some embodiments of the methods disclosed herein, applying the Beer-Lambert law to calculate the percentage vector genome copies per capsid (Vg %) comprises using the following equation $$Vg(GC/\text{mL}) = \frac{(A_{260} - \alpha A_{280})}{\varepsilon_{DNA260}\ (1 - \alpha/\beta)L},$$

on experimental data obtained using standards with known Vg % to establish the correlation of Vg % and $A_{260}/A_{280}$, and using the correlation curve to determine the Vg % of a sample, wherein A=Absorbance; ε=Extinction Coefficient (Molar absorptivity); $\alpha=\varepsilon_{protein260}/\varepsilon_{protein280}$, $\beta=\varepsilon_{DNA260}/\varepsilon_{DNA280}$. In some embodiments, a method disclosed herein further comprises adjusting α, β, $\varepsilon_{protein}$ and EDNA by fitting experimental data obtained using standards with known Vg %. In some embodiments, EDNA is specific for the genome of the isolated AAV particles. In some embodiments, $\varepsilon_{protein}$ is specific for the for the capsid composition of the isolated AAV. In some embodiments, EDNA is specific for the genome of the isolated AAV particles, and $\varepsilon_{protein}$ is specific for the capsid composition of the isolated AAV. In some embodiments, the isolated AAV particles are not denatured. In some embodiments, EDNA is specific for the genome of the isolated AAV particles, $\varepsilon_{protein}$ is specific for the for the capsid composition of the isolated AAV, and the isolated AAV particles are non-denatured. In some embodiments, the method is an absolute quantification method that does not use a calibration curve. In some embodiments, the extinction coefficients that is specific for the genome of the isolated AAV particles and/or for the capsid composition of the isolated AAV is a theoretical extinction coefficient. In some embodiments, the extinction coefficients that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the AAV particles are recombinant AAV particles.

In some embodiments, a spectrophotometry method for characterizing a composition comprising isolated AAV particles described herein comprises determining the absorbance of the composition comprising the AAV particles at least at 260 nm and at 280 nm using slope spectroscopy, and calculating the genome content (Vg), capsid content (Cp), or the percentage vector genome copies per capsid (Vg %) applying the Beer-Lambert law. In some embodiments, the calculating uses an extinction coefficient that is specific for the genome of the isolated AAV particles. In some embodiments, the calculating uses an extinction coefficient that is specific for the capsid composition of the isolated AAV particles. In some embodiments, the calculating uses extinction coefficients that is specific for the genome of the isolated AAV particles and for the capsid composition of the isolated AAV particles. In some embodiments, the extinction coefficient that is specific for the genome of the isolated AAV particles and/or for the capsid composition of the isolated AAV is a theoretical extinction coefficient. In some embodiments, the extinction coefficient that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the method further comprises determining the absorbance of the composition at an additional wavelength suitable for baseline correction. In some embodiments, the additional wavelength suitable for baseline correction is a wavelength between about 320 and about 400 nm. In some embodiments, the additional wavelength suitable for baseline correction is 340 nm. In some embodiments, the additional wavelength suitable for baseline correction is 214 nm. In some embodiments, the isolated AAV particles are not denatured. In some embodiments, the isolated AAV particles are denatured. In some embodiments, a method of characterizing a composition comprising isolated AAV particles described herein is an absolute quantification method that does not use a calibration curve. In some embodiments, the method comprises calculating the genome content (Vg) of the composition comprising isolated AAV particles. In some embodiments, the method comprises calculating the capsid content (Cp) of the composition comprising isolated AAV particles. In some embodiments, the method comprises calculating the percentage vector genome copies per capsid (Vg %) of the composition comprising isolated AAV particles. In some embodiments, the AAV particles are recombinant AAV particles.

In some embodiments of a spectrophotometry method comprising the use of slope spectroscopy for characterizing a composition comprising isolated AAV particles described herein, applying the Beer-Lambert law to calculate genome content (Vg) comprises using the following equation $$Vg=K_{DNA}S_{DNA},$$

wherein $$K_{DNA}=\frac{1}{\varepsilon_{DNA260}\left(1-\alpha/\beta\right)},$$

$S_{DNA}$ is the slope of (A260–α A280) plotted against the path length L, and

A=Absorbance; ε=Extinction Coefficient (Molar absorptivity); $\alpha=\varepsilon_{protein260}/\varepsilon_{protein280}$, and $\beta=\varepsilon_{DNA260}/\varepsilon_{DNA280}$. In some embodiments, EDNA is specific for the genome of the isolated AAV particles. In some embodiments, $\varepsilon_{protein}$ is specific for the for the capsid composition of the isolated AAV. In some embodiments, EDNA is specific for the genome of the isolated AAV particles, and $\varepsilon_{protein}$ is specific for the for the capsid composition of the isolated AAV. In some embodiments, the isolated AAV particles are not denatured. In some embodiments, EDNA is specific for the genome of the isolated AAV particles, $\varepsilon_{protein}$ is specific for the for the capsid composition of the isolated AAV, and the isolated AAV particles are non-denatured. In some embodiments, the method is an absolute quantification method that does not use a calibration curve. In some embodiments, the extinction coefficients that is specific for the genome of the isolated AAV particles and/or for the capsid composition of the isolated AAV is a theoretical extinction coefficient. In some embodiments, the extinction coefficients that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the AAV particles are recombinant AAV particles.

In some embodiments of a spectrophotometry method comprising the use of slope spectroscopy for characterizing a composition comprising isolated AAV particles described herein, applying the Beer-Lambert law to calculate capsid content (Cp) comprises using the following equation $$Cp=K_{protein}S_{protein},$$

wherein $$K_{protein}=\frac{1}{\varepsilon_{protein280}\left(1-\alpha/\beta\right)},$$

$S_{protein}$ is the slope of (A280-A260/β) plotted against the path length L, and A=Absorbance; ε=Extinction Coefficient (Molar absorptivity); $\alpha=\varepsilon_{protein260}/\varepsilon_{protein280}$, and $\beta=\varepsilon_{DNA260}/\varepsilon_{DNA280}$. In some embodiments, EDNA is specific for the genome of the isolated AAV particles. In some embodiments, $\varepsilon_{protein}$ is specific for the for the capsid composition of the isolated AAV. In some embodiments, EDNA is specific for the genome of the isolated AAV particles, and $\varepsilon_{protein}$ is specific for the for the capsid composition of the isolated AAV. In some embodiments, the isolated AAV particles are not denatured. In some embodiments, EDNA is specific for the genome of the isolated AAV particles, $\varepsilon_{protein}$ is specific for the for the capsid composition of the isolated AAV, and the isolated AAV particles are non-denatured. In some embodiments, the method is an absolute quantification method that does not use a calibration curve. In some embodiments, the extinction coefficients that is specific for the genome of the isolated AAV particles and/or for the capsid composition of the isolated AAV is a theoretical extinction coefficient. In some embodiments, the extinction coefficients that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the AAV particles are recombinant AAV particles.

In some embodiments of a spectrophotometry method comprising the use of slope spectroscopy for characterizing a composition comprising isolated AAV particles described herein, applying the Beer-Lambert law to calculate the percentage vector genome copies per capsid (Vg %) comprises using the following equation $$Vg\ \%=Vg/Cp,$$

wherein $$Vg=K_{DNA}S_{DNA},$$

$$Cp=K_{protein}S_{protein},$$

$$K_{DNA}=\frac{1}{\varepsilon_{DNA260}\left(1-\alpha/\beta\right)},$$

$$K_{protein}=\frac{1}{\varepsilon_{protein280}\left(1-\alpha/\beta\right)}$$

$S_{DNA}$ is the slope of (A260−α A280) plotted against the path length L, $S_{protein}$ is the slope of (A280-A260/β) plotted against the path length L, and A=Absorbance; ε=Extinction Coefficient (Molar absorptivity); $\alpha=\varepsilon_{protein260}/\varepsilon_{protein280}$, and $\beta=\varepsilon_{DNA260}/\varepsilon_{DNA280}$. In some embodiments, EDNA is specific for the genome of the isolated AAV particles. In some embodiments, $\varepsilon_{protein}$ is specific for the for the capsid composition of the isolated AAV. In some embodiments, EDNA is specific for the genome of the isolated AAV particles, and $\varepsilon_{protein}$ is specific for the for the capsid composition of the isolated AAV. In some embodiments, the isolated AAV particles are not denatured. In some embodiments, EDNA is specific for the genome of the isolated AAV particles, $\varepsilon_{protein}$ is specific for the for the capsid composition of the isolated AAV, and the isolated AAV particles are non-denatured. In some embodiments, the method is an absolute quantification method that does not use a calibration curve. In some embodiments, the extinction coefficients that is specific for the genome of the isolated AAV particles and/or for the capsid composition of the isolated AAV is a theoretical extinction coefficient. In some embodiments, the extinction coefficients that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the AAV particles are recombinant AAV particles.

In one aspect, described herein are methods for using an HPLC system with UV detection to characterize AAV preparations. In some embodiments, characterizing AAV preparations comprises determining genome content (Vg), capsid content (Cp), or the percentage vector genome copies per capsid (Vg %).

In some embodiments, a method of characterizing a composition comprising isolated AAV particles described herein comprises analyzing the composition on an HPLC system with UV detection to determine the peak absorbance corresponding to the AAV particles at least at 260 nm and at 280 nm, and calculating the genome content (Vg), capsid content (Cp), or the percentage vector genome copies per capsid (Vg %) applying the Beer-Lambert law. In some embodiments, the HPLC system is a size exclusion high performance chromatography (SEC-HPLC) system, ion exchange high performance chromatography (IE-HPLC) system, or an affinity and reversed phase high performance chromatography (RP-HPLC) system. In some embodiments, the HPLC system is a SEC-HPLC system. In some embodiments, the calculating uses an extinction coefficient that is specific for the genome of the isolated AAV particles. In some embodiments, the calculating uses an extinction coefficient that is specific for the capsid composition of the isolated AAV particles. In some embodiments, the calculating uses extinction coefficients that is specific for the genome of the isolated AAV particles and for the capsid composition of the isolated AAV particles. In some embodiments, the extinction coefficient that is specific for the genome of the isolated AAV particles and/or for the capsid composition of the isolated AAV is a theoretical extinction coefficient. In some embodiments, the extinction coefficient that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the method further comprises determining the absorbance of the composition at an additional wavelength suitable for baseline correction. In some embodiments, the additional wavelength suitable for baseline correction is a wavelength between about 320 and about 400 nm. In some embodiments, the additional wavelength suitable for baseline correction is 340 nm. In some embodiments, the additional wavelength suitable for baseline correction is 214 nm. In some embodiments, the isolated AAV particles are not denatured. In some embodiments, the isolated AAV particles are denatured. In some embodiments, a method of characterizing a composition comprising isolated AAV particles described herein is an absolute quantification method that does not use a calibration curve. In some embodiments, the method comprises calculating the genome content (Vg) of the composition comprising isolated AAV particles. In some embodiments, the method comprises calculating the capsid content (Cp) of the composition comprising isolated AAV particles. In some embodiments, the method comprises calculating the percentage vector genome copies per capsid (Vg %) of the composition comprising isolated AAV particles. In some embodiments, the AAV particles are recombinant AAV particles.

In some embodiments of a spectrophotometry method comprising the use of an HPLC system with UV detection for characterizing a composition comprising isolated AAV particles described herein, applying the Beer-Lambert law to calculate genome content (Vg) comprises using the following equation $$Vg=fK_{DNA}(\mathrm{Peak}_{260}-\alpha\mathrm{Peak}_{280})/(uL),$$

wherein $$K_{DNA}=\frac{1}{\varepsilon_{DNA260}\,(1-\alpha/\beta)};$$

f=flow rate; ε=Extinction Coefficient (Molar absorptivity); $\alpha=\varepsilon_{protein260}/\varepsilon_{protein280}$, and $\beta=\varepsilon_{DNA260}/\varepsilon_{DNA280}$; u=injection volume. In some embodiments, the HPLC system is a size exclusion high performance chromatography (SEC-HPLC) system, ion exchange high performance chromatography (IE-HPLC) system, or an affinity and reversed phase high performance chromatography (RP-HPLC) system. In some embodiments, the HPLC system is a SEC-HPLC system. In some embodiments, EDNA is specific for the genome of the isolated AAV particles. In some embodiments, $\varepsilon_{protein}$ is specific for the for the capsid composition of the isolated AAV. In some embodiments, EDNA is specific for the genome of the isolated AAV particles, and $\varepsilon_{protein}$ is specific for the for the capsid composition of the isolated AAV. In some embodiments, the isolated AAV particles are not denatured. In some embodiments, EDNA is specific for the genome of the isolated AAV particles, $\varepsilon_{protein}$ is specific for the for the capsid composition of the isolated AAV, and the isolated AAV particles are non-denatured. In some embodiments, the method is an absolute quantification method that does not use a calibration curve. In some embodiments, the extinction coefficients that is specific for the genome of the isolated AAV particles and/or for the capsid composition of the isolated AAV is a theoretical extinction coefficient. In some embodiments, the extinction coefficients that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the AAV particles are recombinant AAV particles.

In some embodiments of a spectrophotometry method comprising the use of an HPLC system with UV detection for characterizing a composition comprising isolated AAV particles described herein, applying the Beer-Lambert law to calculate capsid content (Cp) comprises using the following equation $$Cp=fK_{protein}(\mathrm{Peak}_{280}-\mathrm{Peak}_{260}/\beta)/(uL),$$

wherein $$K_{protein}=\frac{1}{\varepsilon_{protein280}\,(1-\alpha/\beta)};$$

f=flow rate; ε=Extinction Coefficient (Molar absorptivity); $\alpha=\varepsilon_{protein260}/\varepsilon_{protein280}$, and $\beta=\varepsilon_{DNA260}/\varepsilon_{DNA280}$; u=injection volume. In some embodiments, the HPLC system is a size exclusion high performance chromatography (SEC-HPLC) system, ion exchange high performance chromatography (IE-HPLC) system, or an affinity and reversed phase high performance chromatography (RP-HPLC) system. In some embodiments, the HPLC system is a SEC-HPLC system. In some embodiments, EDNA is specific for the genome of the isolated AAV particles. In some embodiments, $\varepsilon_{protein}$ is specific for the for the capsid composition of the isolated AAV. In some embodiments, EDNA is specific for the genome of the isolated AAV particles, and $\varepsilon_{protein}$ is specific for the for the capsid composition of the isolated AAV. In some embodiments, the isolated AAV particles are not denatured. In some embodiments, EDNA is specific for the genome of the isolated AAV particles, $\varepsilon_{protein}$ is specific for the for the capsid composition of the isolated AAV, and the isolated AAV particles are non-denatured. In some embodiments, the method is an absolute quantification method that does not use a calibration curve. In some embodiments, the extinction coefficients that is specific for the genome of the isolated AAV particles and/or for the capsid composition of the isolated AAV is a theoretical extinction coefficient. In some embodiments, the extinction coefficients that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the AAV particles are recombinant AAV particles.

In some embodiments, a method of determining the capsid content (Cp) of a composition comprising isolated AAV particles described herein comprises analyzing the composition on an HPLC system with UV detection to determine the peak absorbance corresponding to the AAV particles at least at 214 nm, 260 nm, and at 280 nm, and calculating the capsid content (Cp) applying the Beer-Lambert law. In some embodiments, the HPLC system is a size exclusion high performance chromatography (SEC-HPLC) system, ion exchange high performance chromatography (IE-HPLC) system, or an affinity and reversed phase high performance chromatography (RP-HPLC) system. In some embodiments, the HPLC system is a SEC-HPLC system. In some embodiments, the calculating uses an extinction coefficient that is specific for the genome of the isolated AAV particles. In some embodiments, the calculating uses an extinction coefficient that is specific for the capsid composition of the isolated AAV particles. In some embodiments, the calculating uses extinction coefficients that is specific for the genome of the isolated AAV particles and for the capsid composition of the isolated AAV particles. In some embodiments, the extinction coefficient that is specific for the genome of the isolated AAV particles and/or for the capsid composition of the isolated AAV is a theoretical extinction coefficient. In some embodiments, the extinction coefficient that is specific for the genome of the isolated AAV particles and/or for the capsid composition of the isolated AAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the method further comprises determining the absorbance of the composition at an additional wavelength suitable for baseline correction. In some embodiments, the additional wavelength suitable for baseline correction is a wavelength between about 320 and about 400 nm. In some embodiments, the additional wavelength suitable for baseline correction is 340 nm. In some embodiments, the additional wavelength suitable for baseline correction is 214 nm. In some embodiments, the isolated AAV particles are not denatured. In some embodiments, the isolated AAV particles are denatured. In some embodiments, the method of determining the capsid content (Cp) is an absolute quantification method uses a calibration curve. In some embodiments, the AAV particles are recombinant AAV particles. In some embodiments, the applying the Beer-Lambert law to calculate capsid content (Cp) comprises using the following equation $$\text{Capsid titer}=m(\text{Total Sample Absorbance @214 nm}-(\text{Total DNA Absorbance @ 214 nm}))-b;$$

wherein m=Slope of empty capsid linear regression

A214, A260, A280=Peak area at UV 214, 260 and 280 nm wavelengths b=y-intercept of empty calibration curve. In some embodiments, the applying the Beer-Lambert law to calculate capsid content (Cp) comprises using the following equation $$\text{Capsid titer}=m(A_{214\ AAV}-K(A_{260\ AAV}-0.590A_{280\ AAV}))-b;$$

wherein m=Slope of empty capsid linear regression;

A214, A260, A280=Peak area at UV 214, 260 and 280 nm wavelengths;

K—A factor related to A214/A260 ratio of DNA; and b=y-intercept of empty calibration curve.

It will be apparent to a skilled artisan that the methods for characterizing AAV particles disclosed herein can readily be adapted for the characterization of two component system other than AAV particles. Thus, in one aspect, disclosed herein are methods for characterizing compositions comprising two-component systems. In some embodiments, the two component system comprises a DNA component and a protein component. In some embodiments, the two component system comprises a protein component conjugated to a non-protein molecule, for example, a small molecule drug. In some embodiments, the two component system comprises a virus. In some embodiments, the two component system comprises an antibody-drug conjugate. In some embodiments, a method of characterizing a composition comprising a two component system described herein comprises determining the absorbance of the composition comprising the two component system at least at a first and second wavelength corresponding to the peak absorbance the first and second component of the two-component system, and calculating the concentration of the first component and/or second component applying the Beer-Lambert law.

In one aspect, described herein are methods for using an HPLC system with UV detection to determine the concentration ($C_{molecule}$) of a biomolecule or a small organic molecule. In some embodiments, the biomolecule is an antibody, for example, a monoclonal antibody. In some embodiments, the method comprises analyzing the composition comprising the biomolecule or small organic molecule on an HPLC system with UV detection to determine the peak absorbance corresponding to the biomolecule or small organic molecule, and calculating the concentration of the biomolecule or small organic molecule using the Beer-Lambert law. In some embodiments, the HPLC system is a size exclusion high performance chromatography (SEC-HPLC) system, ion exchange high performance chromatography (IE-HPLC) system, or an affinity and reversed phase high performance chromatography (RP-HPLC) system. In some embodiments, the HPLC system is a SEC-HPLC system. In some embodiments, the method comprises using the equation:

$$C_{molecule}=Kcf\text{Peak}_{wavelength}/(uL\varepsilon_{wavelength}).$$

In some embodiments, the method is an absolute quantification method that does not use a calibration curve.

Application of the Methods

In one aspect, described herein are methods for producing a pharmaceutical composition comprising isolated recombinant AAV particles, comprising (i) isolating rAAV particles from a feed comprising an impurity by one or more of centrifugation, depth filtration, tangential flow filtration, ultrafiltration, affinity chromatography, size exclusion chromatography, ion exchange chromatography, and hydrophobic interaction chromatography, (ii) determining at least one of the genome titer (Vg), capsid titer (Cp), and percentage vector genome copies per capsid (Vg %) of the isolated rAAV particles using a method disclosed herein, and (iii) formulating the isolated rAAV particles to produce a pharmaceutical composition. In some embodiments, the pharmaceutical composition comprising isolated recombinant AAV particles is bulk drug substance. In some embodiments, the composition comprising isolated recombinant AAV particles is a pharmaceutical composition. In some embodiments, the composition comprising isolated recombinant AAV particles is a pharmaceutical unit dosage. In some embodiments, the composition comprising isolated recombinant AAV particles is a bulk drug substance. In some embodiments, determining at least one of Vg, Cp, and Vg % of the isolated rAAV particles comprises determining the absorbance of a composition comprising the rAAV particles at least at 260 nm and at 280 nm, and calculating at least one of the Vg, Cp, and Vg % applying the Beer-Lambert law. In some embodiments, the calculating uses an extinction coefficient that is specific for the genome of the isolated rAAV particles. In some embodiments, the calculating uses an extinction coefficient that is specific for the capsid composition of the isolated rAAV particles. In some embodiments, the calculating uses extinction coefficients that is specific for the genome of the isolated rAAV particles and for the capsid composition of the isolated rAAV particles. In some embodiments, the extinction coefficient that is specific for the genome of the isolated rAAV particles and/or for the capsid composition of the isolated rAAV is a theoretical extinction coefficient. In some embodiments, the extinction coefficient that is specific for the genome of the isolated rAAV particles and/or for the capsid composition of the isolated rAAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the method comprises calculating the genome content (Vg) of the composition comprising isolated rAAV particles. In some embodiments, the method comprises calculating the capsid content (Cp) of the composition comprising isolated rAAV particles. In some embodiments, the method comprises calculating the percentage vector genome copies per capsid (Vg %) of the composition comprising isolated rAAV particles. In some embodiments, the isolated AAV particles are not denatured. In some embodiments, the isolated AAV particles are denatured. In some embodiments, the method of characterizing the isolated rAAV particles is an absolute quantification method that does not use a calibration curve.

In one aspect, a method of characterizing a composition comprising isolated rAAV particles described herein is used for quality control during a rAAV manufacturing process. In one embodiment, a method disclosed herein is used to determine at least one of Vg, Cp, and Vg % of the isolated rAAV particles following a purification step. In some embodiments, the at least one of Vg, Cp, and Vg % is determined after a centrifugation, depth filtration, tangential flow filtration, ultrafiltration, affinity chromatography, size exclusion chromatography, ion exchange chromatography, or hydrophobic interaction chromatography step. In one embodiment, a method disclosed herein is used to determine at least one of Vg, Cp, and Vg % of the isolated rAAV particles following a formulation step. In one embodiment, a method disclosed herein is used to determine at least one of Vg, Cp, and Vg % of the isolated rAAV particles following a fill-finish step. In one embodiment, a method disclosed herein is used to determine at least one of Vg, Cp, and Vg % of isolated rAAV particles in a bulk drug substance.

In one aspect, described herein are methods for treating a disease or disorder in a subject in need thereof, comprising administering to the subject a therapeutically effective dose of isolated recombinant adeno-associated virus (rAAV) particles, wherein the amount of rAAV particles contained by the therapeutically effective dose has been determined using a method of characterizing a composition comprising isolated AAV particles described herein. In some embodiments, the method of characterizing a composition comprising isolated rAAV particles described herein comprises determining the absorbance of the composition comprising the rAAV particles at least at 260 nm and at 280 nm, and calculating the genome content (Vg), capsid content (Cp), or the percentage vector genome copies per capsid (Vg %) applying the Beer-Lambert law. In some embodiments, the calculating uses an extinction coefficient that is specific for the genome of the isolated rAAV particles. In some embodiments, the calculating uses an extinction coefficient that is specific for the capsid composition of the isolated rAAV particles. In some embodiments, the calculating uses extinction coefficients that is specific for the genome of the isolated rAAV particles and for the capsid composition of the isolated rAAV particles. In some embodiments, the extinction coefficient that is specific for the genome of the isolated rAAV particles and/or for the capsid composition of the isolated rAAV is a theoretical extinction coefficient. In some embodiments, the extinction coefficient that is specific for the genome of the isolated rAAV particles and/or for the capsid composition of the isolated rAAV is experimentally determined. In some embodiments, the method further comprises determining the extinction coefficient that is specific for the genome of the isolated AAV particles. In some embodiments, the method further comprises determining the extinction coefficient that is specific for the capsid composition of the isolated AAV. In some embodiments, the method further comprises determining the extinction coefficient that is specific for the genome of the isolated AAV particles and for the capsid composition of the isolated AAV. In some embodiments, the method comprises calculating the genome content (Vg) of the composition comprising isolated rAAV particles. In some embodiments, the method comprises calculating the capsid content (Cp) of the composition comprising isolated rAAV particles. In some embodiments, the method comprises calculating the percentage vector genome copies per capsid (Vg %) of the composition comprising isolated rAAV particles.

Methods for Determining the Content of Biological Compositions

Currently, the industry standard is to use Polymerase Chain Reaction (PCR) to determine the genome copy (GC) content of adeno-associated viruses (AAV), and Analytical Ultracentrifugation (AUC) or Transmission Electron Microscopy (TEM) to determine the ratio of full to empty capsids. Both methods are time-consuming and require multiple steps. The example systems and methods described herein can, for example, provide for faster determinations when real-time results are needed.

Spectrophotometry (the measurement of the absorbance of light at specific wavelengths) is a common and easy technique for determining the concentration of therapeutic biologic products. This disclosure describes non-limiting of examples in which spectrophotometry is used to determine GC content of AAV, to determine capsid content of AAV, and to determine the ratio of full to empty capsids. By, among other things, taking the two components of AAV (DNA with a spectra maxima of 260 nm, and protein with a spectra maxima of 280 nm) into account, spectrophotometry as described herein can be used to measure both the genome and protein capsid content of AAV products. FIG. 1 illustrates a representative absorbance spectra of AAV capsids.

A prior publication (Jurg M. Sommer, Quantification of Adeno-Associated Virus Particles and Empty Capsids by Optical Density Measurement. Molecular Therapy, Vol. 7, pages 122-128, 2003) states that denatured AAV decreases light scattering caused by large molecules.

The Applicant evaluated light scattering by analyzing the same AAV sample under denaturing conditions (heated at 75° C. for 10 minutes with 0.1% SDS) and non-denaturing conditions (no prior sample treatment). The results of the evaluation are shown in FIG. 2.

Figure 2:
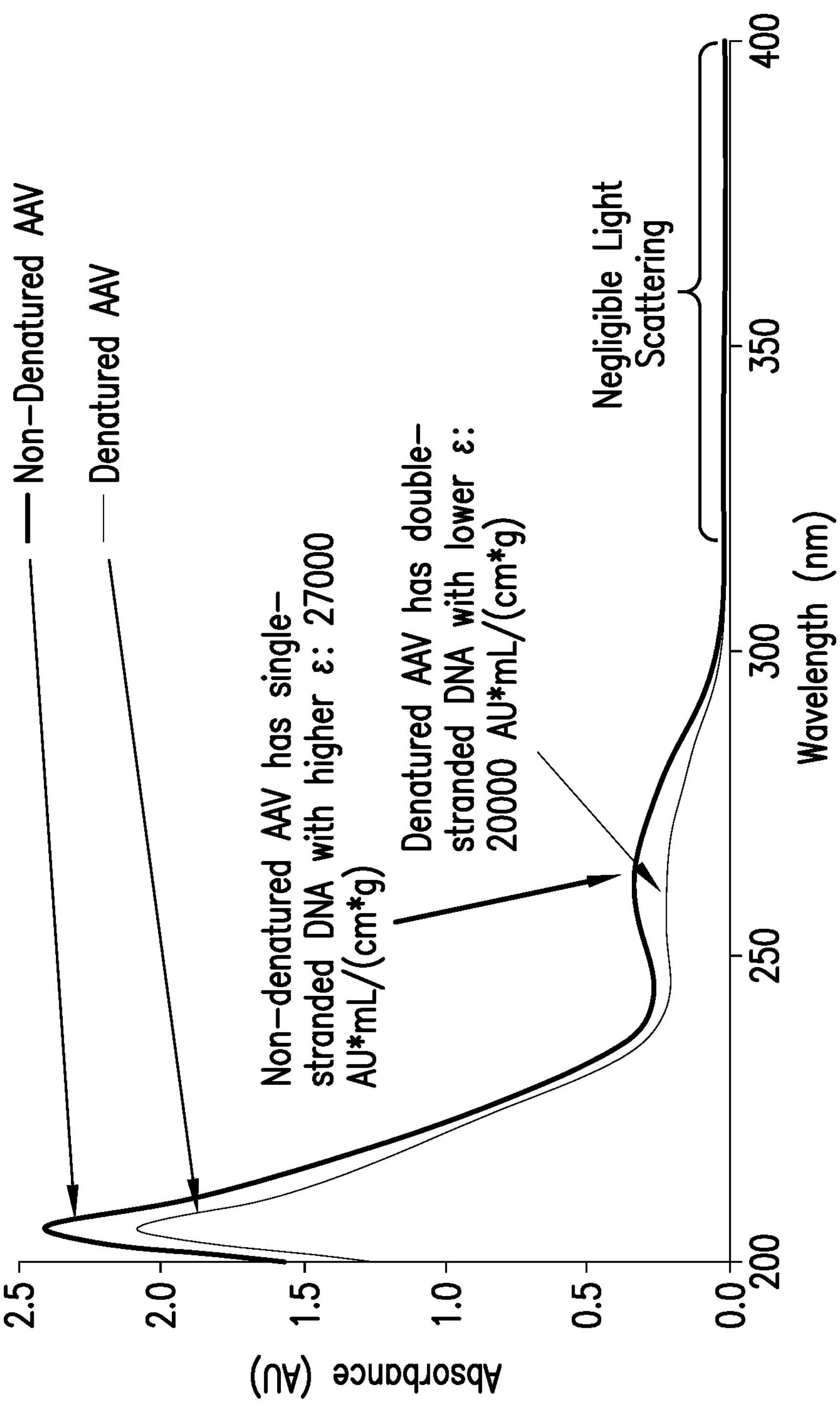
FIG. 2 illustrates the results of analyzing an AAV sample under denaturing conditions (heated at 75° C. for 10 minutes with 0.1% SDS) and non-denaturing conditions (no prior sample treatment). The extinction coefficients shown are for a representative sample.

The results shown in FIG. 2 demonstrate that denaturation is not necessary for AAV spectrophotometry analysis. In particular, FIG. 2 shows negligible levels of light scattering under non-denaturing conditions as indicated by similar low absorbance above approximately 320 nm.

In some embodiments, the method is performed on AAV samples that have not been denatured. There are several advantages of AAV analysis under non-denaturing conditions. For example, higher sensitivity due to higher & of single-stranded DNA. In addition, there is no sample preparation which makes the analysis faster and less prone to analyst-error. By way of example, the same AAV sample was tested by two (2) different analysts during six (6) different experiments. The results were highly precise as shown in TABLE 1 below.

TABLE 1

| Experiment | GC/mL | Capsid/mL | % Full Capsids |
|---|---|---|---|
| Analyst 1, Experiment 1 | 7.6E+12 | 1.5E+13 | 50% |
| Analyst 1, Experiment 2 | 7.8E+12 | 1.5E+13 | 51% |
| Analyst 1, Experiment 3 | 7.7E+12 | 1.6E+13 | 49% |
| Analyst 1, Experiment 4 | 7.7E+12 | 1.6E+13 | 50% |
| Analyst 2, Experiment 1 | 7.5E+12 | 1.5E+13 | 50% |
| Analyst 2. Experiment 2 | 7.6E+12 | 1.5E+13 | 51% |
| Average | 7.7E+12 | 1.5E+13 | 50% |
| % Relative Standard Deviation | 1.4% | 1.6% | 2.0% |

Figure 3:
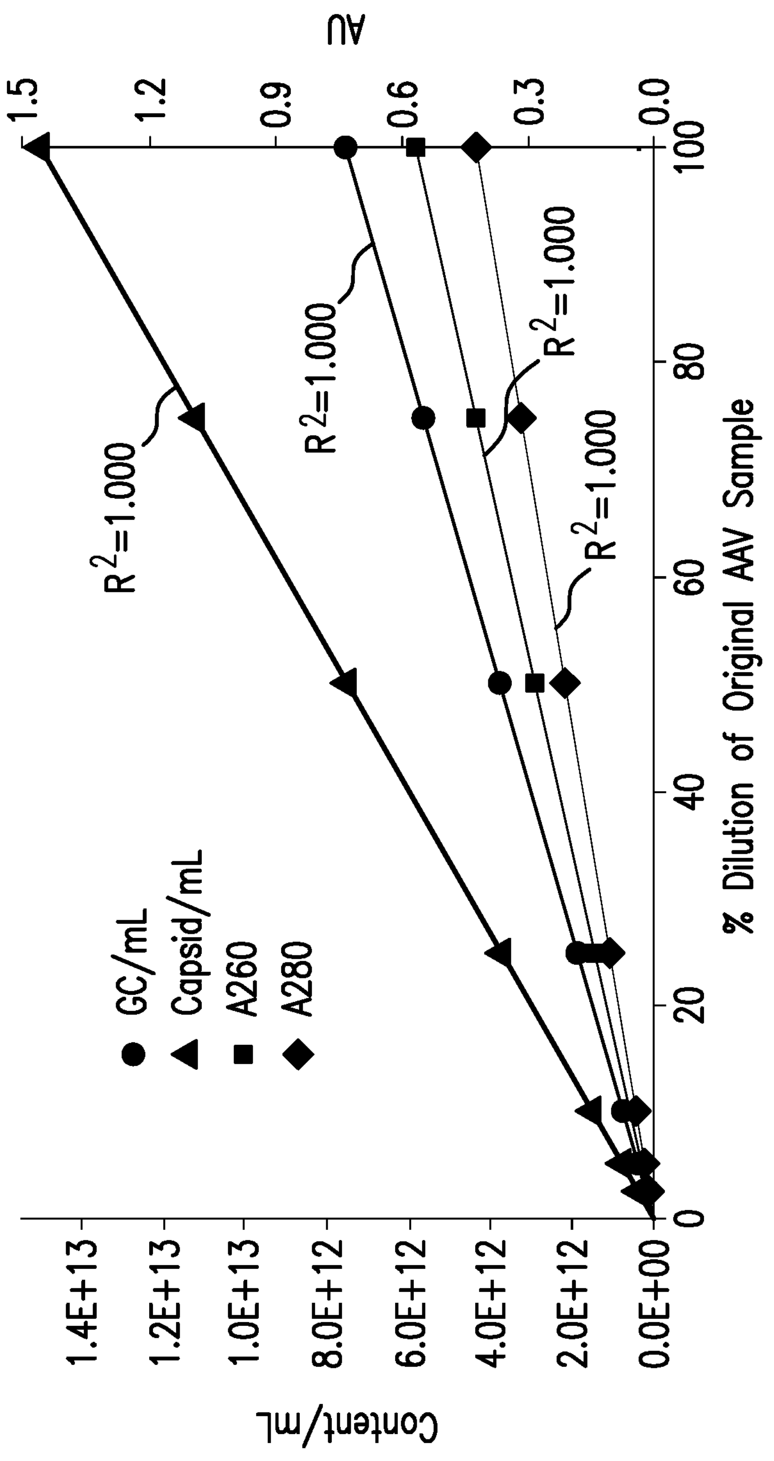
FIG. 3 is a graph illustrating the linearity and sensitivity of the denatured AAV analysis.

The AAV analysis under non-denaturing conditions demonstrates excellent linearity for A260 and A280 down to approximately 0.01 AU. See FIG. 3. Depending on the sensitivity of the instrument, accurate GC/mL values can be determined down to as low as approximately $2\times10^{11}$ GC/mL (using a 1 cm path length).

Figure 4:
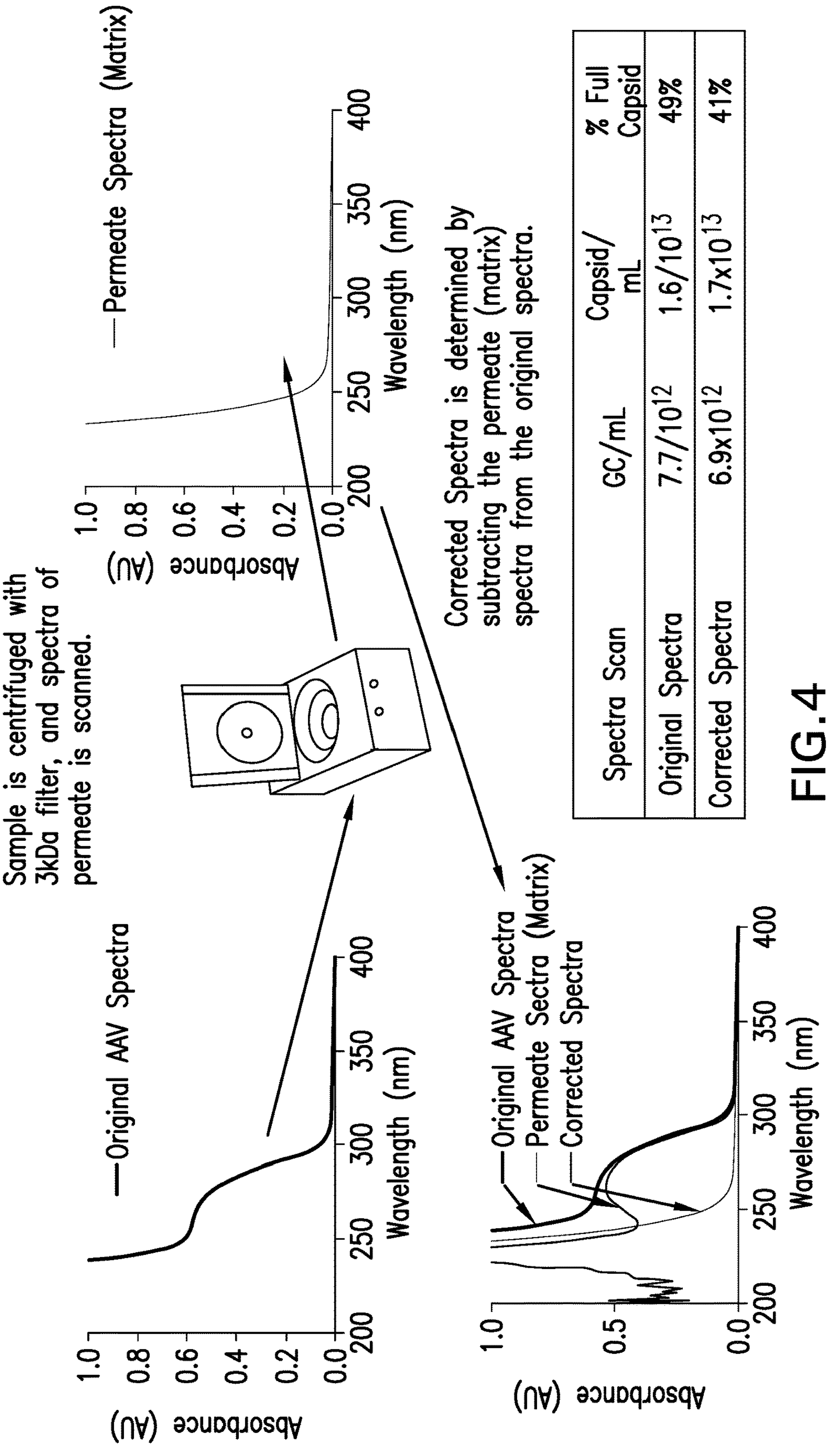
FIG. 4 illustrates a representative method for correcting spectra for matrix interference.
Figure 19:
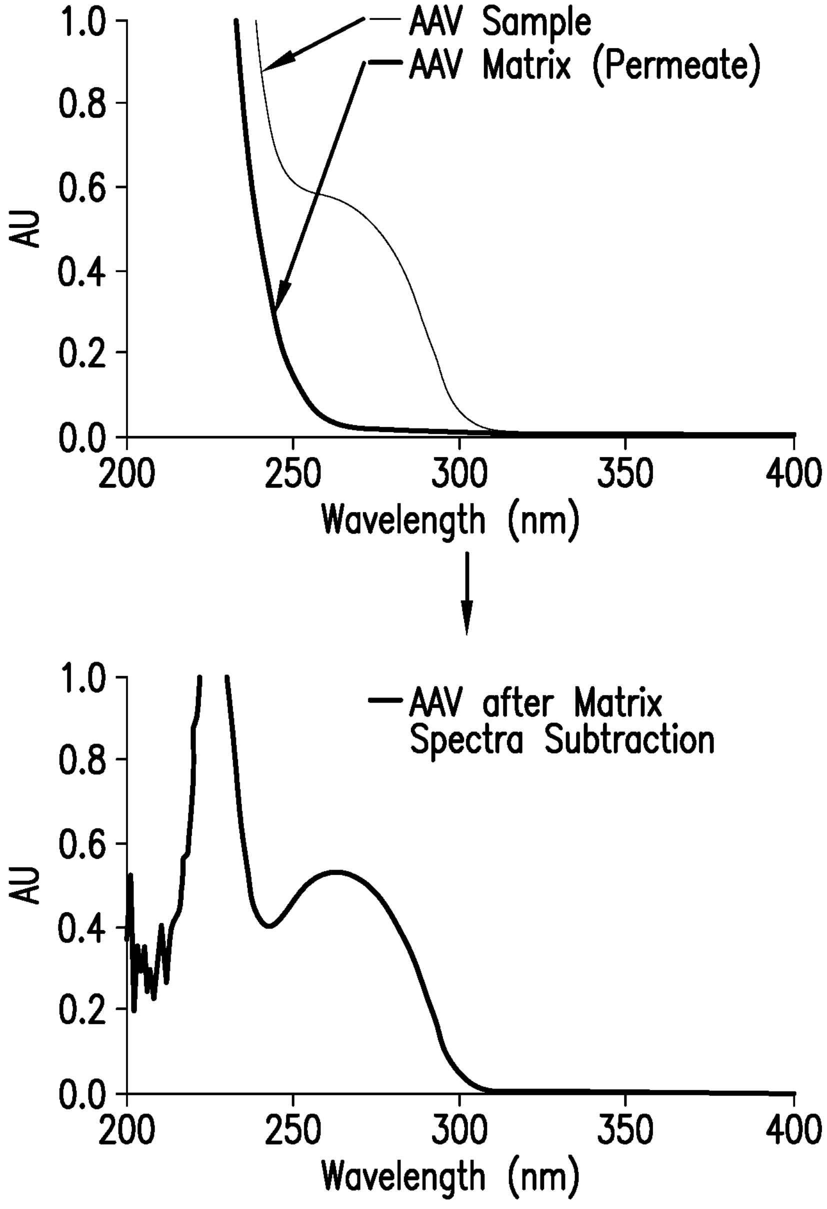
FIG. 19 illustrates a representative example for correcting spectra for matrix interference.

In-process samples may contain buffer components in the matrix, which could interfere with absorbance at 260 nm or 280 nm. For example, samples with matrix interference may cause inaccurate GC/mL and Capsid/mL calculations. More accurate values can be obtained from corrected spectra as shown in FIGS. 4 and 19. In one example, the sample for the original AAV spectra is centrifuged with a 3 kDa filter, and spectra of the permeate is scanned. In some embodiments, corrected spectra is determined by subtracting the permeate (matrix) spectra from the original spectra.

Figure 5:
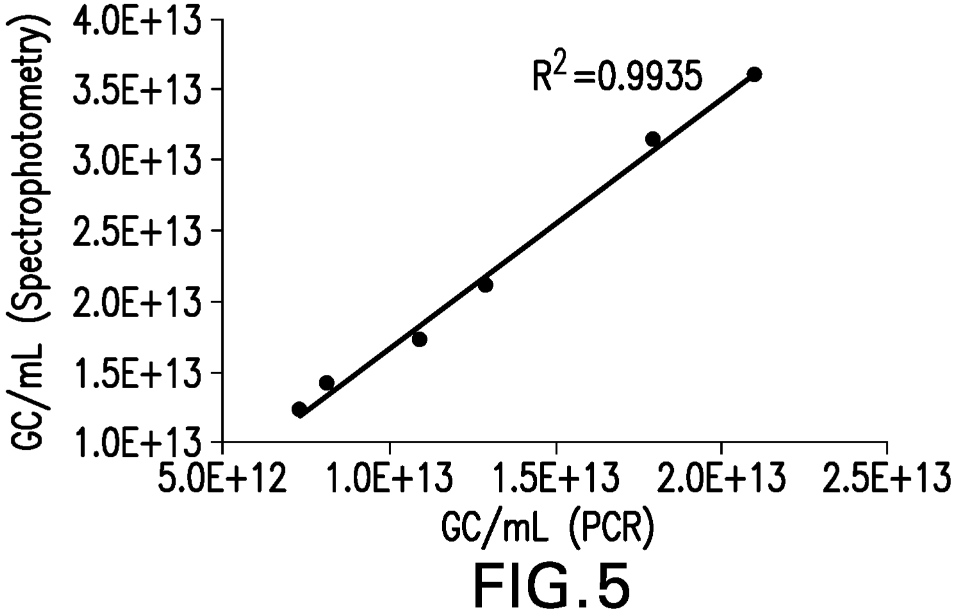
FIG. 5 illustrates correlation for six (6) samples between vector genome titer (GC/mL) determined by UV absorbance method (Spectrophotometry) and by ddPCR (the coefficient of determination: R2=0.99).

A comparison was also conducted between AAV spectrophotometry under non-denaturing conditions and PCR. Polymerase Chain Reaction (PCR) is a common technique for determining genome content of AAV. Although GC/mL values obtained by PCR vary between different testing sites due to the design of primer/probe and other factors, there was a very good correlation per PCR testing site. FIG. 5 illustrates correlation for six (6) samples between spectrophotometry and PCR at one site. A correction factor can be used to normalize the spectrophotometry value to the PCR, if needed.

Figure 6:
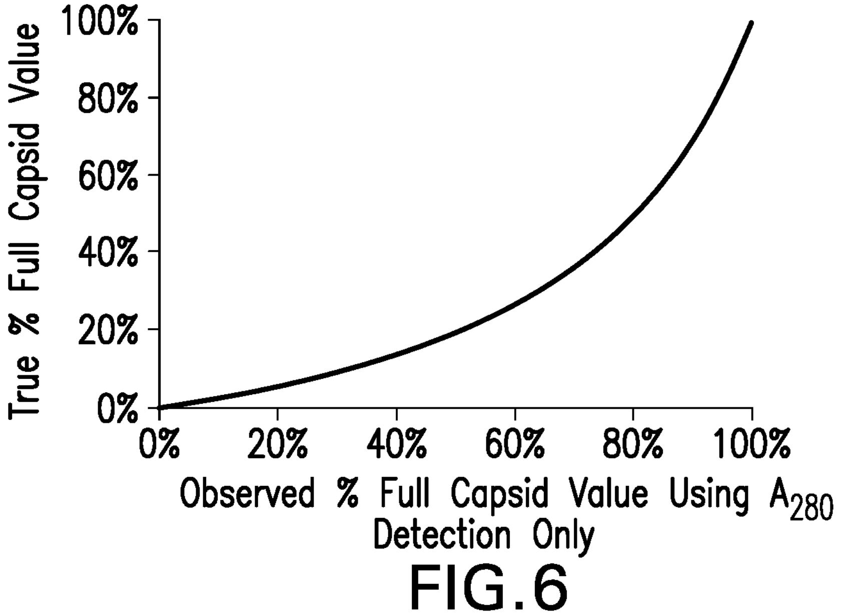
FIG. 6 compares the true % full capsid value and the observed % full capsid value determined by AUC using A280 detection only.

A comparison was also conducted between AAV spectrophotometry under non-denaturing conditions and AUC. Analytical Ultracentrifugation (AUC) is a common technique for determining the ratio of full to empty AAV capsids. When AUC detects using 280 nm, the level of full capsids are inherently over-estimated relative to the empty capsids because both DNA and protein contribute to the full capsid signal at 280 nm. See FIG. 6. A normalization is needed to determine true % full value. Comparing % Full Capsid values determined by spectrophotometry and AUC give comparable values for an AAV sample with negligible partially-full capsids. The AUC value is corrected, taking into account that full capsids have a higher signal than empty capsids using 280 nm detection. See, e.g. FIGS. 7, 13, 14 and 17.

Comparing % full capsid values determined by spectrophotometry versus AUC is more complicated for AAV sample with significant levels of partially-full capsids. The average distribution of DNA within the partially-full capsids can be estimated by comparing the sedimentation coefficients(S) of empty, full, and partially full capsid peaks. See FIG. 7.

In summary, the above results demonstrate that spectrophotometry can be used to determine the genome and capsid content of AAV products using detection at 260 and 280 nm. Analysis of non-denatured AAV samples has higher absorbance than denatured AAV samples, with negligible levels of light scattering. Buffer matrix subtraction can be used to improve accuracy of measurements of some in-process samples. The spectrophotometry values have good correlation to the values obtained by PCR (GC/mL) and AUC (% Full Capsids).

Additional details of absolute AAV vector genome titer and capsid titer by UV spectrophotometry and high-performance liquid chromatography are provided below.

a) UV Absorbance Method to Determine the Vector Genome Copy Numbers (Vector Genome Titer) and Capsid Particle Numbers (Capsid Titer)

Spectrophotometry is a common technique for measuring concentrations of therapeutic products, in which the product concentration is linearly correlated with the absorbance, the path length of the light beam, and extinction coefficient constant of the product at a specific wavelength. It follows the Beer-Lambert law, as shown below:

$$A=\varepsilon CL \qquad \text{Beer-Lambert law:}$$

where A=Absorbance; ε=Extinction Coefficient (Molar absorptivity); C=Sample Concentration; and L=Path length.

Adeno-associated virus includes the capsid proteins (which have an absorbance maxima at 280 nm) and DNA (which has an absorbance maxima at 260 nm). Generally speaking, AAV products with a high level of full capsids can be difficult to produce. AAV product samples are a mixture of full capsids and empty capsids. Thus, direct application of Beer-Lambert law with a single extinction coefficient constant at a specific wavelength to determine AAV product titer is not possible, since the protein and DNA levels vary in AAV products, resulting in a variable extinction coefficient. However, the UV absorbance of AAV products is a sum of absorbance by protein and DNA. AAV UV absorbance at 260 nm (A260) and at 280 nm (A280) can be calculated based on the following equations:

$$A_{260}=\varepsilon_{DNA260}Vg+\varepsilon_{protein260}Cp$$

$$A_{280}=\varepsilon_{DNA280}Vg+\varepsilon_{protein280}Cp$$

where Vg is the AAV vector titer and Cp is the capsid titer. Methods to determine UV extinction coefficients of proteins and DNA at their maximum UV absorbance wavelengths (DNA at 260 nm and proteins at 280 nm) are readily available and known in the art. To utilize the UV extinction coefficients of DNA at 260 nm and proteins at 280 nm, the above equations can be changed to:

$$A_{260}=\varepsilon_{DNA260}Vg+\alpha\varepsilon_{protein280}Cp$$

$$A_{280}=\beta\varepsilon_{DNA280}Vg+\varepsilon_{protein280}Cp$$

where $\alpha=\varepsilon_{protein260}/\varepsilon_{protein280}$ and $\beta=\varepsilon_{DNA260}/\varepsilon_{DNA280}$ $\alpha$ and $\beta$ can be determined by the UV absorbance ratio of capsid proteins and vector genome, respectively, at 260 nm and 280 nm.

The AAV vector genome titer Vg in GC/mL (genome copy per mL) and capsid titer Cp in capsid/mL can be deduced algebraically from above two equations and applying the Beer-Lambert Law.

$$Vg(GC/\text{mL})=\frac{(A_{260}-\alpha A_{280})}{\varepsilon_{DNA260}\,(1-\alpha/\beta)L}$$

and $$Cp(\text{capsid/mL})=\frac{(A_{280}-A_{260}/\beta)}{\varepsilon_{protein280}\,(1-\alpha/\beta)L}$$

Using the above equations, a single UV absorbance measurement of AAV products can directly provide both vector genome titer and capsid titer. The two equations above are applicable to both denaturing and non-denaturing conditions. Under non-denaturing conditions, no sample preparation is needed prior to UV measurement, thus, reducing the error caused by sample preparation. Furthermore, sensitivity increases under non-denaturing conditions, since AAV under non-denaturing conditions with single-stranded DNA has a higher UV extinction coefficient (0.027 mL AU/ug cm) than denatured AAV, in which the DNA anneals to form double-stranded DNA with an extinction coefficient of 0.020 mL Au/ug cm.

With Vg and Cp values determined using the above equations, the percentage vector genome copies per capsid, or Vg % value then can be calculated using the following equation:

$$Vg\ \%=Vg/Cp$$

Figure 9:
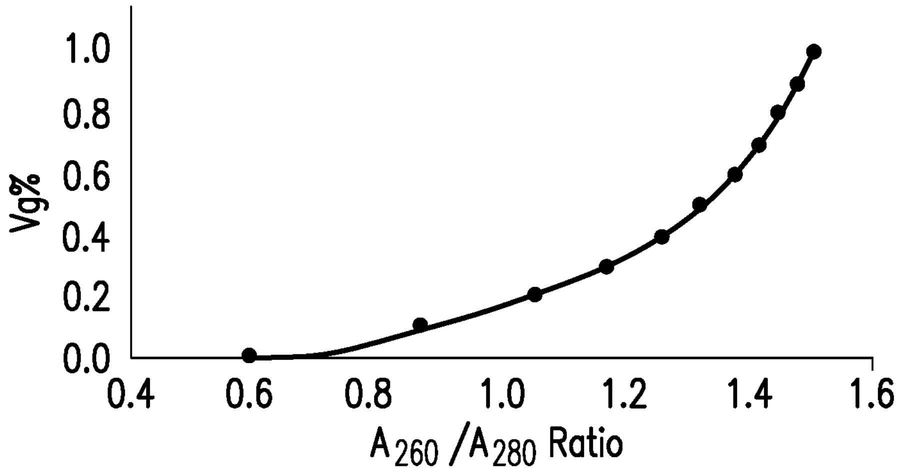
FIG. 9 shows an example of a correlation between Vg % (percentage vector genome copies per capsid) and the UV absorbance ratio $A_{260}/A_{280}$ for a representative sample.

Alternatively, the Vg % can be experimentally correlated with the $A_{260}/A_{280}$ ratio by spiking different levels of a known empty capsid sample (or a low Vg % sample) into a known full capsid sample (or a high Vg % sample), and then plotting the Vg % value against the measured $A_{260}/A_{280}$ ratio. FIG. 9 shows an example of such a correlation between Vg % and $A_{260}/A_{280}$. With a number of points of experimental data, a trendline can be simulated with a polynomial fit or with the equation below:

$$Vg\ \%=\frac{\beta\ \varepsilon_{protein}\ (A_{260}/A_{280}-\alpha)}{\varepsilon_{DNA}\ (\beta-A_{260}/A_{280})}$$

where, $\alpha$, $\beta$, $\varepsilon_{protein}$ and EDNA can be adjusted by fitting the experimental data. Once the correlation of Vg % and $A_{260}/A_{280}$ is established, the correlation curve can be utilized to determine the Vg % of a given AAV product sample by measuring its $A_{260}/A_{280}$ ratio using a spectrophotometer. In the alternative, Vg % is determined by $\varepsilon_{protein}$(A260−$\alpha$*A280)*100/$\varepsilon_{EDNA}$(A280−A260/$\beta$).

b) Impact of Light Scattering by AAV Particles on UV Absorbance is at Negligible Level As discussed below, the Applicant of the subject patent application has determined that the impact of light scattering by AAV particles on UV absorbance is at a negligible level.

A prior publication stressed the need of denaturing AAV capsids to prevent light scattering (Sommer, Jurg M. (January 2013). Quantification of Adeno-Associated Virus Particles and Empty Capsids by Optical Density Measurement. Molecular Therapy, Vol. 7, pages 122-128). Large molecules can cause light scattering, resulting in inaccurate light absorbance measurements. Since UV absorbance of both protein and DNA diminishes above 320 nm, an increased absorbance at wavelengths above 320 nm indicates the presence of light scattering.

Light scattering occurs with the particles smaller than the wavelength of light (Rayleigh scattering) or with the particles larger than the wavelength of light (Tyndall scattering). The scattering intensity is inversely proportional to the fourth power of the wavelength or to the square of the wavelength, respectively. Background simulation and correction is possible when the interference is due to light scattering. A portion of spectrum where the interference occurs, but lack of analyte absorbance, is selected. A polynomial or logarithmic data fitting is performed and extrapolated to the wavelength of interest to estimate the amount of light scattering at this wavelength. See FIG. 15 and Example 4. The extrapolated background is then subtracted from the measured absorbance value to obtain the absorbance attributed to the analyte. ("Fundamentals of UV-visible spectroscopy: A Primer", by Tony Owen, Hewlett-Packard (1996))

For AAV samples, results of the Applicant showed the amount of light scattering estimated by the above described method is below 3% of the total measured absorbance, most likely caused by other particles present in the solution. Low levels of light scattering, if present, can be corrected with the above method without a significant impact on the performance of the assay.

To evaluate the contribution of potential light scattering effect, denatured and non-denatured AAV samples were measured by spectrophotometry. The denatured sample was spiked with 0.1% sodium dodecyl sulfate and then heated at 75° C. for 10 minutes before analysis. The non-denatured sample was measured directly without any prior treatment. A comparison of the non-denatured sample versus the denatured AAV sample is shown in FIG. 2. The light scattering was at equivalent negligible levels for both samples, observed by the flat baseline in the 320-400 nm region.

c) Determine Extinction Coefficient of AAV Capsid Protein:

Amino acids containing aromatic side chains exhibit strong UV absorbance at 280 nm. Among them, tryptophan and tyrosine, and to a lesser extent cystine, contribute significantly to absorbance at 280 nm (A280), the absorbance maximum of proteins. Phenylalanine absorbs only at lower wavelengths (240-265 nm). Consequently, A280 is in direct proportion to aromatic amino acid content of the protein and total protein concentration. As described in Beer-Lambert's law, once the extinction coefficient of a protein is determined, the protein's concentration in solution can be calculated from its absorbance.

Theoretically, the molar extinction coefficient (¿) of a protein at 280 nm depends on its content of tryptophan (Trp), tyrosine (Tyr) and cystine (Cys). Pace et al. measured the & values for 80 proteins under both native and denaturing conditions, and proposed that at 280 nm, ε of a folded protein in water can be approximately calculated using the following equation (Pace C N et al., "How to measure and predict the molar absorbance coefficient of a protein" Protein Sci 1995):

$$\varepsilon(AU\ M^{-1}cm^{-1})=5500n_{Trp}+1490n_{Tyr}+125n_{Cys}$$

where nTrp, nTyr and nCys are the numbers of Trp, Tyr and Cys residues in the protein.

However, as a practical matter, different preparations of a protein solution in buffer type, ionic strength, pH and excipients may cause a slight difference in conformation and can also affect absorbance. Consequently, a better way to determine the extinction coefficient of a protein is to calculate value of & for the unfolded protein in 6 M guanidine HCl using values for those amino acid residues determined in 6 M guanidine HCl, and then measure UV absorbance of the protein in 6 M guanidine HCl and in the target sample matrix. If there is a difference, a correction can be made by absorbance ratio of intact protein in specific solution and denatured protein in 6 M Guanidine HCl ((a) Pace, C. N., Vajdos, F., Fee, L., Grimsley, G., and Gray, T. 1995. How to measure and predict the molar absorbance coefficient of a protein. Prot. Sci. 4:2411-2423. (b) Pace, C. N. and Schmid, F. X. 1997. How to determine the molar absorbance coefficient of a protein. In Protein Structure: A Practical Approach. (T. E. Creighton, ed.) pp. 253-259. IRL Press, Oxford, U.K.)

Amino acid analysis (AAA) can also be used for determining the absolute protein concentration experimental in solution by quantitation of each amino acid following acid hydrolysis. Amino acid analysis (AAA) has been used to verify the theoretical UV extinction coefficients (Sittampalam, G. S. et al., "Evaluation of Amino Acid. Analysis as Reference Method to Quantitate Highly. Purified Proteins," J. Assoc. Offic. Anal. Chem. 71(4), 833-838 (1988)).

Theoretically a capsid is made of 50 VP3, 5 VP2 and 5 VP1. The VP1:VP2:VP3 ratio may change depending on serotypes and the manufacturing process. The actual ratio can be determined experimentally by SDS-CGE or RP-HPLC. Using either the theoretical VP or experimental VP number per capsid, the UV extinction coefficient of capsids can be determined.

d) Determine Extinction Coefficient of AAV Genome DNA

Nucleic acids absorb UV light due to the heterocyclic rings of the nucleotides with the absorbance maximum for both DNA and RNA at 260 nm. The bases of DNA can stack on top of each other in the molecule (hypochromic effect) and reduce the UV absorbance. The tendency of the bases to stack is maximized in dsDNA. Thus, the absorbance of single-stranded DNA (ssDNA) is greater than that of double-stranded DNA (dsDNA).

There are several methods for calculating the extinction coefficients of nucleotide. One method assumes a nominal concentration of 33 µg/mL for ssDNA and 50 µg/mL for dsDNA in a 1 cm path length to obtain 1.0 absorbance unit (AU) at 260 nm (Sambrook J et al., "Molecular Cloning: A Laboratory Manual 2nd ed.", 1989). This method is generally used for the calculation of nucleic acid concentrations using absorbance at 260 nm regardless of the base composition in the sequence. Concentrations of nucleic acids determined using this method have been found fairly accurate. A later study using NMR to accurately determine DNA and RNA extinction coefficient recommended coefficients of 37 µg/mL at 260 nm based on a 1 cm path length for calculation of ssDNA concentrations (Cavaluzzi, M. J., Borer, P. N., "Revised UV extinction coefficients for nucleoside-5'-monophosphates and unpaired DNA and RNA.", Nucleic Acids Res. 2004, 32, 13e).

With known DNA sequence and molecular weight, the DNA UV extinction coefficients can be estimated as $$\varepsilon_{DNA260}=0.020MW_{DNA}\ (\mu g/mL)^{-1}cm^{-1}\ \text{for dsDNA}$$

$$\varepsilon_{DNA260}=0.027MW_{DNA}\ (\mu g/mL)^{-1}cm^{-1}\ \text{for ssDNA}$$

where $MW_{DNA}$ is the DNA molecular weight. Under denaturing conditions, the extinction coefficient of dsDNA was used for the determination of AAV GC titer and capsid titer using spectrophotometry (Sommer et al. in the 2003 publication). This is because the ssDNA enclosed in the AAV capsids were found to anneal spontaneously upon denaturation. Under non-denaturing conditions, vector genome takes a form as a single strand DNA and the extinction coefficient of ssDNA should be used for the calculation of vector GC titer and capsid titer.

It has been reported that the calculated extinction coefficients of DNA may differ as much as 10-20% from the experimentally determined values (Murugaiah V., "Determination of extinction coefficient" Handbook of Analysis of Oligonucleotides and Related Products, p 351-359, 2011). In addition, the DNA conformation inside AAV capsid can be significantly different from that in solution. One accurate way to determine the DNA UV extinction coefficients for AAV is to measure the UV absorbance of an AAV sample with known vector genome titer along with the UV absorbance of the isolated capsid proteins from the same sample. The difference in the UV absorbance of AAV ($A_{AAV}$) and its capsid proteins ($A_{cp}$) is the UV absorbance of vector DNA at a specific wavelength. The experimentally determined vector DNA UV extinction coefficient is $$\varepsilon_{DNA\_experiment}=(A_{AAV}-A_{cp})/\text{DNA\_concentration}$$

In addition, with well determined α, and $\varepsilon_{protein}$ from empty capsids, using experimental data of Vg % measured by either analytical ultracentrifugation (AUC) or transmission electron microscopy (TEM) for samples with different $A_{260}/A_{280}$, the β and EDNA can be obtained by fitting the equation below.

$$Vg\ \% = \frac{\beta\ \varepsilon_{protein}\ (A_{260}/A_{280}-\alpha)}{\varepsilon_{DNA}\ (\beta - A_{260}/A_{280})}$$

In some embodiments, AAV capsid titers are obtained against an empty AAV standard, the concentration of which can be accurately determined through conventional A280 and amino acid analysis. Using equation model fitting analysis with full % results from either analytical ultracentrifugation (AUC) or transmission electron microscopy (TEM) and accurate capsid protein UV extinction coefficients, the AAV genome DNA UV extinction coefficients can be very accurately determined.

e) Vector Genome Titer Determined by Spectrophotometry is in a Good Agreement or Correlation with PCR The UV absorbance method described above was used to determine the vector genome titers of AAV products. Representative data in Table 2 demonstrates that comparable vector genome titers were obtained by spectrophotometry method and by PCR performed at two different testing sites (Testing Site 1 using qPCR, and Testing Site 2 using ddPCR). Some of the variation in the difference between the values is primarily attributed to PCR method variation, which often has up to at least 20% variation in precision.

TABLE 2

AAV vector genome titers obtained by spectrophotometer and PCR

| Sample | PCR Testing Site | GC/mL (Spectrophotometry) | GC/mL PCR) | Relative Difference |
|---|---|---|---|---|
| AAV Lot 1 | PCR | $2.8 \times 10^{12}$ | $3.6 \times 10^{12}$ | 29% |
| AAV Lot 2 | Testing | $6.9 \times 10^{12}$ | $7.6 \times 10^{12}$ | 10% |
| AAV Lot 3 | Site 1 (qPCR) | $1.1 \times 10^{13}$ | $1.1 \times 10^{13}$ | 0% |
| AAV Lot 4 | PCR | $2.7 \times 10^{13}$ | $2.3 \times 10^{13}$ | −15% |
| AAV Lot 5 | Testing | $2.5 \times 10^{13}$ | $2.3 \times 10^{13}$ | −8% |
| AAV Lot 6 | Site 2 | $1.9 \times 10^{13}$ | $2.0 \times 10^{13}$ | 5% |
| AAV Lot 7 | (ddPCR) | $2.4 \times 10^{13}$ | $1.8 \times 10^{13}$ | −25% |

When side-by-side testing was performed for AAV samples by ddPCR, the assay variation was substantially reduced and correlation with data by spectrophotometry was observed (FIG. 5), although there is a large systematic difference due to a specific selection of PCR primer and probe near the inverted terminal repeat (ITR).

f) UV Spectrophotometry Method has Better Precision, Repeatability, Reproducibility, Robustness and Easy Method Transfer UV spectrophotometry has demonstrated better precision in determining the vector genome titer of AAV than those by PCR. Table 3 shows the precision between 2 analysts throughout 6 different experiments on different days, with ≤2.0% relative standard deviation for calculated vector genome titer (GC/mL), capsid titer (Capsid/mL), and percentage of full capsid (GC/Capsid or Vg %). The sensitivity (limit of quantitation) of the method is determined by the sensitivity of the spectrophotometer. For a spectrophotometer with a sensitivity limit of 0.01 AU, it roughly correlates to a limit of quantitation of approximately 1.5E+11 GC/mL for a vector genome titer of a typical AAV sample with 4 kbp genome. Further increase of sensitivity can be obtained with the use of HPLC as described below.

TABLE 3

Precision results of UV spectrophotometry methods

| Experiment | Vector Genome Titer (GC/mL) | Capsid Titer (Capsid/mL) | Vg % (GC/Capsid) |
|---|---|---|---|
| Analyst 1, Experiment 1 | $7.64 \times 10^{12}$ | $1.53 \times 10^{13}$ | 0.50 |
| Analyst 1, Experiment 2 | $7.83 \times 10^{12}$ | $1.53 \times 10^{13}$ | 0.51 |
| Analyst 1, Experiment 3 | $7.71 \times 10^{12}$ | $1.57 \times 10^{13}$ | 0.49 |
| Analyst 1, Experiment 4 | $7.73 \times 10^{12}$ | $1.55 \times 10^{13}$ | 0.50 |
| Analyst 2, Experiment 1 | $7.52 \times 10^{12}$ | $1.51 \times 10^{13}$ | 0.50 |
| Analyst 2, Experiment 2 | $7.63 \times 10^{12}$ | $1.50 \times 10^{13}$ | 0.51 |

TABLE 3-continued

Precision results of UV spectrophotometry methods

| Experiment | Vector Genome Titer (GC/mL) | Capsid Titer (Capsid/mL) | Vg % (GC/Capsid) |
|---|---|---|---|
| Average | $7.68 \times 10^{12}$ | $1.53 \times 10^{13}$ | 0.50 |
| % Relative Standard Deviation | 1.4% | 1.6% | 2.0% |

Under non-denaturing conditions, the method is highly robust because there is limited sample handling which therefore reduces the method variation. It is easy to transfer the method among different testing sites. It was demonstrated (data not shown) less than 6% difference in the vector genome titer of the same sample was achieved between two testing sites using different types of spectrophotometers.

g) Application to Other Two Component Systems

The above described equations and example methods may be applicable to other molecules or systems containing two components. It may be applicable to virus that contains DNA and proteins. It may also be applicable to protein drug conjugates.

h) GC Titer and Capsid Titer by Solo VPE

Multiple readings without dilution can be performed with slope spectroscopy. Accuracy, precision and method robustness can be improved with slope spectroscopy (Scott Huffman, Keyur Soni and Joe Ferraiolo, "UV-Vis Based Determination of Protein Concentration: Validating and Implementing Slope Measurements Using Variable Path length Technology", BioProcess International, 12 (8), 2014). Two equations in section a) above used to calculate vector genome titer and capsid titer can be simplified as $$Vg=K_{DNA}(A_{260}-\alpha A_{280})/L \text{ or } (A_{260}-\alpha A_{280})=VgL/K_{DNA}$$

$$Cp=K_{protein}(A_{280}-A_{260}/\beta)/L \text{ or } (A_{280}-A_{260}/\beta)=CpL/K_{protein}$$

where $$K_{DNA}=\frac{1}{\varepsilon_{DNA260}\,(1-\alpha/\beta)}$$

$$K_{protein}=\frac{1}{\varepsilon_{protein280}\,(1-\alpha/\beta)}$$

The equations above allow slope spectroscopy to be performed by plotting ($A_{260}-\alpha\ A_{280}$) or ($A_{280}-A_{260}/\beta$) against the path length L. The slopes, $S_{DNA}$ and $S_{protein}$ can be obtained from linear regression analysis, then the vector genome titer and capsid titer can be determined from the slopes $$Vg=K_{DNA}S_{DNA}$$

$$Cp=K_{protein}S_{protein}$$

i) an HPLC Method to Measure GC Titer and Capsid Titer

Two equations in section h) above used to calculate vector genome titer and capsid titer can be further adapted to HPLC with UV detection to determine the AAV vector genome titer and capsid titer. At any moment in the HPLC UV detector, the UV absorbance still follows the Beer-Lambert law and two equations used to calculate the AAV vector genome titer and capsid in section h) are still applicable. Assuming the flow cell volume of the UV detector is dV (e.g. dV may be generated by well-known methods to the skilled artisan), then the number of vector genome copies (Nvg) and the number of capsid particles (Ncp) at one moment t are $$Nvg = Vg\__t dV = [K_{DNA}(A_{260\_t} - \alpha A_{280\_t})/L]dV$$

$$Ncp = Cp\__t dV = [K_{protein}(A_{260\_t} - A_{260\_t}/\beta)/L]dV$$

At any moment, the samples detected by UV and thus filled the UV detector volume dV is determined by the flow rate (f) and a period of time dt:

$$dV = fdt$$

The total number of vector genome copies (Tvg) for an HPLC peak of AAV can be determined by the integration of $\int Vg\_t\ dV$ or $$T_{vg} = \int [K_{DNA}(A_{260\_t} - \alpha A_{280\_t})/L]fdt$$

$$T_{vg} = fK_{DNA}(\int A_{260\_t}dt - \alpha \int A_{280\_t}dt)/L$$

$\int A_{260\_t}$ dt equals to the peak area at 260 nm ($Peak_{260}$), while $\int A_{280\_t}$ dt equals to the peak area at 280 nm ($Peak_{280}$), thus $$Tvg = fK_{DNA}(Peak_{260} - \alpha Peak_{280})/L$$

For an HPLC injection volume u, the vector genome titer (Vg) determined by HPLC is $$Vg = Tvg/u$$

$$Vg = fK_{DNA}(Peak_{260} - \alpha Peak_{280})/(uL)$$

Similarly, the capsid titer (Cp) determined by HPLC is $$Cp = fK_{protein}(Peak_{280} - Peak_{260}/\beta)/(uL)$$

In conventional quantitative analysis by HPLC, a calibration curve has to be generated using standard molecules sharing similar, if not identical, molecular properties as the analytes. For two components or multicomponent molecules or systems, calibration curves cannot be generated, because the composition of such molecules or systems is not fixed, but variable, resulting in differences in UV absorbance. Uniquely, using the example method described here with the above equations, samples can be quantitated via peak area with detection at two wavelengths. No calibration curve is needed in quantitative analysis. Using this method, the HPLC systems can be operated very similarly to a spectrophotometer. System suitability and instrument calibration require only a standard to assess functionality of the instrument. The HPLC method described here is an absolute quantification method, in comparison with conventional relative quantification methods using a calibration curve. An advantage of absolute HPLC quantification described here over spectrophotometer quantification is the reduction of matrix interference and specific for analytes. Buffer or matrix components that interfere with the UV absorbance measurement can be separated from the analytes by HPLC methods.

This absolute quantitation technique can be performed for all modes of chromatography, including but not limited to size exclusion high performance chromatography (SEC-HPLC), ion exchange high performance chromatography (IE-HPLC), affinity and reversed phase high performance chromatography (RP-HPLC). The quantitation is accurate as long as there is complete sample recovery with high peak purity, stable baseline, accurate injection volumes and flow-rates. The method is capable of quantitating other two-component molecules or systems.

Fluctuating baselines are inherent to most chromatography methods due to many factors including refractive index change, mobile phase composition, inconsistent flow rate and pressure. Consistent and accurate integration of the baseline is useful for accurate quantitation of AAV GC titer and capsid titer using this method. Two methods can be used to correct baseline fluctuations. The first method utilizes baseline subtraction to remove baseline interference from non-analyte. Before or after each sample injection, a blank sample injection is performed. The peak area used in quantification calculation is the one after blank subtraction. Alternatively, a series of injections of different amounts of samples can be performed to generate a linear curve. The adjusted peak area is the one after subtraction of the intercept of the linear curve.

Mobile phases are used for all chromatography methods (SEC-HPC, RP-HPLC, IE-HPLC, Affinity). Changes in buffer composition, ionic strength and pH may affect the extinction coefficient and subsequently the final results. Thus, it is necessary to experimentally determine the extinction coefficient within the mobile phase in order to provide accurate results. This can be done by comparing the UV absorbance in the HPLC mobile phases to the UV absorbance in the solution that the UV coefficient is determined. A correction factor, i.e., the ratio of UV absorbance in the HPLC mobile phases to the UV absorbance in the solution that the UV coefficient is determined, may be applied if any discrepancy is found.

The HPLC absolute quantitation method described here is based on precise flow cell path length and wavelength accuracy, well-defined solvent compression ratio, precise flow rates and injection volumes. Instead of checking the accuracy of every instrument parameter, a simple procedure can be performed to check and to apply a correction factor to HPLC system for absolute quantification. A reference standard, which has a known concentration determined by either spectrophotometry or other methods, can be injected before and/or after the sample analysis. The concentration determined by the HPLC absolute quantification method is compared to the standard concentration. A correction factor Kc, which is the ratio of determined standard concentration by HPLC and the known standard concentration, may be applied as shown below if any discrepancy is discovered.

$$Vg = KcfK_{DNA}(Peak_{260} - \alpha Peak_{280})/(uL)$$

$$Cp = KcfK_{protein}(Peak_{280} - Peak_{260}/\beta)/(uL)$$

The discrepancy or the correction factor may be instrument dependent, not analyte dependent. Thus, a standard can be any substance, such as bovine serum albumin (BSA), for AAV analysis or any analysis of other types of molecules. The correction factor for an HPLC instrument can remain constant for a few days or a few weeks without significant changes, which could be utilized to decrease the frequency of instrument suitability checking or instrument calibration checking. Furthermore, similar types of HPLC systems with the same type of UV detector were found to have roughly the same correction factor.

Similarly, the absolute quantification method by HPLC described above can be applied to molecules or systems of single component with a definite UV extinction coefficient. After similar deduction starting from the Beer-Lambert law, the absolute quantification by HPLC to calculate the concentration using peak area ($Peak_{wavelength}$) and UV extinction coefficient ($\varepsilon_{wavelength}$) at a specific wavelength is, $$C_{molecule} = KcfPeak_{wavelength}/(uL\varepsilon_{wavelength})$$

j) SEC-HPLC Method to Measure Absolute Vector Genome Titer and Capsid Titer

The absolute quantification method by HPLC described above was used to determine the vector genome titers of AAV products. The sample was analyzed by SEC-HPLC using a Sepax SRT SEC-500 column and an Agilent 1260 bio-inert Infinity II HPLC system with a diode array detector with a 60 mm path length flow cell. The vector genome titer and capsid titer were determined using the two equations discussed above in section i).

Figure 10A:
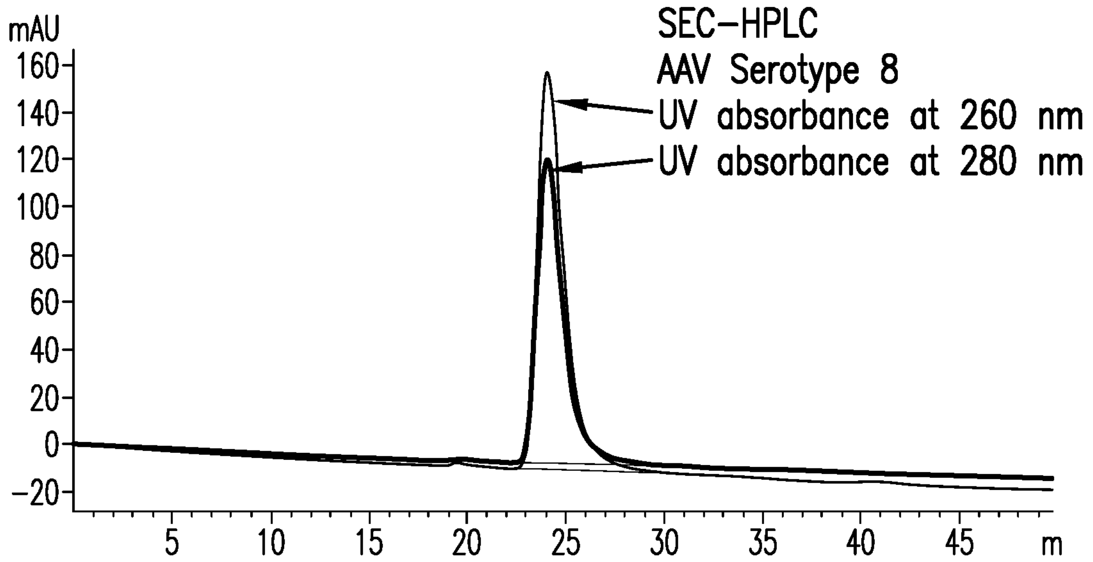
FIG. 10A illustrates a representative SEC-HPLC chromatogram of AAV serotype 8 and FIG. 10B illustrates a representative spectrum of AAV serotype 8 by spectrophotometer.
Figure 10B:
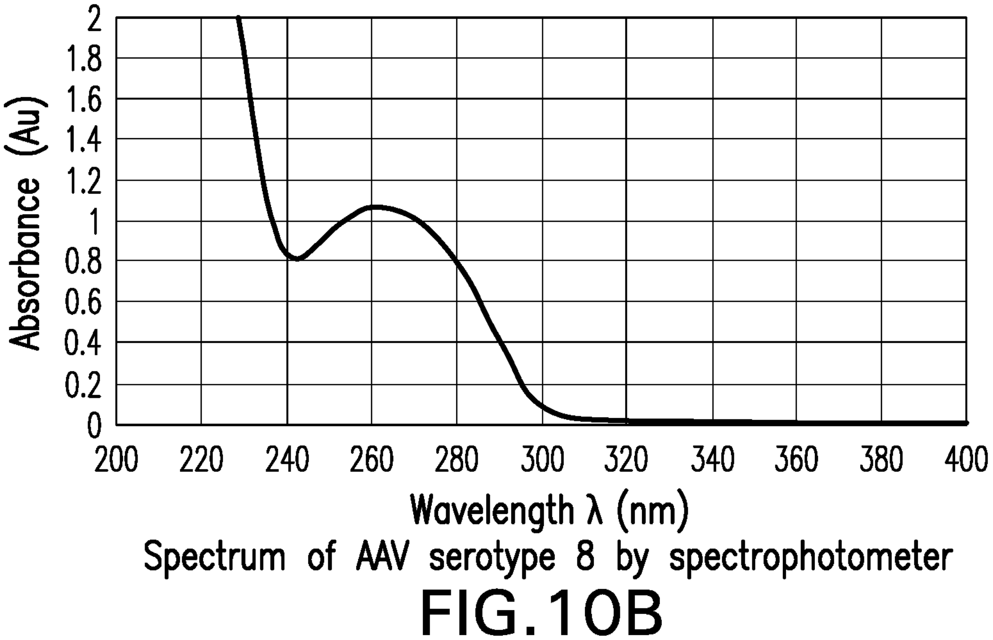

An AAV serotype 8 sample (1.50 E+13 GC/mL by spectrophotometry) was injected onto the Agilent HPLC system. Another aliquot from the same AAV sample was analyzed simultaneously with the HPLC analysis on an Agilent Cary 60 UV-Vis spectrophotometer using a 1 cm path length quartz cuvette. The AAV vector genome titer and capsid titer were determined by absolute HPLC quantification and spectrophotometry. The standard extinction coefficient of ssDNA (0.027 $(\mu g/mL)^{-1}cm^{-1}$) and the extinction coefficient of protein capsid calculated by Pace's method (Pace, C. N., Vajdos, F., Fee, L., Grimsley, G., and Gray, T. 1995. How to measure and predict the molar absorbance coefficient of a protein. Prot. Sci. 4:2411-2423.) were used for calculation in both spectrophotometry quantification and absolute HPLC quantification. The instrument correction factor of 1.10 determined previously using DNA standards was applied to the quantitation. FIGS. 10A and 10B show the HPLC chromatogram and UV spectra for the analysis of AAV, respectively. The results are summarized in Table 4A and Table 4B. The results obtained using both the SEC-HPLC and UV spectrophotometry methods were highly agreeable, with the difference between these two methods less than 5.0% and 10% for capsid titer and vector genome titer, respectively. The agreement between these two methods demonstrates the accuracy and reliability of the absolute quantification by HPLC, although the difference is slightly larger than that observed with single component systems, such as proteins and DNA as discussed in the section k) and 1). The slightly larger difference in concentration determination of two component molecules or systems could be attributable to the differences in the spectrophotometer and HPLC detectors. For example, the wavelength accuracy of HPLC UV detectors is far less than that of a spectrophotometer, which may cause larger errors for two component molecules, because two wavelengths are used for absolute quantification by HPLC and usually only one wavelength is at the maximum absorbance.

TABLE 4A

Quantification of AAV serotype 8 capsid titer by SEC-HPLC

| AAV Testing # | Capsid Titer by HPLC (Capsid/mL) | Capsid Titer by Spectrophotometry (Capsid/mL) | Relative Difference between Two Methods |
|---|---|---|---|
| 1 | $2.69 \times 10^{13}$ | $2.67 \times 10^{13}$ | 0.9% |
| 2 | $2.72 \times 10^{13}$ | $2.67 \times 10^{13}$ | 1.8% |
| 3 | $2.76 \times 10^{13}$ | $2.67 \times 10^{13}$ | 3.3% |
| Average | $2.72 \times 10^{13}$ | $2.67 \times 10^{13}$ | 2.0% |
| % Relative Standard Deviation | 1.3% | NA | NA |

Note that NA stands for Not Applicable.

TABLE 4B

Quantification of AAV serotype 8 vector genome titer by SEC-HPLC

| Sample | HPLC GC/mL Result | Capsid Titer by Spectrophotometry (GC/mL) | Relative Difference between Two Methods |
|---|---|---|---|
| AAV | $1.42 \times 10^{13}$ | $1.50 \times 10^{13}$ | −5.4% |
| AAV | $1.41 \times 10^{13}$ | $1.50 \times 10^{13}$ | −6.1% |
| AAV | $1.42 \times 10^{13}$ | $1.50 \times 10^{13}$ | −5.6% |
| Average | $1.42 \times 10^{13}$ | $1.50 \times 10^{13}$ | −5.7% |
| % Relative Standard Deviation | 0.4% | NA | NA |

k) the HPLC Absolute Quantification Method is Applicable to Protein Concentration Determination The absolute quantification method by HPLC described above was used to determine the vector genome titers of AAV products. The sample was analyzed by SEC-HPLC using a Sepax SRT SEC-500 column and an Agilent 1260 bio-inert Infinity II HPLC system with a diode array detector with a 60 mm path length flow cell. The concentration is determined using the following equation adapted for protein analysis from the equation in the section i) above.

$$C_{protein}=Kc\text{Peak}_{280\ nm}f/(\varepsilon_{protein}Lu)$$

where $C_{protein}$ is protein concentration; Kc is the correction factor for the Agilent 1260 bio-inert Infinity II HPLC system; f is flow rate; $\text{Peak}_{280}$ is peak area detected at 280 nm; $\varepsilon_{protein}$ is the UV extinction coefficient of the protein; u is injection volume, and L is the flow cell path length.

A bovine serum albumin (BSA) sample (2 mg/mL, Thermo Scientific) was injected onto the Agilent HPLC system. Another aliquot from the same BSA sample was analyzed simultaneously with the HPLC analysis on an Agilent Cary 60 UV-Vis spectrophotometer using a quartz cuvette of 1 cm path length. The standard molar extinction coefficient of BSA (43824 $M^{-1}cm^{-1}$) was used for calculation of protein concentration in both spectrophotometry quantification and absolute HPLC quantification. The instrument correction factor of 1.06 determined previously using BSA was applied to the quantitation. The results are summarized in Table 5. The results obtained using both the SEC-HPLC and UV spectrophotometry methods were highly agreeable. The differences between the two methods were less than 0.9% demonstrating the accuracy and reliability of the quantification method.

TABLE 5

Quantification of Bovine Serum Albumin by Spectrophotometry and SEC-HPLC analysis

| BSA Testing | SEC-HPLC Result (mg/mL) | Spectrophotometry Result (mg/mL) | Relative Difference between Two Methods |
|---|---|---|---|
| 1 | 1.982 | 2.000 | 0.9% |
| 2 | 1.995 | 2.000 | 0.2% |
| 3 | 2.002 | 2.000 | 0.1% |
| Average | 1.993 | 2.000 | 0.4% |
| % Relative Standard Deviation | 0.50 | 0.00 | NA |

l) the HPLC Absolute Quantification Method is Applicable to DNA Concentration Determination The absolute HPLC quantification method described above was used to determine DNA concentration. The sample was analyzed by SEC-HPLC using a Sepax SRT SEC-2000 column and an Agilent 1260 Infinity II HPLC system with a diode array detector with a 60 mm path length flow cell. The concentration is determined using the following equation adapted for DNA analysis from the equation in the section i).

$$C_{DNA}=Kcf\text{Peak}_{260}/(\varepsilon_{DNA}uL)$$

where $C_{DNA}$ is concentration; Kc is the correction factor for the Agilent 1260 Infinity II HPLC system; f is flow rate; $\text{Peak}_{260}$ is peak area detected at 260 nm; $\varepsilon_{DNA}$ is the UV extinction coefficient for dsDNA; u is injection volume, and L is the flow cell path length.

Figure 11A:
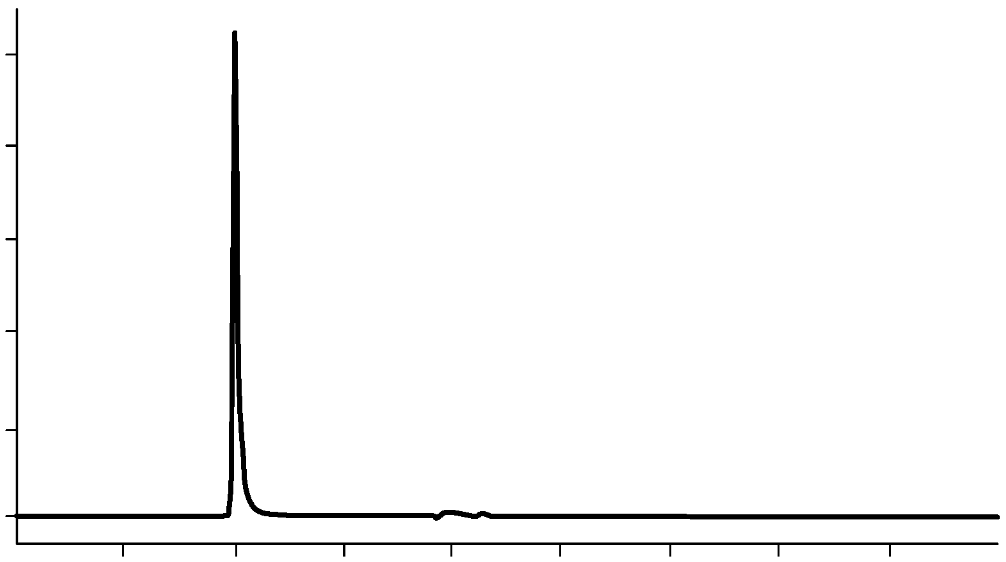
FIGS. 11A and 11B, respectively, illustrate 4000 bp DNA fragment analyzed on Agilent 1260 Infinity II HPLC system using a Sepax SRT SEC-2000 column and on Agilent Cary 60 UV spectrophotometer.
Figure 11B:
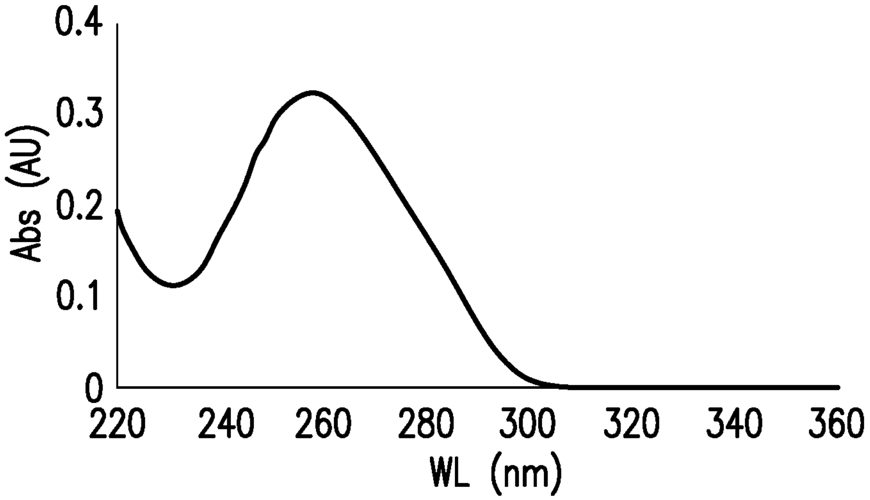

A 4000 bp DNA fragment (0.5 g/mL, Thermo Scientific) was diluted 40-fold with SEC mobile phase. An aliquot was injected onto the Agilent HPLC system. Another aliquot from the same 40-fold diluted 4000 bp DNA fragment was analyzed simultaneously with the HPLC analysis on an Agilent Cary 60 UV-Vis spectrophotometer using a 50 μL quartz cuvette of 1 cm path length. Concentration of the DNA fragment was determined based on the Beer-Lambert's law. The standard extinction coefficient for dsDNA (0.020 $(\mu g/mL)^{-1}cm^{-1}$) was used for calculation in both spectrophotometry quantification and absolute HPLC quantification. The instrument correction factor of 1.06 determined previously using BSA. FIGS. 11A and 11B show a representative chromatogram and UV spectra for the analysis of the 4000 bp DNA fragments. The same approach was also applied to the quantification of the 2000 bp and 700 bp DNA fragments (Thermo Scientific), and the results are summarized in Table 6. The results are highly agreeable using both the SEC-HPLC and UV spectrophotometry methods with differences between these two methods less than 5.6%, demonstrating accuracy and reliability of the absolute quantification by HPLC even though the correction factor of a different HPLC system was used.

TABLE 6

Quantification of DNA fragments using UV spectrophotometry and SEC-HPLC

| DNA Fragments | Concentration by Spectrophotometry (μg/mL) | Concentration by SEC-HPLC (μg/mL) | Relative difference between two methods |
|---|---|---|---|
| 4000 bp | 16.0 | 15.1 | 5.6% |
| 2000 bp | 14.8 | 14.7 | 0.4% |
| 700 bp | 12.8 | 12.4 | 3.1% |

Absolute quantification of DNA by SEC-HPLC described above can be utilized to determine the vector genome titer of AAV or other virus. First the vector genome of AAV is released by incubation with, e.g., 0.05% SDS at high temperature to dissociate the capsids. The exact denaturation condition for AAV products was optimized empirically and individually for each AAV product. Then the released vector genome is separated from the capsid proteins by SEC-HPLC, allowing for absolute quantification of vector genome titer by HPLC UV detection. An experiment (Table 7) shows that AAV vector genome titer determined by SEC-HPLC was in agreement with the vector genome titers determined by ddPCR.

TABLE 7

Example of comparison of AAV vector genome titer determined using ddPCR and SEC-HPLC

| Sample ID | VGC by SEC-HPLC (GC/mL) | VGC by ddPCR (GC/mL) | Relative difference between Two Methods |
|---|---|---|---|
| 1 | $5.10\times10^{12}$ | $4.80\times10^{12}$ | 6.1% |
| 2 | $6.40\times10^{12}$ | $5.90\times10^{12}$ | 8.1% |
| 3 | $2.75\times10^{13}$ | $2.50\times10^{13}$ | 9.5% |
| 4 | $1.12\times10^{13}$ | $1.10\times10^{13}$ | 1.8% |

m) the HPLC Absolute Quantification Method can be Used to Determine the Content of Other Biomolecules and Small Molecules The absolute quantification by HPLC is applicable to determine the concentrations of other biomolecules and small molecules using the equation in the section i).

$$C_{molecule}=Kcf\text{Peak}_{wavelength}/(uL\varepsilon_{wavelength})$$

where a correction factor Kc, which is the ratio of the standard concentration determined by HPLC and the known concentration of the standard, should be determined for a specific HPLC system, and the UV extinction coefficient at specific wavelength should be determined for specific solvents used in the HPLC analysis. Accurate peak area improves absolute content quantification. Similar background subtraction techniques described in the section i) can be used to accurately determine the peak area.

n) Determination of Capsid Titer by SEC-214 Method

The quantitation utilizes a calibration curve of AAV capsids that contain capsids lacking the genome (empty capsids). The concentration of empty capsid standards is determined using traditional Beer-Lambert law, which in general is considered to be an accurate method within 10% error to the true values. UV acquisition at the wavelength of 214 nm is employed.

Relative UV absorption by DNA is significantly reduced at 214 nm (>⅙th absorption at 214 nm for AAV). The small portion of UV absorbance contributed by genome DNA is corrected by estimating through $A_{260}/A_{280}$. A linear trendline is used in the following equations to assess the capsid titers.

$$\text{Capsid titer}=m(\text{Total Sample Absorbance @214 nm}-(\text{Total DNA Absorbance @ 214 nm}))-b$$

or $$\text{Capsid titer}=m(A214AAV-K(A260AAV-0.590A280AAV))-b$$

m=Slope of empty capsid linear regression

A214, A260, A280=Peak area at UV 214, 260 and 280 nm wavelengths

K—A factor related to A214/A260 ratio of DNA b=y-intercept of empty calibration curve.

Using the example method described herein with above equations, samples can be quantitated via peak area at specific wavelength. No calibration curve is needed in quantitative analysis.

Using this method, the HPLC UV detector is operated very much like a spectrophotometer. System suitability and calibration require only a standard to assess functionality of the instrument. The HPLC method described in this disclosure is an absolute quantification method, in comparison with conventional relative quantification methods using a calibration curve. An advantage of absolute HPLC quantification described here over spectrophotometer quantification is the reduction of matrix interference. Buffer or matrix components that interfere with the UV absorbance measurement can be separated from the analyses by HPLC methods. Another advantage of absolute HPLC quantification over spectrophotometry is a significant increase in sensitivity due to low volume injection that can be achieved.

An example of application of the methods described herein is to measure the drug content of therapeutic proteins, including therapeutic mAb. Therapeutic protein concentration and in-process titers are usually determined by UV absorbance at 280 nm or by affinity chromatography or RP-HPLC with a calibration curve. Using the absolute quantification method by HPLC, the protein content can be directly determined by the peak area at 280 nm. Neither series dilution with UV absorbance method at 280 nm nor a calibration curve with conventional HPLC methods is needed with the absolute quantification method by HPLC. All HPLC modes, including SEC-HPLC, IE-HPLC, RP-HPLC, affinity chromatography, can be used for protein content determination.

Recombinant AAV Particles

The provided methods are suitable for use in the production of any isolated recombinant AAV particles, in the production of a composition comprising any isolated recombinant AAV particles, or in the method for treating a disease or disorder in a subject in need thereof comprising the administration of any isolated recombinant AAV particles. As such, the rAAV may be of any serotype, modification, or derivative, known in the art, or any combination thereof (e.g., a population of rAAV particles that comprises two or more serotypes, e.g., comprising two or more of rAAV2, rAAV8, and rAAV9 particles) known in the art. In some embodiments, the rAAV particles are AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other rAAV particles, or combinations of two or more thereof.

In some embodiments, rAAV particles have a capsid protein from an AAV serotype selected from AAV1, AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, rAAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise a capsid protein from an AAV capsid serotype selected from AAV1, AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16, or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise the capsid of Anc80 or Anc80L65, as described in Zinn et al., 2015, Cell Rep. 12 (6): 1056-1068, which is incorporated by reference in its entirety. In certain embodiments, the rAAV particles comprise the capsid with one of the following amino acid insertions: LGETTRP or LALGETTRP, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise the capsid of AAV.7m8, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise any AAV capsid disclosed in U.S. Pat. No. 9,585,971, such as AAV-PHP.B. In some embodiments, rAAV particles comprise any AAV capsid disclosed in U.S. Pat. No. 9,840,719 and WO 2015/013313, such as AAV.Rh74 and RHM4-1, each of which is incorporated herein by reference in its entirety. In some embodiments, rAAV particles comprise any AAV capsid disclosed in WO 2014/172669, such as AAV rh.74, which is incorporated herein by reference in its entirety. In some embodiments, rAAV particles comprise the capsid of AAV2/5, as described in Georgiadis et al., 2016, Gene Therapy 23:857-862 and Georgiadis et al., 2018, Gene Therapy 25:450, each of which is incorporated by reference in its entirety. In some embodiments, rAAV particles comprise any AAV capsid disclosed in WO 2017/070491, such as AAV2tYF, which is incorporated herein by reference in its entirety. In some embodiments, rAAV particles comprise the capsids of AAVLK03 or AAV3B, as described in Puzzo et al., 2017, Sci. Transl. Med. 29 (9): 418, which is incorporated by reference in its entirety. In some embodiments, rAAV particles comprise any AAV capsid disclosed in U.S. Pat. Nos. 8,628,966; 8,927,514; 9,923,120 and WO 2016/049230, such as HSC1, HSC2, HSC3, HSC4, HSC5, HSC6, HSC7, HSC8, HSC9, HSC10, HSC11, HSC12, HSC13, HSC14, HSC15, or HSC16, each of which is incorporated by reference in its entirety.

In some embodiments, rAAV particles comprise an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335.

In some embodiments, rAAV particles have a capsid protein disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689, (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10), the contents of each of which is herein incorporated by reference in its entirety. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689 (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10).

Nucleic acid sequences of AAV based viral vectors and methods of making recombinant AAV and AAV capsids are taught, for example, in U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; International Patent Application Nos. PCT/US2015/034799; PCT/EP2015/053335; WO 2003/052051, WO 2005/033321, WO 03/042397, WO 2006/068888, WO 2006/110689, WO2009/104964, WO 2010/127097, and WO 2015/191508, and U.S. Appl. Publ. No. 20150023924.

The provided methods are suitable for used in the production of recombinant AAV encoding a transgene. In some embodiments, provided herein are rAAV viral vectors encoding an anti-VEGF Fab. In specific embodiments, provided herein are rAAV8-based viral vectors encoding an anti-VEGF Fab. In more specific embodiments, provided herein are rAAV8-based viral vectors encoding ranibizumab. In some embodiments, provided herein are rAAV viral vectors encoding Iduronidase (IDUA). In specific embodiments, provided herein are rAAV9-based viral vectors encoding IDUA. In some embodiments, provided herein are rAAV viral vectors encoding Iduronate 2-Sulfatase (IDS). In specific embodiments, provided herein are rAAV9-based viral vectors encoding IDS. In some embodiments, provided herein are rAAV viral vectors encoding a low-density lipoprotein receptor (LDLR). In specific embodiments, provided herein are rAAV8-based viral vectors encoding LDLR. In some embodiments, provided herein are rAAV viral vectors encoding tripeptidyl peptidase 1 (TPP1) protein In specific embodiments, provided herein are rAAV9-based viral vectors encoding TPP.

In additional embodiments, rAAV particles comprise a pseudotyped AAV capsid. In some embodiments, the pseudotyped AAV capsids are rAAV2/8 or rAAV2/9 pseudotyped AAV capsids. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In some embodiments, the capsid protein is a chimeric of 2 or more AAV capsid proteins from AAV serotypes selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2YF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In certain embodiments, a single-stranded AAV (ssAAV) can be used. In certain embodiments, a self-complementary vector, e.g., scAAV, can be used (see, e.g., Wu, 2007, Human Gene Therapy, 18 (2): 171-82, McCarty et al, 2001, Gene Therapy, Vol. 8, Number 16, Pages 1248-1254; and U.S. Pat. Nos. 6,596,535; 7,125,717; and 7,456,683, each of which is incorporated herein by reference in its entirety).

In some embodiments, rAAV particles in the clarified feed comprise a capsid protein from an AAV capsid serotype selected from AAV-8 or AAV-9. In some embodiments, the rAAV particles have an AAV capsid serotype of AAV-1 or a derivative, modification, or pseudotype thereof. In some embodiments, the rAAV particles have an AAV capsid serotype of AAV-4 or a derivative, modification, or pseudotype thereof. In some embodiments, the rAAV particles have an AAV capsid serotype of AAV-5 or a derivative, modification, or pseudotype thereof. In some embodiments, the rAAV particles have an AAV capsid serotype of AAV-8 or a derivative, modification, or pseudotype thereof. In some embodiments, the rAAV particles have an AAV capsid serotype of AAV-9 or a derivative, modification, or pseudotype thereof.

In some embodiments, rAAV particles in the clarified feed comprise a capsid protein that is a derivative, modification, or pseudotype of AAV-8 or AAV-9 capsid protein. In some embodiments, rAAV particles in the clarified feed comprise a capsid protein that has an AAV-8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-8 capsid protein.

In some embodiments, rAAV particles in the clarified feed comprise a capsid protein that is a derivative, modification, or pseudotype of AAV-9 capsid protein. In some embodiments, rAAV particles in the clarified feed comprise a capsid protein that has an AAV-8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-9 capsid protein.

In additional embodiments, rAAV particles in the clarified feed comprise a mosaic capsid. Mosaic AAV particles are composed of a mixture of viral capsid proteins from different serotypes of AAV. In some embodiments, rAAV particles in the clarified feed comprise a mosaic capsid containing capsid proteins of a serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, rAAV particles in the clarified feed comprise a mosaic capsid containing capsid proteins of a serotype selected from AAV-1, AAV-2, AAV-5, AAV-6, AAV-7, AAV-8, AAV-9, AAV-10, AAVrh.8, and AAVrh.10.

In additional embodiments, rAAV particles in the clarified feed comprise a pseudotyped rAAV particle. In some embodiments, the pseudotyped rAAV particle comprises (a) a nucleic acid vector comprising AAV ITRs and (b) a capsid comprised of capsid proteins derived from AAVx (e.g., AAV-1, AAV-3, AAV-4, AAV-5, AAV-6, AAV-7, AAV-8, AAV-9, AAV-10 AAV-11, AAV-12, AAV-13, AAV-14, AAV-15 and AAV-16). In additional embodiments, rAAV particles in the clarified feed comprise a pseudotyped rAAV particle comprised of a capsid protein of an AAV serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2YF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In additional embodiments, rAAV particles in the clarified feed comprise a pseudotyped rAAV particle containing AAV-8 capsid protein. In additional embodiments, rAAV particles in the clarified feed comprise a pseudotyped rAAV particle is comprised of AAV-9 capsid protein. In some embodiments, the pseudotyped rAAV8 or rAAV9 particles are rAAV2/8 or rAAV2/9 pseudotyped particles. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles in the clarified feed comprise a capsid containing a capsid protein chimeric of two or more AAV capsid serotypes. In further embodiments, the capsid protein is a chimeric of 2 or more AAV capsid proteins from AAV serotypes selected from AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, rAAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In further embodiments, the capsid protein is a chimeric of 2 or more AAV capsid proteins from AAV serotypes selected from AAV-1, AAV-2, AAV-5, AAV-6, AAV-7, AAV-8, AAV-9, AAV-10, AAVrh.8, and AAVrh.10.

In some embodiments, the rAAV particles comprise an AAV capsid protein chimeric of AAV-8 capsid protein and one or more AAV capsid proteins from an AAV serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein chimeric of AAV-8 capsid protein and one or more AAV capsid proteins from an AAV serotype selected from AAV-1, AAV-2, AAV-5, AAV-6, AAV-7, AAV-9, AAV-10, AAVrh.8, and AAVrh.10.

In some embodiments, the rAAV particles comprise an AAV capsid protein chimeric of AAV-9 capsid protein the capsid protein of one or more AAV capsid serotypes selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, the rAAV particles comprise an AAV capsid protein chimeric of AAV-9 capsid protein the capsid protein of one or more AAV capsid serotypes selected from AAV1, AAV2, AAV3, AAV4, AAV5, AA6, AAV7, AAV8, AAV9, AAVrh.8, and AAVrh.10.

Methods for Isolating rAAV

In some embodiments, the disclosure provides methods for producing a pharmaceutical composition comprising isolated recombinant adeno-associated virus (rAAV) particles, comprising isolating rAAV particles from a feed comprising an impurity, determining the genome titer (Vg), capsid titer (Cp), and/or percentage vector genome copies per capsid (Vg %) of the isolated rAAV particles using a method disclosed herein, and formulating the isolated rAAV particles to produce a pharmaceutical composition.

In some embodiments, the disclosure further provides methods for producing a pharmaceutical unit dosage comprising isolated recombinant adeno-associated virus (rAAV) particles, comprising isolating rAAV particles from a feed comprising an impurity, determining the genome titer (Vg), capsid titer (Cp), and/or percentage vector genome copies per capsid (Vg %) of the isolated rAAV particles using a method disclosed herein, and formulating the isolated rAAV particles.

Numerous methods are known in the art for production of rAAV particles, including transfection, stable cell line production, and infectious hybrid virus production systems which include Adenovirus-AAV hybrids, herpesvirus-AAV hybrids and baculovirus-AAV hybrids. rAAV production cultures for the production of rAAV virus particles all require; (1) suitable host cells, including, for example, human-derived cell lines such as HeLa, A549, or 293 cells, or insect-derived cell lines such as SF-9, in the case of baculovirus production systems; (2) suitable helper virus function, provided by wild type or mutant adenovirus (such as temperature sensitive adenovirus), herpes virus, baculovirus, or a plasmid construct providing helper functions; (3) AAV rep and cap genes and gene products; (4) a transgene (such as a therapeutic transgene) flanked by AAV ITR sequences; and (5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), and Sf-900 II SFM media as described in U.S. Pat. No. 6,723,551, which is incorporated herein by reference in its entirety.

rAAV production cultures can routinely be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, 293, and SF-9 cells which can be cultured in a variety of ways including, for example, spinner flasks, stirred tank bioreactors, and disposable systems such as the Wave bag system. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety.

In some embodiments, rAAV particles are produced as disclosed in U.S. Provisional Application No. 62/717,212, filed on Aug. 10, 2018, titled "SCALABLE METHOD FOR RECOMBINANT AAV PRODUCTION," which is incorporated herein by reference in its entirety.

Recombinant AAV particles can be harvested from rAAV production cultures by harvest of the production culture comprising host cells or by harvest of the spent media from the production culture, provided the cells are cultured under conditions known in the art to cause release of rAAV particles into the media from intact host cells. Recombinant AAV particles can also be harvested from rAAV production cultures by lysis of the host cells of the production culture. Suitable methods of lysing cells are also known in the art and include for example multiple freeze/thaw cycles, sonication, microfluidization, and treatment with chemicals, such as detergents and/or proteases.

At harvest, rAAV production cultures can contain one or more of the following: (1) host cell proteins; (2) host cell DNA; (3) plasmid DNA; (4) helper virus; (5) helper virus proteins; (6) helper virus DNA; and (7) media components including, for example, serum proteins, amino acids, transferrins and other low molecular weight proteins.

In some embodiments, the rAAV production culture harvest is clarified to remove host cell debris. In some embodiments, the production culture harvest is clarified by filtration through a series of depth filters. Clarification can also be achieved by a variety of other standard techniques known in the art, such as, centrifugation or filtration through any cellulose acetate filter of 0.2 mm or greater pore size known in the art.

In some embodiments, the production culture harvest is clarified by filtration are disclosed in U.S. Provisional Application No. 62/664,254, filed on Apr. 29, 2018, titled "SCALABLE CLARIFICATION PROCESS FOR RECOMBINANT AAV PRODUCTION," and 62/671,968 filed on May 15, 2018, titled "SCALABLE CLARIFICATION PROCESS FOR RECOMBINANT AAV PRODUCTION," each of which is incorporated herein by reference in its entirety.

In some embodiments, the rAAV production culture harvest is treated with a nuclease (e.g., Benzonase®) or endonuclease (e.g., endonuclease from *Serratia marcescens*) to digest high molecular weight DNA present in the production culture. The nuclease or endonuclease digestion can routinely be performed under standard conditions known in the art. For example, nuclease digestion is performed at a final concentration of 1-2.5 units/ml of Benzonase® at a temperature ranging from ambient to 37° C. for a period of 30 minutes to several hours.

Recombinant AAV particles can be isolated from the clarified harvest by any method known in the art. In some embodiments, the methods of isolating rAAV particles from the clarified harvest disclosed herein comprise the use of one or more of tangential flow filtration, affinity chromatography, size exclusion chromatography, ion exchange chromatography, hydroxylapatite chromatography, and hydrophobic interaction chromatography. In some embodiments, a method disclosed herein includes at least 2, at least 3, or at least 4 of: tangential flow filtration, affinity chromatography, anion exchange chromatography, hydrophobic interaction chromatography, size exclusion chromatography, or sterile filtration. In some embodiments, a method disclosed herein further includes tangential flow filtration. In some embodiments, a method disclosed herein includes sterile filtration. In further embodiments, a method disclosed herein includes tangential flow filtration and sterile filtration.

In some embodiments, the clarified harvest is concentrated via tangential flow filtration ("TFF") before being applied to a chromatographic medium, for example, affinity chromatography medium. Large scale concentration of viruses using TFF ultrafiltration has been described by Paul et al., Human Gene Therapy 4:609-615 (1993). TFF concentration of the clarified harvest enables a technically manageable volume of clarified harvest to be subjected to chromatography and allows for more reasonable sizing of columns without the need for lengthy recirculation times. In some embodiments, the clarified harvest is concentrated between at least two-fold and at least ten-fold. In some embodiments, the clarified harvest is concentrated between at least ten-fold and at least twenty-fold. In some embodiments, the clarified harvest is concentrated between at least twenty-fold and at least fifty-fold. In some embodiments, the clarified harvest is concentrated about twenty-fold. One of ordinary skill in the art will also recognize that TFF can also be used to remove small molecule impurities (e.g., cell culture contaminants comprising media components, serum albumin, or other serum proteins) form the clarified harvest via diafiltration. In some embodiments, the clarified harvest is subjected to diafiltration to remove small molecule impurities. In some embodiments, the diafiltration comprises the use of between about 3 and about 10 diafiltration volume of buffer. In some embodiments, the diafiltration comprises the use of about 5 diafiltration volume of buffer. One of ordinary skill in the art will also recognize that TFF can also be used at any step in the purification process where it is desirable to exchange buffers before performing the next step in the purification process. In some embodiments, the methods for isolating rAAV from the clarified harvest disclosed herein comprise the use of TFF to exchange buffers.

Affinity chromatography can be used to isolate rAAV particles from a composition. In some embodiments, affinity chromatography is used to isolate rAAV particles from the clarified harvest. In some embodiments, affinity chromatography is used to isolate rAAV particles from the clarified harvest that has been subjected to tangential flow filtration. Suitable affinity chromatography media are known in the art and include without limitation, AVB Sepharose™, POROS™ CaptureSelect™ AAV9 affinity resin, and POROS™ CaptureSelect™ AAV8 affinity resin. In some embodiments, the affinity chromatography media is POROS™ CaptureSelect™ AAV9 affinity resin.

Anion exchange chromatography can be used to isolate rAAV particles from a composition. In some embodiments, anion exchange chromatography is used after affinity chromatography as a final concentration and polish step. Suitable anion exchange chromatography media are known in the art and include without limitation, Unosphere Q (Biorad, Hercules, Calif.), and N-charged amino or imino resins such as e.g., POROS 50 PI, or any DEAE, TMAE, tertiary or quaternary amine, or PEI-based resins known in the art (U.S. Pat. No. 6,989,264; Brument et al., Mol. Therapy 6 (5): 678-686 (2002); Gao et al., Hum. Gene Therapy 11:2079-2091 (2000)). In some embodiments, the anion exchange chromatography media comprises a quaternary amine. In some embodiments, the anion exchange chromatography media is BIA QA. In some embodiments, the anion exchange chromatography media is BIA CIM® QA-80. One of ordinary skill in the art can appreciate that wash buffers of suitable ionic strength can be identified such that the rAAV remains bound to the resin while impurities, including without limitation impurities which may be introduced by upstream purification steps are stripped away.

In some embodiments, the anion exchange chromatography is performed as disclosed in U.S. Provisional Application No. 62/684,835, filed on Jun. 14, 2018, titled "ANION EXCHANGE CHROMATOGRAPHY FOR RECOMBINANT AAV PRODUCTION," which is incorporated herein by reference in its entirety.

In one embodiment, a method of isolating rAAV particles from the clarified harvest disclosed herein comprises a first tangential flow filtration, affinity chromatography, anion exchange chromatography, and a second tangential flow filtration. In one embodiment, the isolating the rAAV particles further comprises a sterile filtration.

In one embodiment, the method further comprises determining the genome titer (Vg), capsid titer (Cp), and/or percentage vector genome copies per capsid (Vg %) of a composition comprising the isolated recombinant rAAV particles comprising measuring the absorbance of the composition at 260 nm; and measuring the absorbance of the composition at 280 nm. In one embodiment, the method further comprises determining the genome titer (Vg), capsid titer (Cp), and/or percentage vector genome copies per capsid (Vg %) of a composition comprising the isolated recombinant rAAV particles comprising measuring the absorbance of the composition at 260 nm; and measuring the absorbance of the composition at 280 nm. In one embodiment, the absorbance is determined using a spectrophotometer. In one embodiment, the absorbance is determined using HPLC. In one embodiment, the absorbance is peak absorbance.

In one embodiment, the rAAV particles are not denatured prior to measuring the absorbance of the composition. In one embodiment, the rAAV particles are denatured prior to measuring the absorbance of the composition.

In additional embodiments the disclosure provides compositions comprising isolated recombinant rAAV particles produced by a method disclosed herein. In some embodiment, the composition is a pharmaceutical composition comprising a pharmaceutically acceptable carrier.

As used herein the term "pharmaceutically acceptable means a biologically acceptable formulation, gaseous, liquid or solid, or mixture thereof, which is suitable for one or more routes of administration, in vivo delivery or contact. A "pharmaceutically acceptable" composition is a material that is not biologically or otherwise undesirable, e.g., the material may be administered to a subject without causing substantial undesirable biological effects. Thus, such a pharmaceutical composition may be used, for example in administering rAAV isolated according to the disclosed methods to a subject. Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorbance promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions. Pharmaceutical compositions can be formulated to be compatible with a particular route of administration or delivery, as set forth herein or known to one of skill in the art. Thus, pharmaceutical compositions include carriers, diluents, or excipients suitable for administration by various routes. Pharmaceutical compositions and delivery systems appropriate for rAAV particles and methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

In some embodiments, the composition is a pharmaceutical unit dose. A "unit dose" refers to a physically discrete unit suited as a unitary dosage for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dose forms may be within, for example, ampules and vials, which may include a liquid composition, or a composition in a freeze-dried or lyophilized state; a sterile liquid carrier, for example, can be added prior to administration or delivery in vivo. Individual unit dose forms can be included in multi-dose kits or containers. Recombinant vector (e.g., AAV) sequences, plasmids, vector genomes, and recombinant virus particles, and pharmaceutical compositions thereof can be packaged in single or multiple unit dose form for ease of administration and uniformity of dosage. In some embodiments, the composition comprises rAAV particles comprising an AAV capsid protein from an AAV capsid serotype selected from AAV-1, AAV-2, AAV-3, AAV-4, AAV-5, AAV-6, AAV-7, AAV-8, AAV-9, AAV-10, AAV-11, AAV-12, AAV-13, AAV-14, AAV-15 and AAV-16. In some embodiments, the rAAV particles comprise an AAV capsid protein from an AAV capsid serotype selected from AAV-1, AAV-2, AAV-5, AAV-6, AAV-7, AAV-8, AAV-9, AAV-10, AAVrh.8, and AAVrh.10. In some embodiments, the AAV capsid serotype is AAV-8. In some embodiments, the AAV capsid serotype is AAV-9.

In some embodiments, a pharmaceutical composition produced according to the methods disclosed herein comprises between about 1×10E8 GC/ml and about 1×10E16 GC/ml.

In some embodiments, a unite dose of recombinant AAV particles produced according to the methods disclosed herein comprises between about 1×10E10 and about 1×10E16 GC.

Methods of Treating Diseases and Disorders

In some embodiments, the disclosure further provides methods for treating a disease or disorder in a subject in need thereof, comprising administering a therapeutically effective dose of isolated recombinant adeno-associated virus (rAAV) particles, wherein the amount of rAAV particles contained by the therapeutically effective dose has been determined using a method disclosed herein.

Isolated recombinant AAV particles or compositions comprising the isolated rAAV particles produced according to the methods disclosed herein can be used in delivering a transgene to a cell, e.g., cells of a human. For example, they can be used in medicine, e.g. to treat a disorder, for example, by delivering a therapeutic gene product to a cell or tissue. Thus, in some aspects of the invention, methods are disclosed herein for the expression of a gene in cells, the method comprising contacting cells with recombinant rAAV particles disclosed herein. In some embodiments, contacting occurs in vitro. In some embodiments, contacting occurs in vivo. In some embodiments, a composition comprising isolated rAAV particles disclosed herein is administered to a subject, e.g., a human subject. In some embodiments, the composition comprising isolated rAAV particles is administered parenterally, e.g., intravenously. In some embodiments, the composition comprising isolated rAAV particles is administered orally. In some embodiments, the composition comprising isolated rAAV particles is administered by intramuscular injection. In some embodiments, the composition comprising isolated rAAV particles is administered to the eye by injection, e.g., administered to the retina, subretina or vitreous. In some embodiments, the composition comprising isolated rAAV particles is administered by retinal injection, sub-retinal injection, or intravitreal injection.

The methods and compositions disclosed herein can be used in the treatment of any condition that can be addressed, at least in part, by gene therapy of cells. Thus, the compositions and methods of the present disclosure find use in the treatment of individuals in need of a cell therapy. Cells include but are not limited to blood, eye, liver, kidney, heart, muscle, stomach, intestine, pancreas, and skin.

In some embodiments, the subject has been diagnosed with or is suspected of having homozygous familial hypercholesterolemia (HoFH). HoFH is a monogenic disorder caused by abnormalities in the function or expression of the LDLR gene. HoFH patients have very low levels or are completely deficient of LDLR, resulting in very high total blood cholesterol levels. This leads to premature and aggressive plaque buildup, life threatening coronary artery disease (CAD) and aortic valve disease. In some embodiments, a method disclosed herein comprises administering to a subject that has been diagnosed with or is suspected of having homozygous familial hypercholesterolemia (HoFH) a therapeutically effective dose of rAAV particles comprising a polynucleotide sequence encoding a human low-density lipoprotein receptor (LDLR).

In some embodiments, the subject has been diagnosed with or is suspected of having Mucopolysaccharidosis type I (MPS I). MPS I is a rare recessive genetic disease caused by deficiency of IDUA, an enzyme required for the breakdown of polysaccharides heparan sulfate and dermatan sulfate in the lysosomes of cells. Many patients develop symptoms related to glycosaminoglycan storage in the CNS, which can include excessive accumulation of fluid in the brain (hydrocephalus), spinal cord compression and cognitive impairment. In some embodiments, a method disclosed herein comprises administering to a subject that has been diagnosed with or is suspected of having MPS I a therapeutically effective dose of rAAV particles comprising a polynucleotide sequence encoding a human α-1-iduronidase (IDUA).

In some embodiments, the subject has been diagnosed with or is suspected of having Mucopolysaccharidosis type II (MPS II). MPS II is a rare, X-linked recessive disease caused by a deficiency in the lysosomal enzyme IDS. In severe forms of the disease, early developmental milestones may be met, but developmental delay is readily apparent by 18 to 24 months. Developmental progression begins to plateau between three and five years of age, with regression reported to begin around six and a half years. In some embodiments, a method disclosed herein comprises administering to a subject that has been diagnosed with or is suspected of having MPS II a therapeutically effective dose of rAAV particles comprising a polynucleotide sequence encoding a human iduronate-2-sulfatase (IDS).

In some embodiments, the methods and compositions disclosed herein can be used for providing a gene product to a retina of a subject, comprising administering to the subject by intravitreal injection a disclosed pharmaceutical composition comprising rAAV particles.

In some embodiments, the subject has been diagnosed with or is suspected of having one or more diseases or disorders selected from the group consisting of: age-related macular degeneration (AMD), wet-AMD, dry-AMD, retinal neovascularization, choroidal neovascularization, diabetic retinopathy, proliferative diabetic retinopathy, retinal vein occlusion, central retinal vein occlusion, branched retinal vein occlusion, diabetic macular edema, diabetic retinal ischemia, ischemic retinopathy, and diabetic retinal edema.

In some embodiments, the subject has been diagnosed with or is suspected of having wet age-related macular degeneration (wet AMD). In some embodiments, a method disclosed herein comprises administering to a subject that has been diagnosed with or is suspected of having wet AMD a therapeutically effective dose of rAAV particles comprising a polynucleotide sequence encoding an anti-VEGF antibody or antigen binding fragment thereof.

Although the present disclosure has been described and illustrated in detail, this description is for illustrative purposes only and is not to be construed as limiting.

In order that the disclosure provided herein may be readily understood and put into practical effect, some embodiments will now be described by way of the following non-limiting examples.

EXAMPLES

Example 1. Calculating Genome Copy (GC) and Capsid Content from Absorbance

Gene therapy is a relatively new technique to cure diseases by inserting DNA into target cells. Adeno-Associated Viruses (AAV) are commonly used to deliver the target DNA used for gene therapy. AAV particles contain single-stranded DNA (~4000 base pairs) self-assembled within a protein capsid. Therefore AAV contains both DNA and protein component. Like in other therapeutic products, the quality, purity, and potency of AAV preparations must be monitored. Quality of AAV preparations, including the fully assembled AAV particle content, is particularly important so the dose can be determined. An added complication for AAV based therapeutic products is that AAV preparations comprise, in addition to fully assembled AAV particles, empty AAV capsids and AAV capsids with partial DNA content.

Most common techniques for measuring AAV content include Polymerase Chain Reaction (PCR) for measuring genome concentration, Analytical Ultracentrifugation (AUC) and Transmission Electron Microscopy (TEM) for measuring % Full Capsid concentration, and Enzyme-Linked ImmunoSorbent Assay (ELISA) for measuring Capsid concentration. All of these techniques are labor-intensive and time-consuming, and require complex instrumentation. Additionally, the PCR and ELISA assays do not distinguish fully assembled AAV particles from AAV capsids with partial DNA content or empty AAV capsids.

Spectrophotometry is the measurement of the absorbance of light at specific wavelengths. It is a common technique for measuring concentrations of therapeutic products with a single absorbance maximum for a single component. AAV content is more complicated to determine through spectrophotometry than many other therapeutic products because they contain two major species absorbing at different wavelength maxima (protein capsids at 280 nm, and DNA at 260 nm), and because capsid particles contain a mixture of empty and full capsids (FIG. 1). See, e.g., Sommer, Jurg M. (January 2003). Quantification of Adeno-Associated Virus Particles and Empty Capsids by Optical Density Measurement. Molecular Therapy, Vol. 7, pages 122-128.

In one aspect, provided herein are methods for determining AAV content directly by spectrophotometry without prior sample treatment. The methods can be used to determine both the level of genome copies and total capsids per sample, and to determine the ratio of empty and full capsids. Due to the low concentration of AAV products, matrix interference from buffer components can generate a large impact on the spectra profile and AAV content determination. For such samples, in some embodiments, the spectrophotometric method further includes filtration steps to capture the matrix components to subtract out the absorbance interference. The method was demonstrated to be precise and linear. Genome values calculated by spectrophotometry have good correlation to values determined by the PCR method. The estimated distribution of empty and full capsids calculated by spectrophotometry also correlate well with Analytical Ultracentrifugation (AUC) values. In summary, provided herein are spectrophotometry methods that are a faster and high-throughput alternative to the labor-intensive methods commonly used for AAV analysis for the determination of genome and capsid content.

Figure 12:
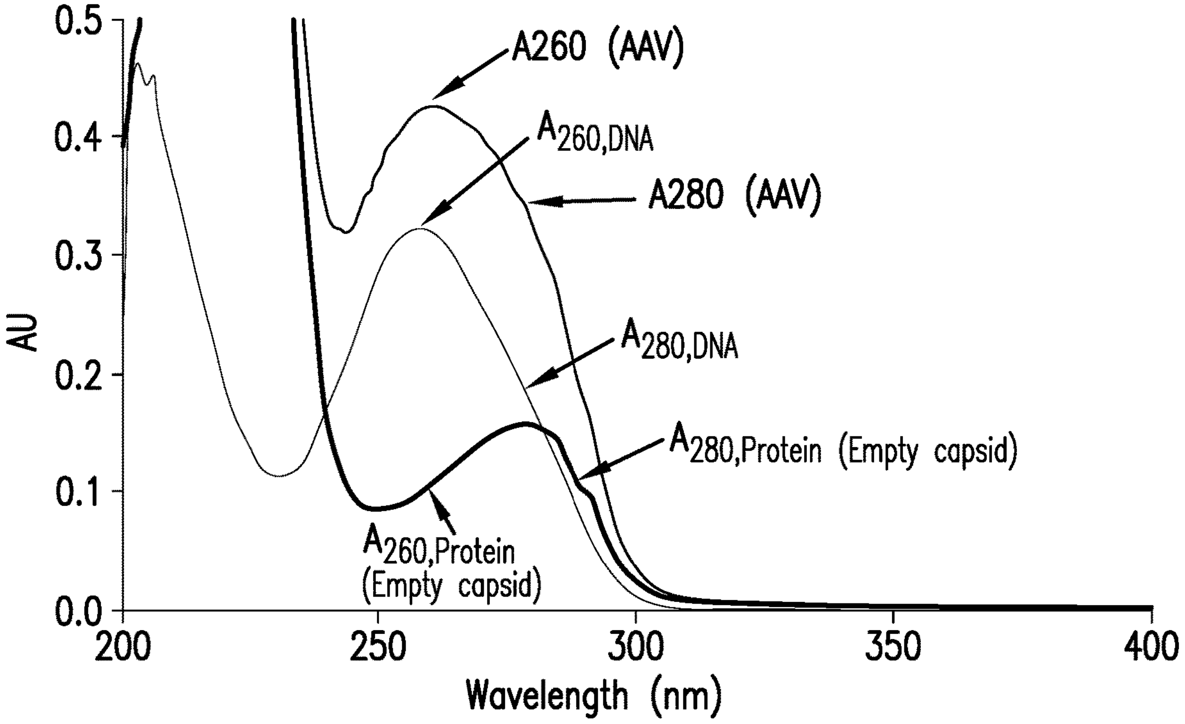
FIG. 12. illustrates a representative absorbance spectra and calculating genome copy (GC) and capsid content from absorbance.

Spectrophotometry was used to determine the concentration of AAV particles by applying Beer-Lambert's law. AAV particles comprise a protein capsid and single stranded DNA, both of which contribute to UV absorbance. FIG. 1. Before calculating genome copy number (GC/ml) and capsid content of the AAV composition from absorbance values, the capsid protein constants ($\beta$ and $\varepsilon_{Protein@280nm}$) and DNA constants ($\alpha$ and $\varepsilon_{DNA@260nm}$) were determined. FIG. 12A.

Empty capsid (containing no DNA) was used to determine the capsid protein constants ($\beta$ and $\varepsilon_{Protein@280nm}$). B equals the A260/A280 ratio of empty capsids. Edelhoch method was used to determine the extinction coefficient ($\varepsilon_{Protein@280nm}$). Edelhoch, H. 1967. Spectroscopic Determinations of Tryptophan and Tyrosine in Proteins. Biochemistry, Vol. 6, pages 1948-1954. Tryptophan, tyrosine, cysteine have known 8280 value denatured when in guanidine. The denatured extinction coefficient of the protein capsid was calculated ($\varepsilon_{Denatured}$) from the known Trp, Tyr, and Cys residue numbers per intact protein capsid. $\varepsilon_{Protein@280nm}$ was calculated based on the $\varepsilon_{Protein@280nm}=\varepsilon_{Denatured}$*(A280 of Native Capsid/A280 of Denatured Capsid) equation.

According to literature, $\alpha$=1.80 and $\varepsilon_{DNA@260nm}$=27000 (AU mL)/(cm g) for ssDNA. However, these constants vary depending on conformation of packed ssDNA within the capsid. AAV specific $\alpha$ and $\varepsilon_{DNA@260nm}$ can be determined by calibrating the % Full Capsid values obtained by spectrophotometry to an orthogonal method: % Full Capsids=(GC/ml)/(Capsid/ml).

Figure 13A:
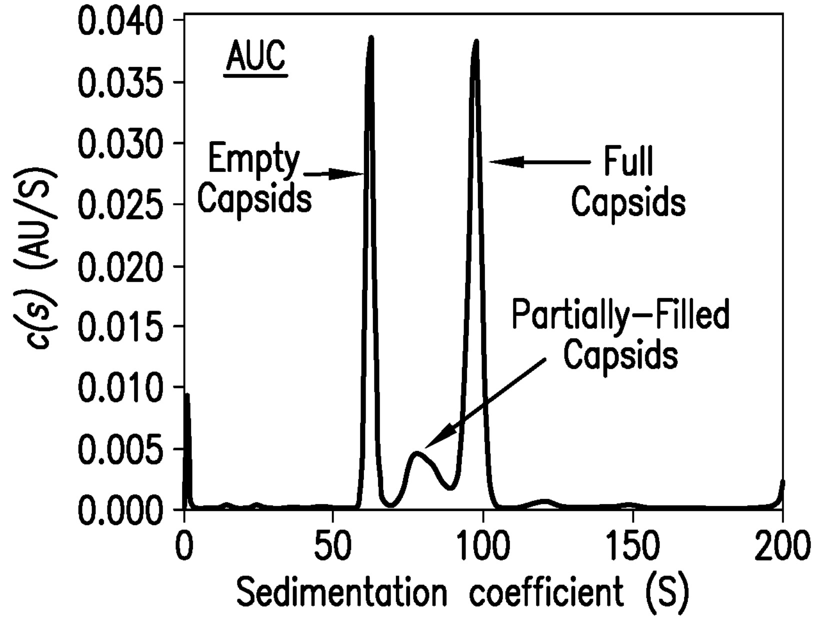
FIGS. 13A and 13B. Capsid content comparison by analytical ultracentrifugation (interference detection) (A) compared to the UV spectrophotometric method (B) (spiked-in rAAV at known values: 25%, 50% or 75 capsid).
Figure 13B:
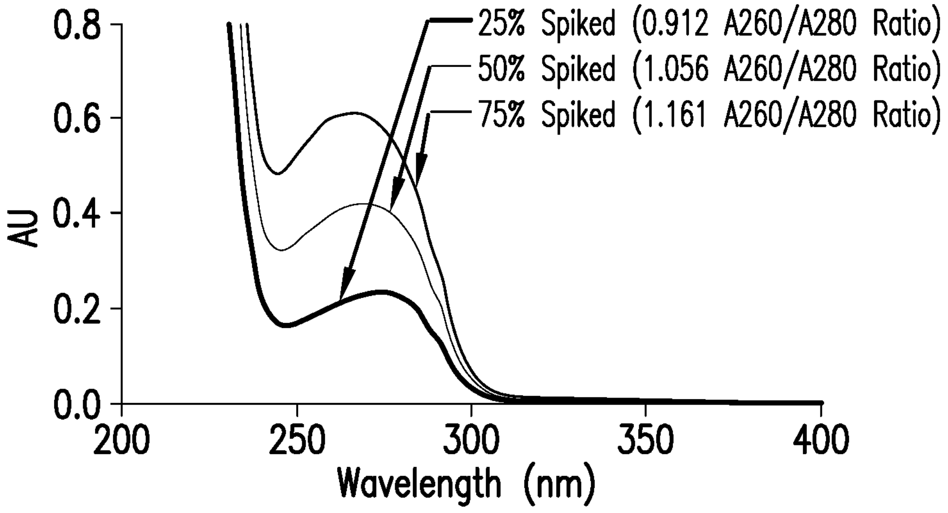
Figure 14:
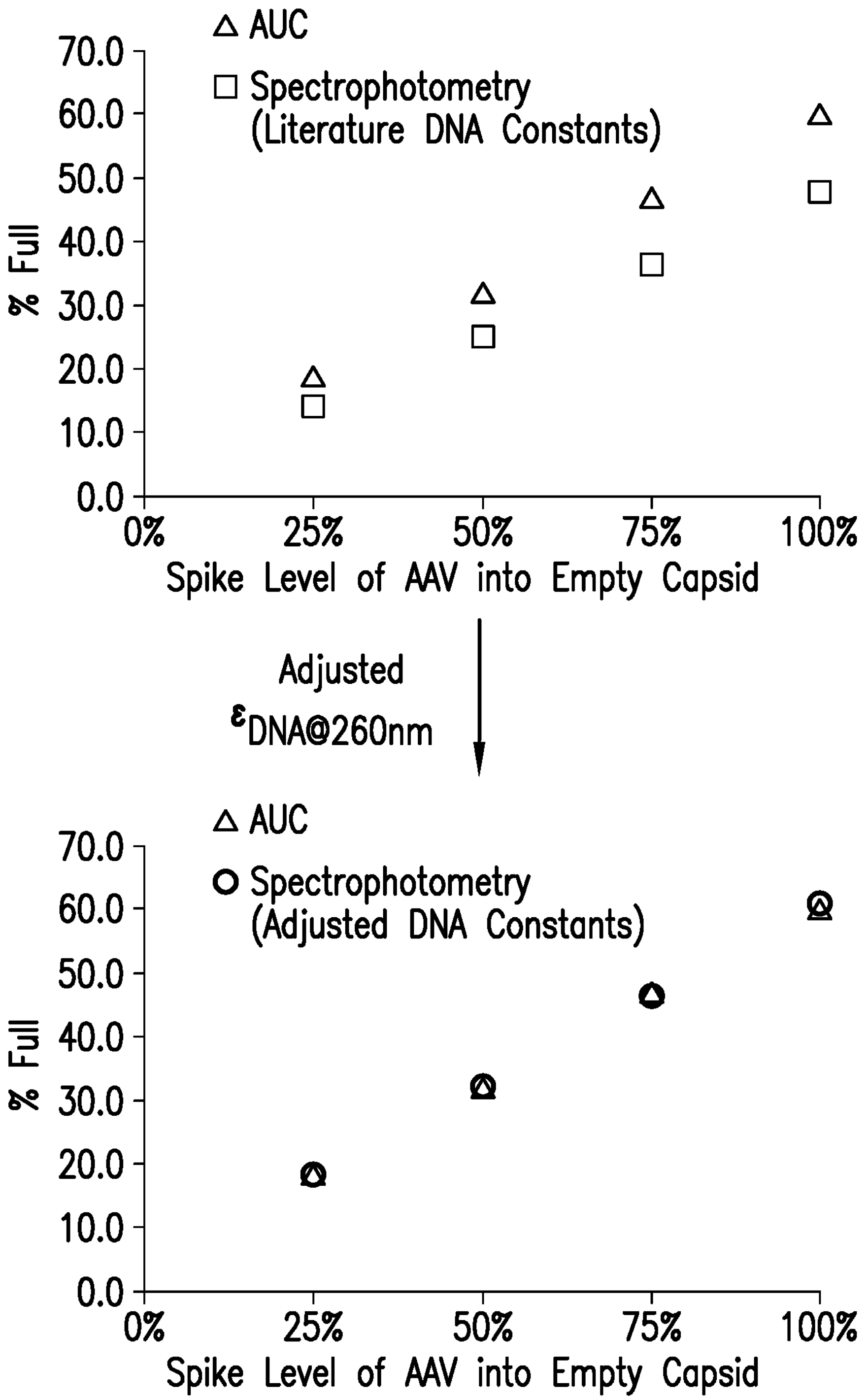
FIG. 14 Adjustment of DNA coefficients based on AUC data.

% Full Capsid Value Comparison by Analytical Ultracentrifugation (Interference Detection). Spiked samples comprising 25%, 50%, and 75% full capsids were prepared by mixing pure preparations of full and empty capsids. Samples were analyzed by AUC (interference detection, which has an equivalent signal for both empty and full capsids) and spectrophotometry. FIGS. 13A and 13B. $\varepsilon_{DNA@260nm}$ was adjusted to ensure that the % Full values obtained by the two methods match for each sample. % Full Capsid values calculated from the AUC data and from the absorbance values, before and after the adjustment to $\varepsilon_{DNA@260nm}$ are shown in FIG. 14.

Example 2. Analysis of Denatured vs Non-Denatured Samples

Large molecules can cause light scattering, which can cause inaccurate absorbance readings. A previous publication (Sommer, Jurg M. (January 2003). Quantification of Adeno-Associated Virus Particles and Empty Capsids by Optical Density Measurement. Molecular Therapy, Vol. 7, pages 122-128) reports that denatured AAV decreases light scattering caused by large molecules.

Figure 15:
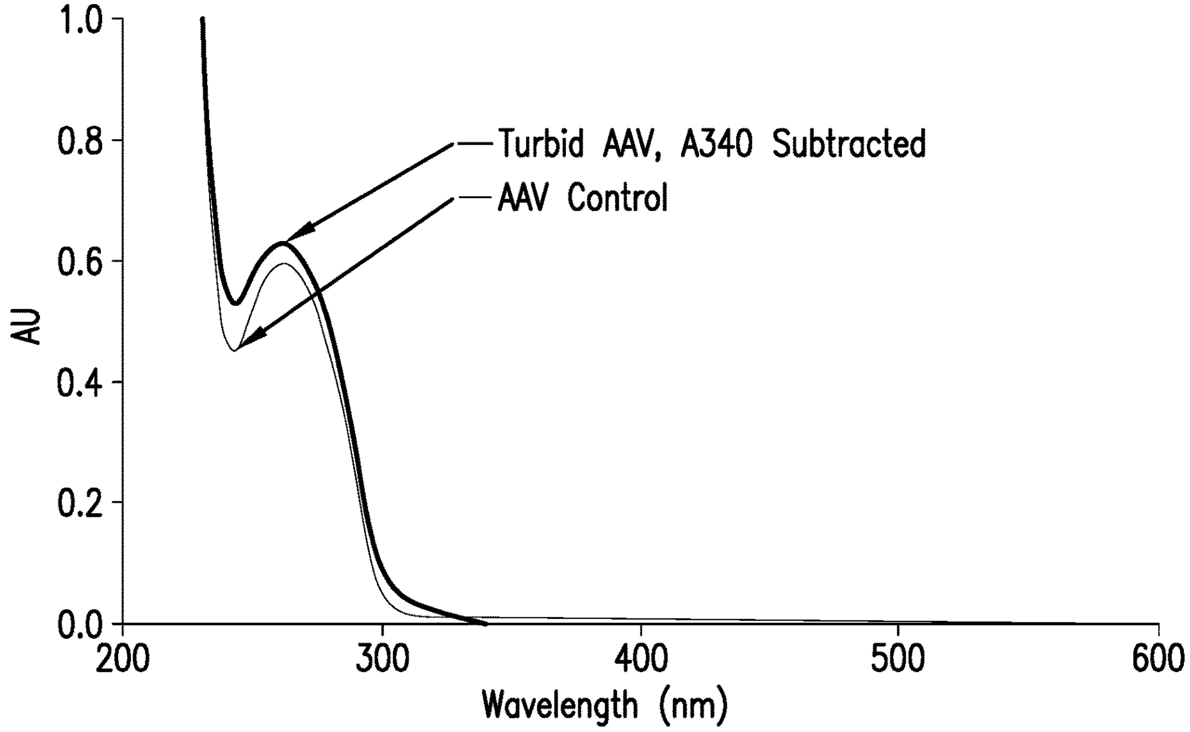
FIG. 15. Light scattering correction with A340 subtraction.

The same AAV sample was analyzed under denaturing conditions (heated at 75° C. for 10 minutes with 0.1% SDS)

and non-denaturing conditions (no prior sample treatment). FIG. 15 Denaturing AAV breaks the capsid into individual vector proteins and separates out the DNA. Single-stranded DNA anneals to form double-stranded DNA when the capsid is denatured. Double-stranded DNA typically has less absorbance than single-stranded DNA. The data demonstrates that denaturation is not necessary for AAV spectrophotometry analysis because only negligible levels of light scattering were detected under non-denaturing conditions as indicated by similar low absorbance above ~320 nm.

Analysis of AAV under non-denaturing conditions is advantageous because it has higher sensitivity due to higher & of single-stranded DNA, and because it requires no sample preparation making the analysis faster and less likely to be affected by analyst-error.

Example 4. Light Scattering Correction with A340 Subtraction

In situations when light scattering is a concern, a correction by subtracting A340 can also be used. Light scattering was forcibly induced in AAV sample compared to control. FIG. 15. Absorbance at A340 is the approximate difference in absorbance between Control and Turbid sample at A260 and A280. Subtracting A340 baseline from spectra provides similar profile to control.

In some embodiments, a method disclosed herein comprises subtracting A340 baseline from spectra.

Example 5. Comparison of Genome Content (GC/mL) by Spectrophotometry and Polymerase Chain Reaction (PCR)

Polymerase Chain Reaction (PCR) is the most common technique for determining genome content of AAV. Although GC/mL values obtained by PCR vary between different testing sites due to the design of primer/probe and other factors, there was a very good correlation per PCR testing site. FIG. 16 shows the correlation for 7 samples each of 2 different AAV products between spectrophotometry and PCR at a single amplification site.

In some embodiments, a method disclosed herein utilizes a correction factor to normalize the spectrophotometry value to the PCR value.

Example 6. Comparison of Spectrophotometry Values to Orthogonal Methods (% Full Values Compared Transmission Electron Microscopy)

Figure 17:
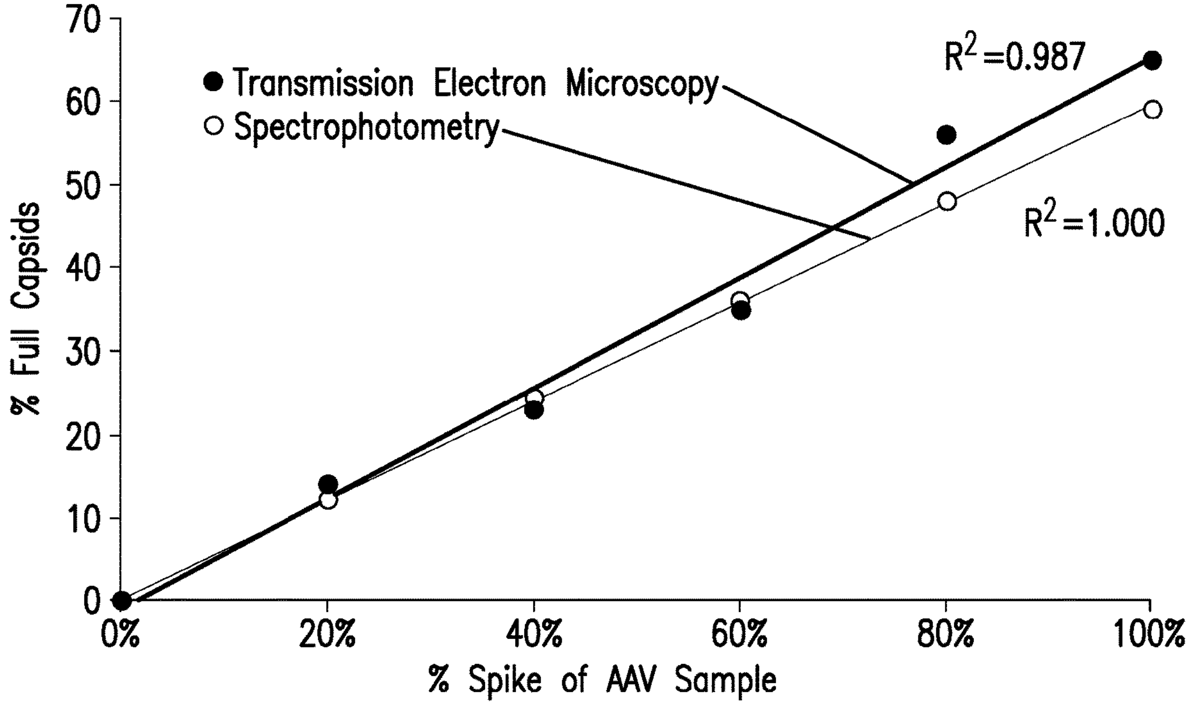
FIG. 17. Comparison of % Full Values between spectrophotometry and transmission electron microscopy.

An AAV sample with negligible level of partially-filled capsids was compared by Transmission Electron Microscopy (TEM) and spectrophotometry. Very similar results were obtained indicating the accuracy of the spectrophotometry values. FIG. 17. Indeed, spectrophotometry had a better linear correlation than TEM.

Example 7. Comparison of Spectrophotometry Values to Orthogonal Methods Full Values Compared to AUC, 280 nm Detection)

Figure 18A:
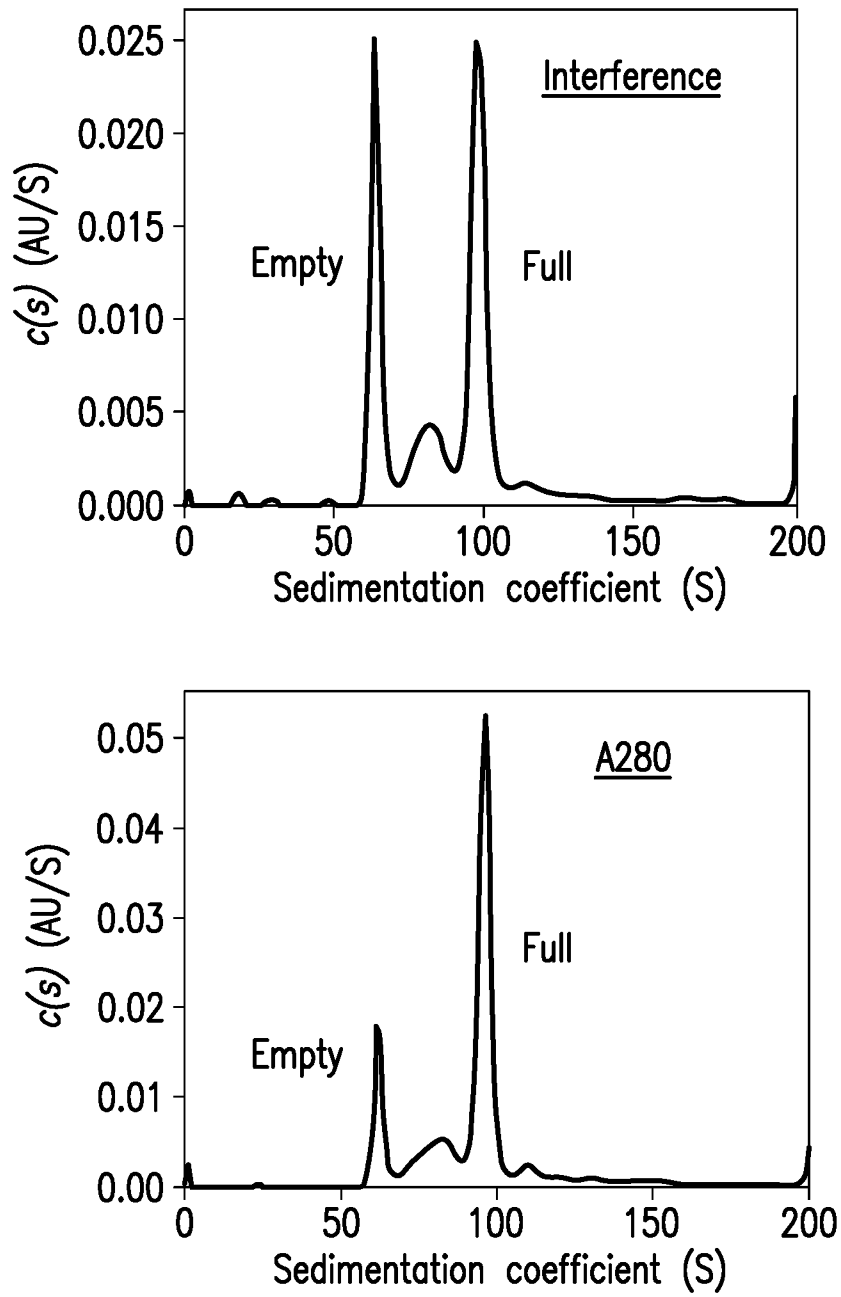
FIGS. 18A-C.
Figures 18B, 18C:
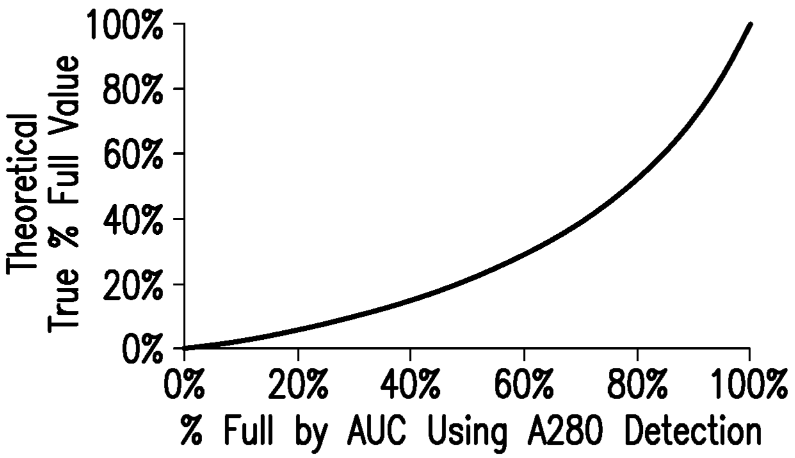

Analytical Ultracentrifugation (AUC) is the most common technique for determining the ratio of full to empty AAV capsids. It is current industry practice to analyze AUC using A280 detection. When AUC detects using 280 nm, the level of full capsids are inherently over-estimated relative to the empty capsids because both DNA and protein contribute to the full capsid signal at 280 nm. FIGS. 18A-C show the full to empty AAV ratios measured by AUC using interference or A280 absorbance to detect AAV particles. For AAV samples with negligible partially-full capsids, the difference between the True % Full Value and the % Full Value estimated by AUC using A280 detection is small. However, for AAV sample with significant levels of partially-full capsids, a normalization is used to determine true % full value (FIG. 18B). The Table in FIG. 18C shows the correlation between % Full values determined by a method disclosed herein (Spectrophotometry % Full) and Adjusted AUC % Full value.

Example 8. Spectra Interference

Some in-process samples had residual buffers, i.e., matrix that may interfere with absorbance at 260 or 280 nm. FIGS. 4 and 19. These components could not be traditionally blanked due to the variable levels of matrix components between samples. Matrix spectra was obtained by filtering the sample, allowing the buffer to permeate through but retaining the AAV. The spectra of the AAV was then determined by subtracting the matrix spectra.

Example 9. Qualification Results

Figure 20B:
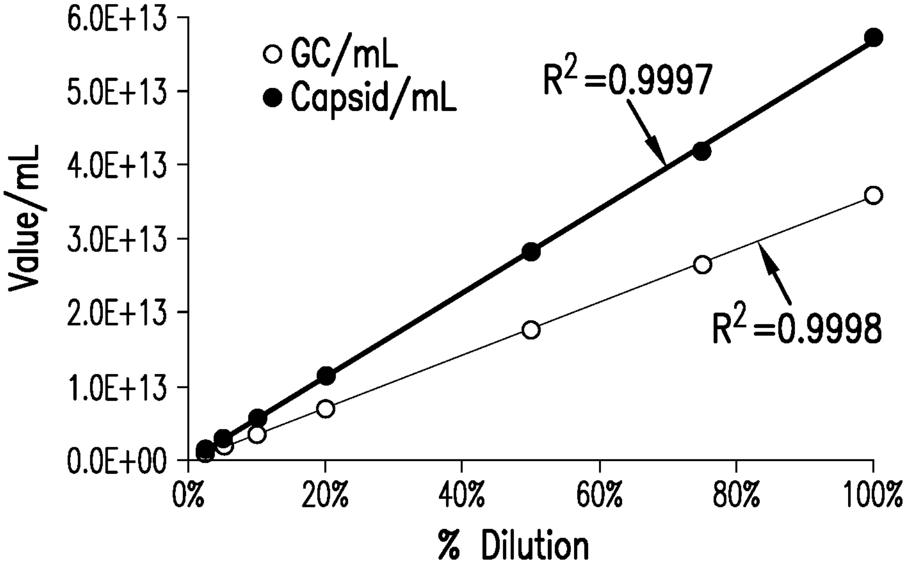
Figure 20C:
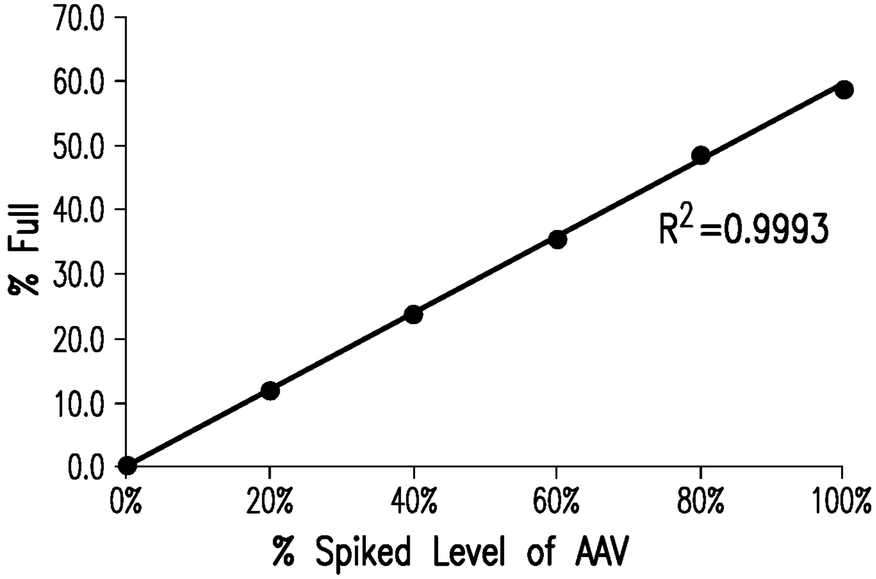

FIGS. 20A-C show qualification results obtained for an AAV preparation using the methods disclosed herein. The results indicate that the method was linear and precise.

The methods described herein provide fast, easy, high-throughput methods with real-time capability that can be used in Short Turn Around Time testing. The methods require little to no sample preparation, other than dilution of highly concentrated AAV samples. And the methods provide reproducible results within the same lab and between different sites, provide equivalent results with different lab/instrumentation, are easy to transfer, and are quality control-friendly. Data obtained with the methods is comparable to results obtained by orthogonal methods (PCR, AUC, TEM).

Example 10. Determination of AAV Genome Content and Capsid Content by Size Exclusion Chromatography Genome content of adeno-associated virus preparations can be determined by measuring Optical Density (OD) and by Polymerase Chain Reaction (PCR). However, PCR assays are time consuming and have high assay-to-assay and lab-to-lab variability. While Optical Density is capable of quantitating capsid and genome copy titers with a higher sample throughput, it also has limitations. For example, light scattering may induce error in absorbance readings, low concentrations are difficult to measure, and some sample matrices may interfere at 260 nm and 280 nm wavelengths.

In some embodiments, analytical methods disclosed herein comprise the use of size exclusion chromatography (SEC) to separate analytes by size, which gives these methods advantages over OD and over methods using other modes of chromatography. The SEC technique allows for complete separation of AAV capsids from excipients and other buffer related components due to their large size difference. Chromatograms by SEC have a flat and stable baseline. And SEC based titer is specific to AAV due to the specific elution time of AAV.

Genome content quantitation was accomplished with two different methods; both of which showed high correlation to spectrometry method. The absolute quantitation SEC-titer method used the peak areas collected at 280 nm and 260 nm UV absorbances, and directly calculated capsid and genome copy titer for AAV products. The SEC-214 method utilized an empty capsid calibration curve to calculate capsid titers.

Method Overview: Unless otherwise defined, the SEC-based methods disclosed in this Example used an Agilent Infinity II 1260 HPLC instrument and Sepax 500 Å SEC column with a flowrate of 0.2-0.35 mL/min. The mobile phase was a phosphate buffer system. The quantitation range was >1E+10 Capsids/mL.

Figure 21:
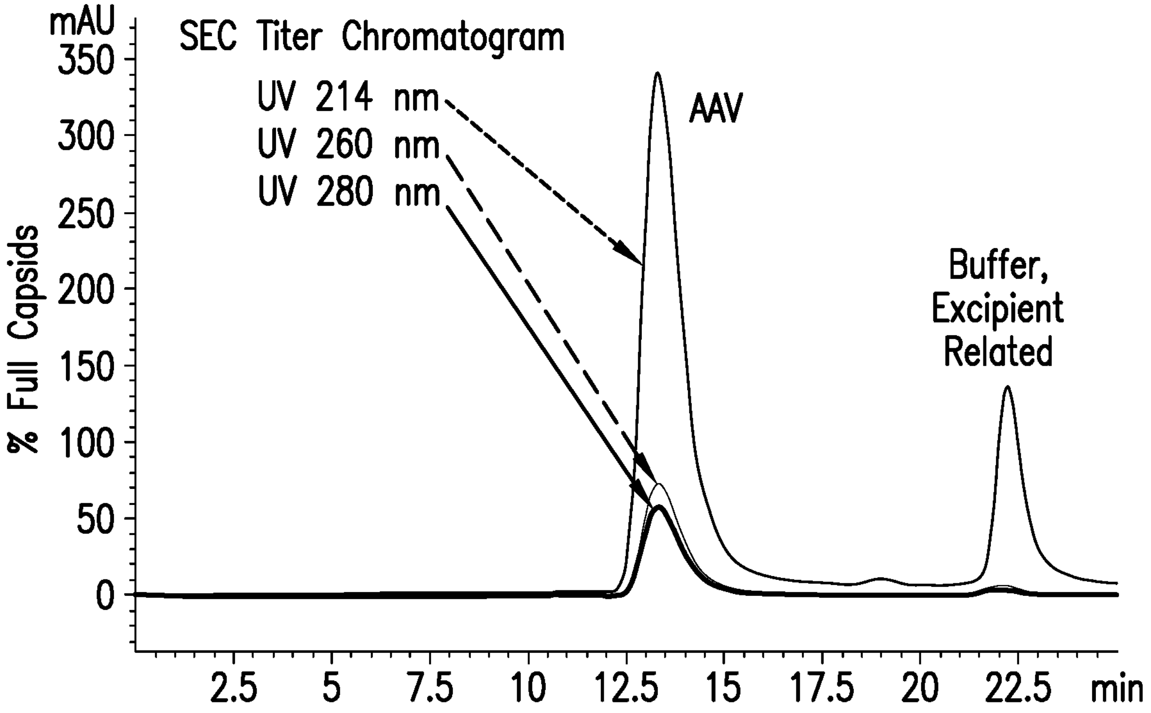
FIG. 21. SEC Titer Chromatogram. UV detection at multiple ultraviolet wavelengths (214 nm, 280 nm and 260 nm) are used in order to understand both DNA's and protein's contribution to total absorbance.
Figure 22:
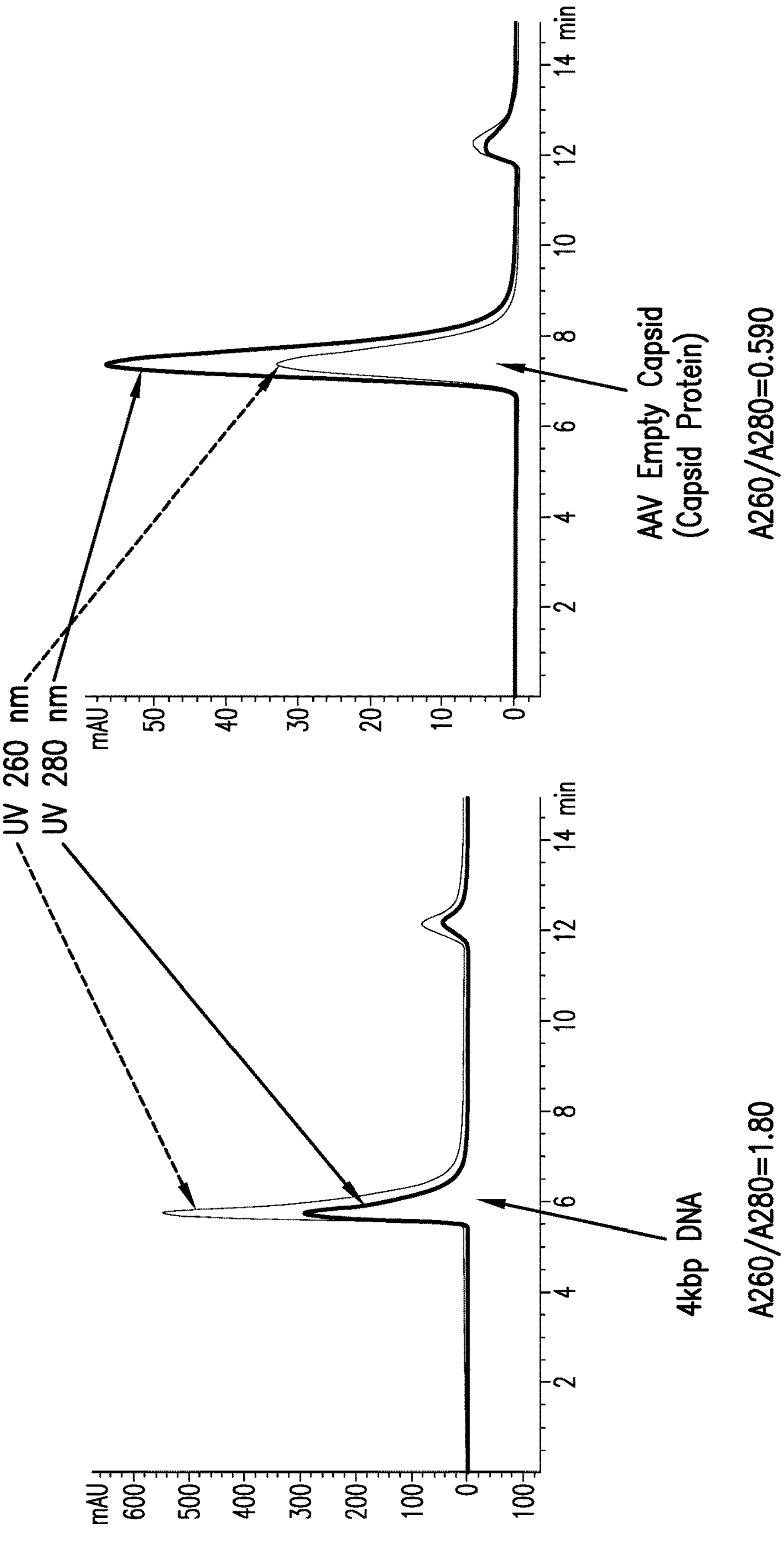
FIG. 22. SEC Titer Chromatogram. The SEC method was performed on pure 4 kb DNA and purified AAV empty capsids. The peak area ratio at 260 nm and 280 nm were then determined.

AAV contains two components: DNA and Protein. Both contribute to total UV absorbance at different levels depending on the empty/full ratio of the particular AAV sample. UV detection at multiple ultraviolet wavelengths (214 nm, 280 nm and 260 nm) was used in order to understand both DNA's and protein's contribution to total absorbance. FIG. 21. The SEC method was performed on pure 4 kb DNA and purified AAV empty capsids and the peak area ratio at 260 nm and 280 nm was than determined for each. FIG. 22. The peak area $A_{260}/A_{280}$ ratio for pure 4 kb DNA was 1.80. The peak area $A_{260}/A_{280}$ ratio for AAV Empty Capsid (Capsid Protein) was 0.590.

Determination of Capsid Titer by SEC-214 Method: The quantitation utilized a calibration curve of AAV capsids that contain capsids lacking the genome (empty capsids). The concentration of empty capsid standards was determined using traditional Beer-Lambert law, which in general is considered to be an accurate method within 10% error to the true values. UV acquisition at the wavelength of 214 nm was employed.

Relative UV absorption by DNA was significantly reduced at 214 nm (>⅙th absorption at 214 nm for AAV). The small portion of UV absorbance contributed by genome DNA was corrected by estimating through $A_{260}/A_{280}$. A linear trendline was used in the following equations to assess the capsid titers.

$$\text{Capsid titer}=m(\text{Total Sample Absorbance @214 nm}-(\text{Total DNA Absorbance @ 214 nm}))-b$$

or $$\text{Capsid titer}=m(A_{214\ AAV}-K(A_{260\ AAV}-0.590A_{280\ AAV}))-b$$

m=Slope of empty capsid linear regression

A214, A260, A280=Peak area at UV 214, 260 and 280 nm wavelengths

Figure 23:
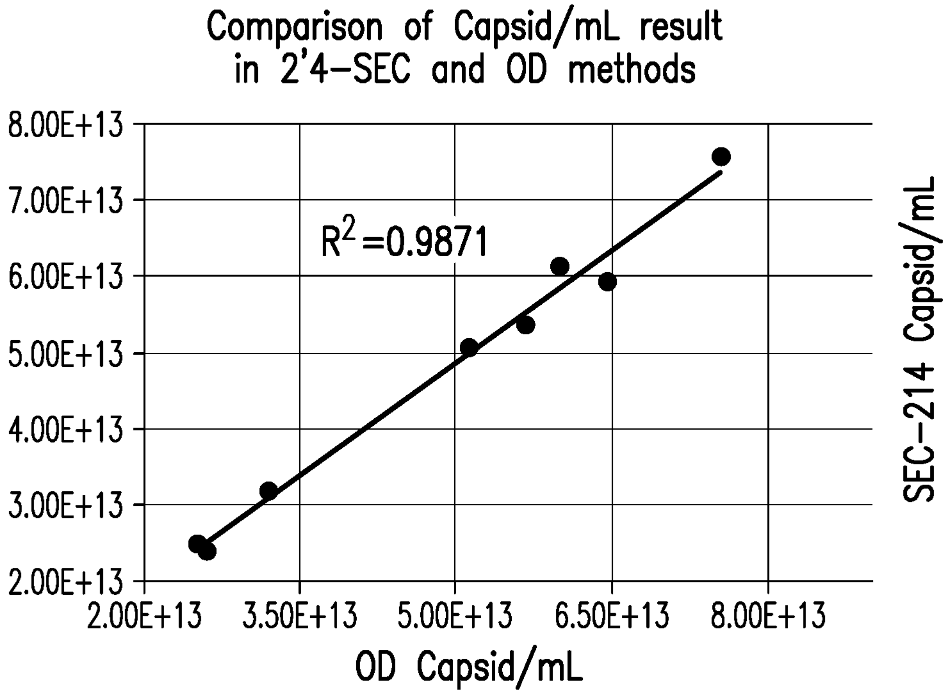
FIG. 23. Capsid titer results determined by SEC-214 and OD methods are highly comparable.

K—A factor related to A214/A260 ratio of DNA b=y-intercept of empty calibration curve Capsid titer results determined by SEC-214 and OD methods are highly comparable. FIG. 23. Overall, the relative difference between these methods was <5% (R2-0.9871), assessed over a wide capsid concentration range (2×E+13 to 8×E+13). Determination of Genome Content and Capsid Content by Absolute Quantitation Method: Genome Content was calculated directly, without a calibration curve using the collected peak areas acquired at 260 nm and 280 nm. AAV extinction coefficients were experimentally derived using Pace et al method. Pace, C. N. et al., "How to Measure and Predict the Molar Absorption Coefficient of a Protein," Protein Sci. 4, 2411-2423 (1995). Flowrate, injection volume and detector path length were accounted in the calculation.

$$\text{Genome content }(GC/\text{mL})=\text{Flowrate }K_{DNA}(A260-0.590A280)/(VL)$$

$$\text{Capsid content (capsid/mL)}=\text{Flowrate }K_{capsid}(A280-A260/1.80)/(VL)$$

Figure 24A:
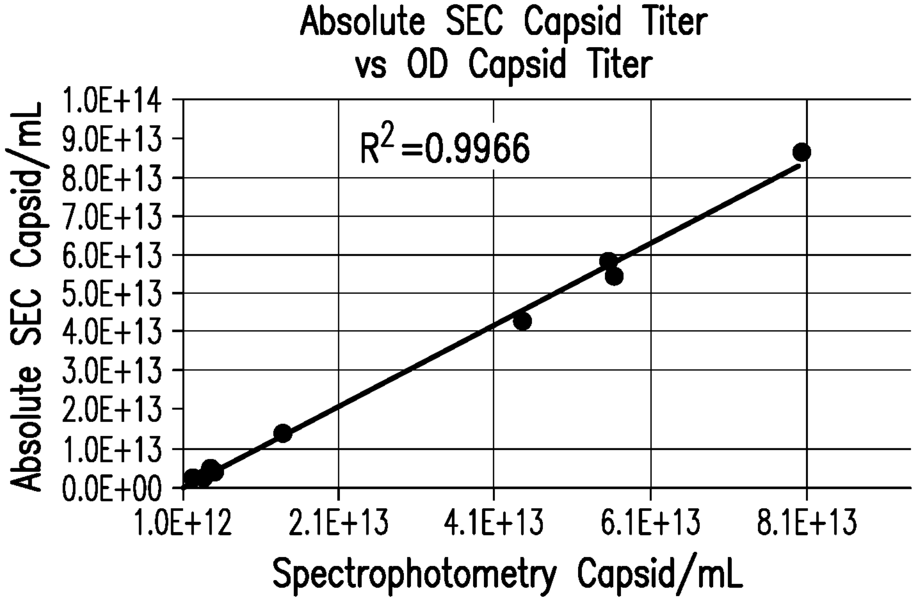
FIGS. 24A-C. Comparison of Absolute SEC Quantitation to ddPCR and Spectrophotometry FIG. 25. Linearity Assessment.
Figure 24B:
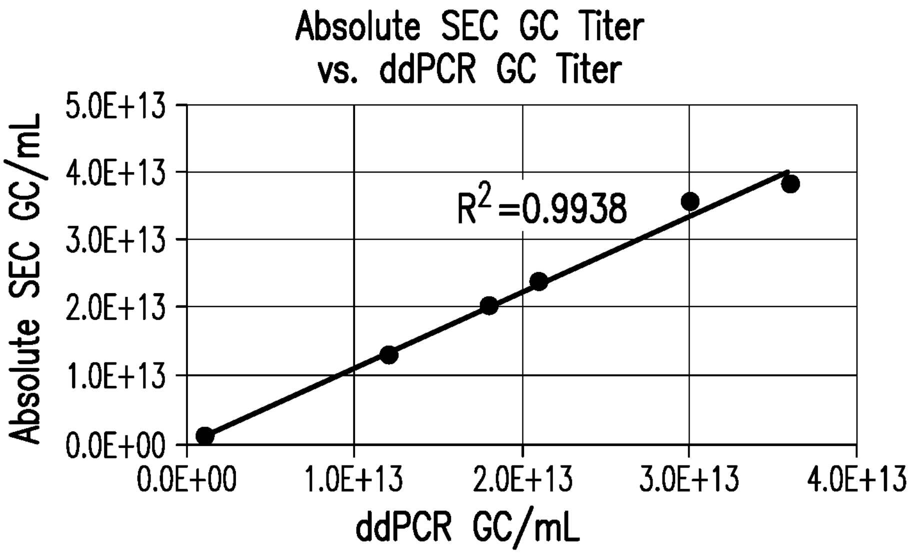
Figure 24C:
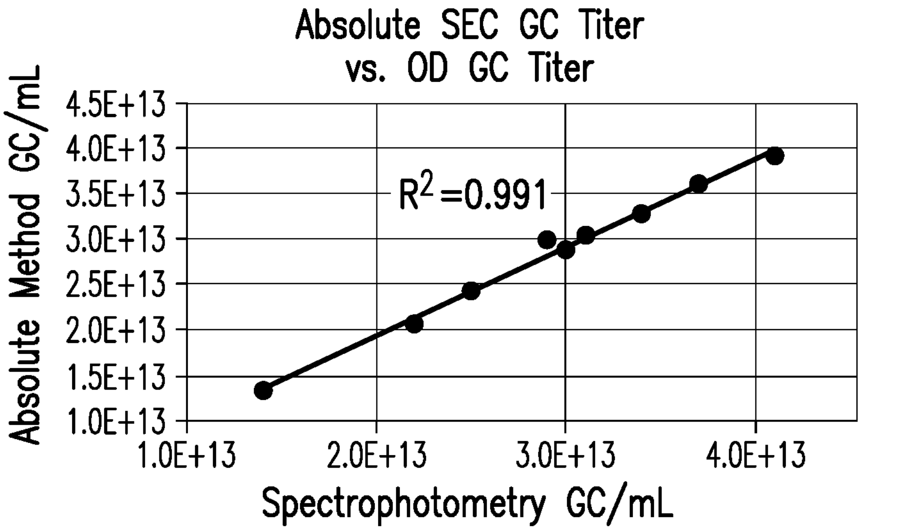

$K_{DNA}$=Experimentally derived extinction coefficient factor for genome DNA $K_{capsid}$=Experimentally derived extinction coefficient factor for capsid protein A280=peak area at 280 nm wavelength A260=peak area at 260 nm wavelength V=injection volume L=UV detector path length The results demonstrated good agreement between absolute SEC quantification and OD method. FIG. 24A and FIG. 24C. Overall, variability was <10% between OD and SEC titer. The results also showed good correlation between absolute SEC quantification and ddPCR. FIG. 24B.

Figure 25:
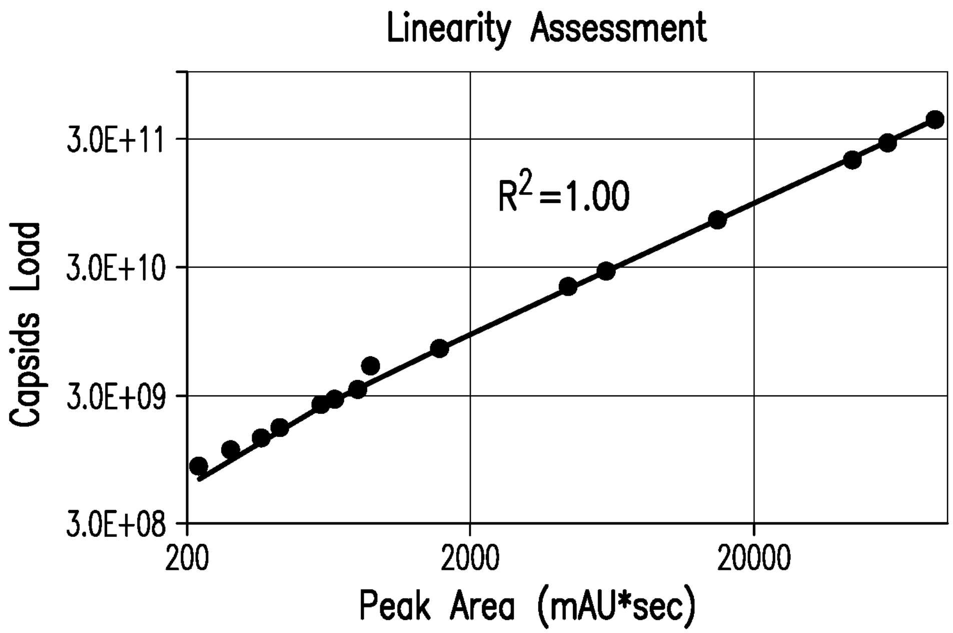

Method Performance: AAV products generally have a low concentrations, with some product dosed at <1 μg/mL. Decreasing flowrates increased sensitivity due to the analyte spending more time passing through the detector. The absolute quantitation method was able to quantitate samples with $>1.0\times10^{10}$ capsids/mL (~0.06 μg/mL of protein). FIG. 25.

Accuracy assessment

| Sample | Theoretical Capsid/mL | SEC-214 Capsid/mL | Absolute Capsid/mL | % Difference SEC-214 | % Difference Absolute SEC |
|---|---|---|---|---|---|
| Sample #1 | 2.31E+12 | 2.25E+12 | 2.33E+12 | 2.7% | −0.9% |
| Sample #2 | 3.93E+12 | 3.79E+12 | 3.91E+12 | 3.6% | 0.6% |
| Sample #3 | 5.36E+12 | 5.20E+12 | 5.17E+12 | 3.0% | 3.6% |
| Sample #4 | 1.43E+12 | 1.44E+12 | 1.46E+12 | −1.0% | −2.4% |
| Sample #5 | 3.11E+12 | 3.06E+12 | 3.05E+12 | 1.6% | 2.0% |
| Sample #6 | 4.59E+12 | 4.45E+12 | 4.50E+12 | 3.1% | 1.9% |

Both SEC-214 and absolute SEC quantitation methods were very accurate, with <4% difference between capsid titers determined by both methods and theoretical capsid titers.

Figure 26:
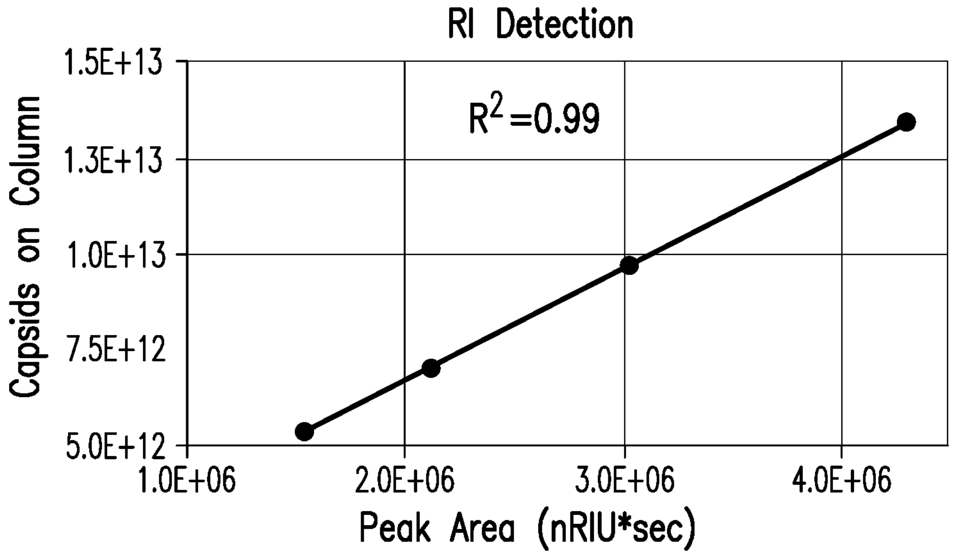
FIG. 26. Capsid Titer results showed <9% difference between RI and absolute quantification.

Confirmation of Capsid Titer Through Orthogonal Methods: Refractive Index (RI) detection was used to further verify the capsid content of AAV samples. Refractive Index detector measures changes in the way light is bent in samples compared to buffer the sample is in. RI detects capsids only regardless the DNA content inside capsids. A calibration curve of empty capsids was prepared and a linear trendline was applied. The linear equation was then used to assess Capsid Titer by RI detection. Capsid Titer results were <9% difference between RI and absolute quantitation. FIG. 26.

Figure 27:
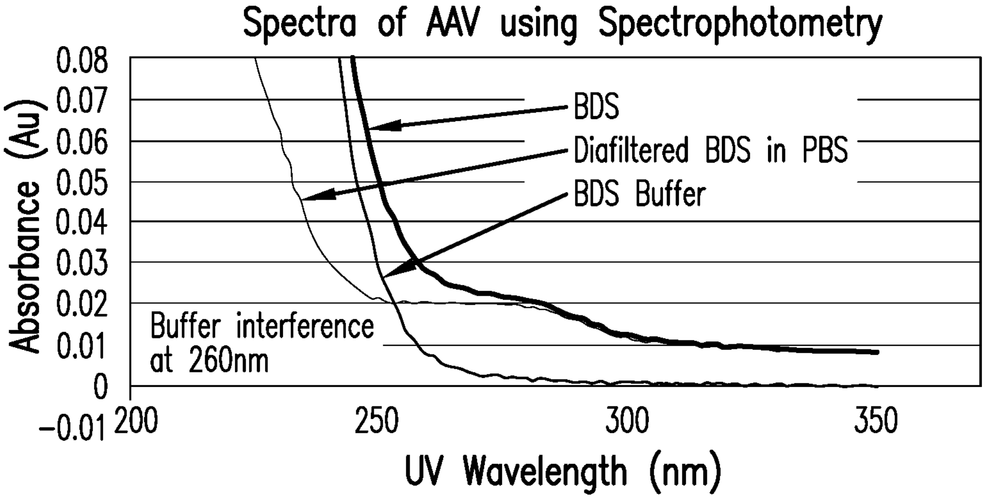
FIG. 27. Spectra of AAV using Spectrophotometry. Spectra of Bulk Drug Substance (BDS), diafiltered BDS in phosphate buffered saline (PBS), and BDS buffer is shown.
Figure 28:
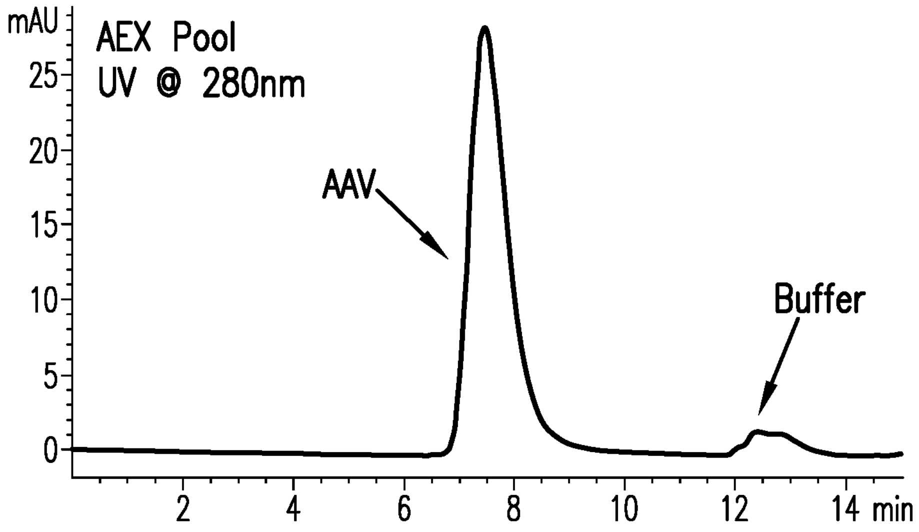
FIG. 28. SEC-HPLC separates analytes on the basis of size. This allows AAV to be completely separated from potential impurities and buffer interference in absorbance.

Determination of Genome and Capsid Content in Downstream In-Process Samples: Spectrophotometry analysis is not specific to AAV due to the nature of analysis. This becomes more apparent in less pure samples where additional components such as process impurities and buffers contribute to absorbance. FIG. 27. SEC-HPLC separates analytes on the basis of size. This allows AAV to be completely separated from potential impurities and buffer interference in absorbance. FIG. 28.

| | SEC -214 | Optical Density | % RPD between OD and SEC | |
|---|---|---|---|---|
| Sample | A260/A280 | A260/A280 | Capsid/mL | GC/mL |
| Purification Step 1 | 1.024 | 1.038 | 10.5 | 15.7 |
| Purification Step 2 | 1.205 | 1.272 | 10.9 | 11.9 |
| Purification Step 3 | 1.196 | 1.232 | 9.4 | 2.5 |
| Bulk Drug | 1.208 | 1.234 | 5.0 | 3.9 |

-continued

| Sample | SEC -214 A260/A280 | Optical Density A260/A280 | % RPD between OD and SEC Capsid/mL | GC/mL |
|---|---|---|---|---|
| Substance | | | | |

A260/A280 ratio should be consistent after purification Step 2 because the empty/full capsid ratio does not change after this step. The results above show spectrophotometry was only capable of assessing pure AAV samples due to the $A_{260}/A_{280}$ variability.

Figure 29:
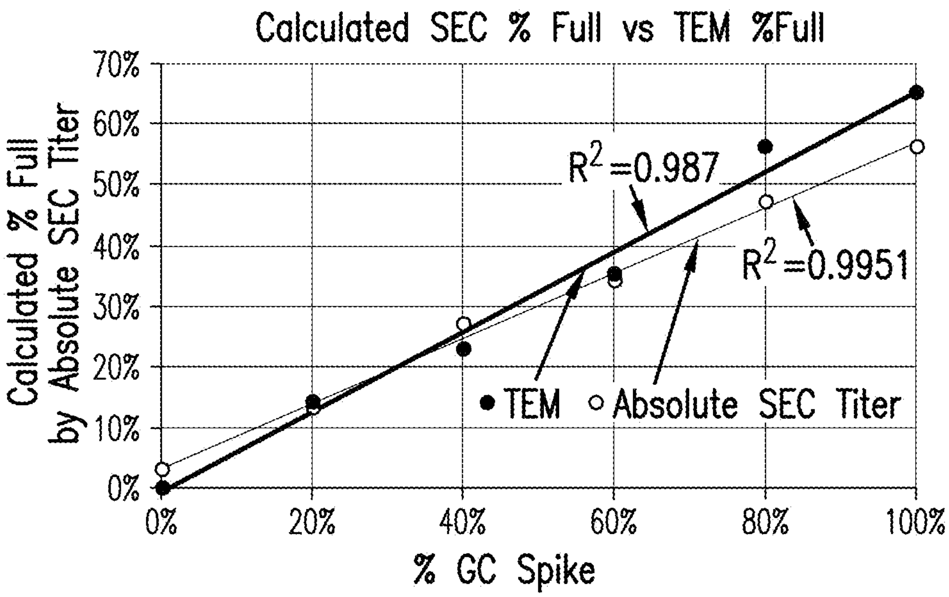
FIG. 29. % Full assessed by SEC Titer strongly correlates with Transmission Electron Microscopy results.
Figure 30:
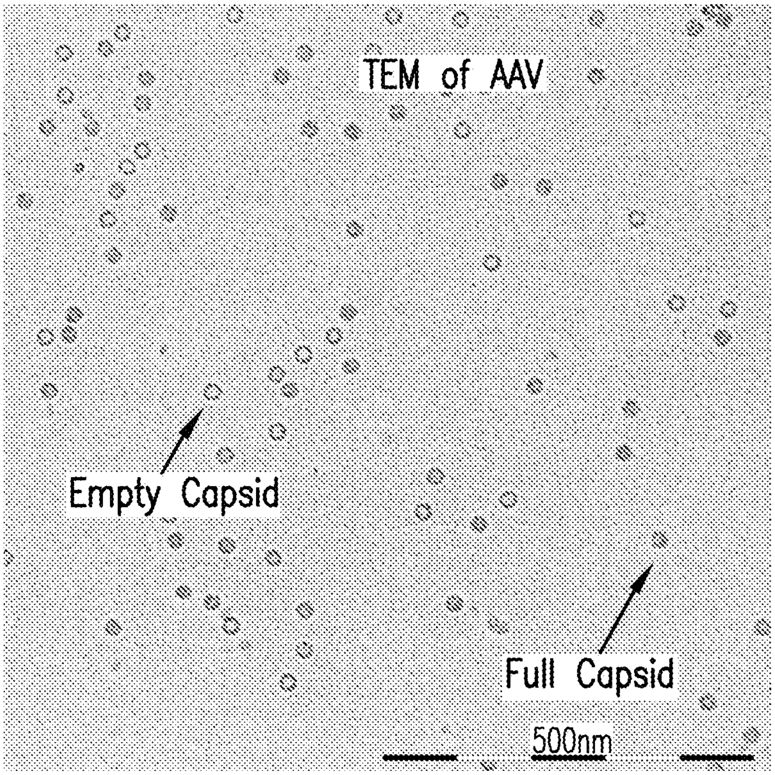
FIG. 30. Transmission Electron Microscopy results.

% Full Comparison between Absolute Quantitation SEC and Transmission Electron Microscope: The absolute SEC quantitation method was used to assess the percent capsids containing the genome (% Full). % Full assessed by SEC Titer strongly correlated with Transmission Electron Microscopy results. FIGS. 29 and 30. Determination of Bovine Serum Albumin Concentration via Absolute Quantitation Method: The concentration of Bovine Serum Albumin (BSA) was assessed by the absolute quantitation method using the peak area at 280 nm solely as system suitability testing for AAV analysis.

$$\text{BSA content (mg/mL)}=\text{Flowrate}\times K_{BSA}\times A280/(V\times L)$$

$K_{BSA}$=Experimentally derived extinction coefficient factor for BSA

A280=peak area at 280 nm wavelength (mAU×sec)

A260=peak area at 260 nm wavelength

V=injection volume

L=UV detector path length

Results show that absolute quantitation can be applied to therapeutic proteins, including mAbs. Similar absolute quantification can also be used for other HPLC modes, such as ion-exchange and affinity chromatography. BSA was used as a part of system suitability. Highly precise and accurate BSA data were demonstrated by the absolute quantification method.

| Replicate | Concentration mg/mL |
|---|---|
| 1 | 2.03 |
| 2 | 2.03 |
| 3 | 1.96 |
| 4 | 1.97 |
| 5 | 1.96 |
| 6 | 2.03 |
| 7 | 2.06 |
| 8 | 2.07 |
| 9 | 2.08 |
| % RSD | 2.22 |

The SEC Titer method disclosed herein was capable of quantitating capsid and genome copy titer using the absorbance at 214 nm, 280 nm and 260 nm. Both quantitation methods showed high accuracy, high precision and had a wide linear range capable of quantitating samples with $>1.0\times10^{10}$ Capsids/mL. Both SEC-214 and absolute quantitation methods disclosed herein showed high comparably to ddPCR and OD results with a relative difference <10%. The SEC Titer method disclosed herein was capable of analyzing samples with high buffer UV interference, high light scattering and low concentrations.

While the disclosed methods have been described in connection with what is presently considered to be the most practical and preferred embodiments, it is to be understood that the methods encompassed by the disclosure are not to be limited to the disclosed embodiments, but on the contrary, is intended to cover various modifications and equivalent arrangements included within the spirit and scope of the appended claims.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

What we claim is:

1. A method of producing a pharmaceutical composition comprising isolated recombinant adeno-associated virus (rAAV) particles, comprising (1) isolating rAAV particles under non-denaturing conditions from a feed comprising an impurity by one or more of centrifugation, depth filtration, tangential flow filtration, ultrafiltration, affinity chromatography, size exclusion chromatography, ion exchange chromatography, and hydrophobic interaction chromatography, (2) determining percentage vector genome copies per capsid (Vg %) of the isolated rAAV particles, (3) using the Vg % to determine the quality of the isolated rAAV particles, and (4) producing the pharmaceutical composition comprising the isolated rAAV particles and a pharmaceutically acceptable carrier when the Vg % meets a predetermined quality requirement, wherein the Vg % is determined by a) determining the absorbance of a composition comprising the rAAV particles at least at 260 nm and at 280 nm under non-denaturing conditions, and b) calculating the Vg %, wherein the calculating comprises using the following equations $$Vg(GC/\text{mL}) = \frac{(A_{260} - \alpha A_{280})}{\varepsilon_{DNA260}\,(1-\alpha/\beta)L},$$

$$Cp(\text{capsid/mL}) = \frac{(A_{280} - A_{260}/\beta)}{\varepsilon_{protein280}\,(1-\alpha/\beta)L},$$

and $$Vg\ \% = Vg/Cp$$

wherein A=Absorbance; ε=Extinction Coefficient (Molar absorptivity); C=Sample Concentration; L=Path length, $\alpha=\varepsilon_{protein260}/\varepsilon_{protein280}$, $\beta=\varepsilon_{DNA260}/\varepsilon_{DNA280}$, wherein the extinction coefficients are specific for the genome and for the capsid of the isolated rAAV particles under non-denaturing conditions.

2. The method of claim 1, wherein the method comprises determining the absorbance of the composition comprising the rAAV particles at least at 260 nm and at 280 nm using slope spectroscopy.

3. The method of claim 1, wherein the method comprises analyzing the composition on an HPLC system with UV detection to determine the peak absorbance corresponding to the rAAV particles at least at 260 nm and at 280 nm.

4. A method of producing a pharmaceutical composition comprising isolated recombinant adeno-associated virus (rAAV) particles, comprising (1) obtaining a feed sample comprising rAAV particles, (2) determining percentage vector genome copies per capsid (Vg %) of the rAAV particles, and (3) using the Vg % to determine the quality of the rAAV particles, and (4) isolating rAAV particles under non-denaturing conditions from the feed sample when they meet a predetermined quality requirement or removing the feed sample when they do not meet the quality requirement, wherein the Vg % is determined by a) determining the absorbance of a composition comprising the rAAV particles at least at 260 nm and at 280 nm, under non-denaturing conditions, and b) calculating the Vg %, wherein the calculating comprises using the following equations $$Vg(GC/\text{mL}) = \frac{(A_{260} - \alpha A_{280})}{\varepsilon_{DNA260}\,(1 - \alpha/\beta)L},$$

$$Cp(\text{capsid/mL}) = \frac{(A_{280} - A_{260}/\beta)}{\varepsilon_{protein280}\,(1 - \alpha/\beta)L},$$

and $$Vg\ \% = Vg/Cp$$

wherein A=Absorbance; ε=Extinction Coefficient (Molar absorptivity); C=Sample Concentration; L=Path length, $\alpha=\varepsilon_{protein260}/\varepsilon_{protein280}$, $\beta=\varepsilon_{DNA260}/\varepsilon_{DNA280}$, wherein the extinction coefficients are specific for the genome and for the capsid of the isolated rAAV particles under non-denaturing conditions.

5. The method of claim 4, wherein the obtaining the feed sample comprises one or more purification processes selected from centrifugation, depth filtration, tangential flow filtration, ultrafiltration, affinity chromatography, size exclusion chromatography, ion exchange chromatography, and hydrophobic interaction chromatography.

6. A method of producing a pharmaceutical unit dosage comprising a predetermined quantity of recombinant adeno-associated virus (rAAV) genomes, comprising (1) isolating rAAV particles under non-denaturing conditions from a feed comprising an impurity, (2) determining percentage vector genome copies per capsid (Vg %) of the isolated rAAV particles, (3) using the Vg % to determine the quality of the isolated rAAV particles, (4) producing a bulk drug substance comprising the isolated rAAV particles and a pharmaceutically acceptable carrier when the isolated rAAV particles meet a predetermined quality requirement, and (5) producing a pharmaceutical unit dosage comprising a physically discreet unit of the bulk drug substance comprising the predetermined quantity of the rAAV genomes, wherein the Vg % is determined by a) determining the absorbance of a composition comprising the rAAV particles at least at 260 nm and at 280 nm, under non-denaturing conditions, and b) calculating the Vg %, wherein the calculating comprises using the following equations $$Vg(GC/\text{mL}) = \frac{(A_{260} - \alpha A_{280})}{\varepsilon_{DNA260}\,(1 - \alpha/\beta)L},$$

-continued $$Cp(\text{capsid/mL}) = \frac{(A_{280} - A_{260}/\beta)}{\varepsilon_{protein280}\,(1 - \alpha/\beta)L},$$

and $$Vg\ \% = Vg/Cp$$

wherein A=Absorbance; ε=Extinction Coefficient (Molar absorptivity); C=Sample Concentration; L=Path length, $\alpha=\varepsilon_{protein260}/\varepsilon_{protein280}$, $\beta=\varepsilon_{DNA260}/\varepsilon_{DNA280}$, wherein the extinction coefficients are specific for the genome and for the capsid of the isolated rAAV particles under non-denaturing conditions.

7. The method of claim 6, wherein the isolating rAAV particles under non-denaturing conditions comprises one or more purification processes selected from centrifugation, depth filtration, tangential flow filtration, ultrafiltration, affinity chromatography, size exclusion chromatography, ion exchange chromatography, and hydrophobic interaction chromatography.

8. A method of producing a pharmaceutical unit dosage comprising a predetermined quantity of recombinant adeno-associated virus (rAAV) genomes, comprising (1) isolating rAAV particles under non-denaturing conditions from a feed comprising an impurity, (2) determining percentage vector genome copies per capsid (Vg %) of the isolated rAAV particles, (3) using the Vg % to produce a bulk drug substance comprising a predetermined genome titer of the isolated rAAV particles and a pharmaceutically acceptable carrier, and (4) producing a pharmaceutical unit dosage comprising a physically discreet unit of the bulk drug substance comprising the predetermined quantity of the rAAV genomes, wherein the Vg % is determined by a) determining the absorbance of a composition comprising the rAAV particles at least at 260 nm and at 280 nm, under non-denaturing conditions, and b) calculating the Vg %, wherein the calculating comprises using the following equations $$Vg(GC/\text{mL}) = \frac{(A_{260} - \alpha A_{280})}{\varepsilon_{DNA260}\,(1 - \alpha/\beta)L},$$

$$Cp(\text{capsid/mL}) = \frac{(A_{280} - A_{260}/\beta)}{\varepsilon_{protein280}\,(1 - \alpha/\beta)L},$$

and $$Vg\ \% = Vg/Cp$$

wherein A=Absorbance; ε=Extinction Coefficient (Molar absorptivity); C=Sample Concentration; L=Path length, $\alpha=\varepsilon_{protein260}/\varepsilon_{protein280}$, $\beta=\varepsilon_{DNA260}/\varepsilon_{DNA280}$, wherein the extinction coefficients are specific for the genome and for the capsid of the isolated rAAV particles under non-denaturing conditions.

9. The method of claim 8, wherein the isolating rAAV particles under non-denaturing conditions comprises one or more purification processes selected from centrifugation, depth filtration, tangential flow filtration, ultrafiltration, affinity chromatography, size exclusion chromatography, ion exchange chromatography, and hydrophobic interaction chromatography.

* * * * *